United States Patent
Hao et al.

(10) Patent No.: US 11,192,931 B2
(45) Date of Patent: Dec. 7, 2021

(54) RELAXIN FUSION POLYPEPTIDES AND USES THEREOF

(71) Applicants: MedImmune, LLC, Gaithersburg, MD (US); MedImmune Limited, Cambridge (GB)

(72) Inventors: Weidong Hao, Gaithersburg, MD (US); Andrew Garcia, Gaithersburg, MD (US); Changshou Gao, Gaithersburg, MD (US); Isabelle Sermadiras, Cambridge (GB)

(73) Assignees: MedImmune, LLC, Gaithersburg, MD (US); MedImmune Limited, Cambridge (GB)

( * ) Notice: Subject to any disclaimer, the term of this patent is extended or adjusted under 35 U.S.C. 154(b) by 0 days.

(21) Appl. No.: 16/480,568

(22) PCT Filed: Jan. 24, 2018

(86) PCT No.: PCT/EP2018/051757
§ 371 (c)(1),
(2) Date: Jul. 24, 2019

(87) PCT Pub. No.: WO2018/138170
PCT Pub. Date: Aug. 2, 2018

(65) Prior Publication Data
US 2019/0352366 A1    Nov. 21, 2019

Related U.S. Application Data

(60) Provisional application No. 62/450,338, filed on Jan. 25, 2017.

(51) Int. Cl.
  *C07K 14/64* (2006.01)
  *A61K 38/00* (2006.01)
  *A61P 9/04* (2006.01)
  *A61K 9/00* (2006.01)

(52) U.S. Cl.
  CPC .......... *C07K 14/64* (2013.01); *A61K 9/0019* (2013.01); *A61P 9/04* (2018.01); *A61K 38/00* (2013.01); *C07K 2319/30* (2013.01)

(58) Field of Classification Search
  None
  See application file for complete search history.

(56) References Cited

U.S. PATENT DOCUMENTS

| | | | |
|---|---|---|---|
| 7,271,149 B2 * | 9/2007 | Glaesner | C12N 15/62 514/7.2 |
| 2014/0187491 A1 * | 7/2014 | Wilmen | C07K 14/64 514/12.7 |
| 2015/0125444 A1 * | 5/2015 | Tsui | C07K 16/1027 424/133.1 |

FOREIGN PATENT DOCUMENTS

| | | | |
|---|---|---|---|
| WO | WO 02/060919 | * | 8/2002 |
| WO | 2013/004607 A1 | | 1/2013 |

OTHER PUBLICATIONS

Bathgate, et al., "Relaxin Family Peptides and Their Receptors", *Physiol Rev*, Jan. 2013, vol. 93, pp. 405-480.

* cited by examiner

*Primary Examiner* — Marianne P Allen

(57) ABSTRACT

The present invention relates to Relaxin fusion polypeptides, in particular to Relaxin 2 fusion polypeptides and uses thereof. Thus, the invention provides Relaxin fusion polypeptides, nucleic acid molecules, vectors, host cells, pharmaceutical compositions and kits comprising the same and uses of the same including methods of treatment. The polypeptides and compositions of the invention may be useful, in particular, in the treatment of cardiovascular diseases, for example for the treatment of heart failure.

15 Claims, 30 Drawing Sheets

Specification includes a Sequence Listing.

| # | Name | | | | | |
|---|---|---|---|---|---|---|
| 1. | Fc_hRLX2_4-15AA | hFc-G1 | GGSP | A | 15AA | B |
| 2. | Fc-TM_hRLX2_4-15AA | hFc-G1-TM | GGSP | A | 15AA | B |
| 3. | Fc-FQQ_hRLX2_4-15AA | hFc-G1-FQQ | GGSP | A | 15AA | B |
| 4. | Fc-YTE_hRLX2_4-15AA | hFc-G1-YTE | GGSP | A | 15AA | B |
| 5. | Fc-YTE-TM_hRLX2_4-15AA | hFc-G1-YTE-TM | GGSP | A | 15AA | B |
| 6. | Fc-YTE-FQQ_hRLX2_4-15AA | hFc-G1-YTE-FQQ | GGSP | A | 15AA | B |
| 7. | Fc-G4P_hRLX2_4-15AA | hFc-G4P | GGSP | A | 15AA | B |
| 8. | Fc_hRLX2_15-15AA | hFc-G1 | 15AA | A | 15AA | B |
| 9. | Fc-TM_hRLX2_15-15AA | hFc-G1-TM | 15AA | A | 15AA | B |
| 10. | Fc-FQQ_hRLX2_15-15AA | hFc-G1-FQQ | 15AA | A | 15AA | B |
| 11. | Fc-YTE_hRLX2_15-15AA | hFc-G1-YTE | 15AA | A | 15AA | B |
| 12. | Fc-YTE-TM_hRLX2_15-15AA | hFc-G1-YTE-TM | 15AA | A | 15AA | B |
| 13. | Fc-YTE-FQQ_hRLX2_15-15AA | hFc-G1-YTE-FQQ | 15AA | A | 15AA | B |
| 14. | Fc-G4P_hRLX2_15-15AA | hFc-G4P | 15AA | A | 15AA | B |
| 15. | Fc-TMΔTHTΔK_hRLX2_21-15AA | hFc-G1-TM-ΔTHT-ΔK | 21AA | A | 15AA | B |
| 16. | Fc-TMΔTHTΔK_hRLX2(BA)_21-15AA | hFc-G1-TM-ΔTHT-ΔK | 21AA | B | 15AA | A |
| 17. | hRLX2-Fc-TMΔTHTΔK_15-24AA | A | 15AA | B | 24AA | hFc-G1-TM-ΔTHT-ΔK |
| 18. | hRLX2(BA)-Fc-TMΔTHTΔK_15-24AA | B | 15AA | A | 24AA | hFc-G1-TM-ΔTHT-ΔK |

Key
YTE : M252Y, S254T, T256E
FQQ : L234F, L235Q, K322Q
TM : L234F, L235E, P331S
Fc-G4P: IgG4 Fc with S228P ΔTHT: D221G K222G T223G H224S T225A
ΔK: ΔK447
24AA: AAAGGGGSGGGGSGGGGSGGGGSA (SEQ ID NO: 70)
21AA: GGGGSGGGGSGGGGSGGGGGS (SEQ ID NO: 69)
15AA: GGGGSGGGGSGGGGS (SEQ ID NO: 57)

Figure 1

Fc_hRLX2_4-15AA

Nucleotide sequence

GATAAAACCCATACCTGCCCGCCGTGCCCGGCGCCGGAACTGCTGGG
CGGCCCGAGCGTGTTTCTGTTTCCGCCGAAACCGAAAGATACCCTGAT
GATTAGCCGCACCCCGGAAGTGACCTGCGTGGTGGTGGATGTGAGCC
ATGAAGATCCGGAAGTGAAATTTAACTGGTATGTGGATGGCGTGGAAGT
GCATAACGCGAAAACCAAACCGCGCGAAGAACAGTATAACAGCACCTAT
CGCGTGGTGAGCGTGCTGACCGTGCTGCATCAGGATTGGCTGAACGG
CAAAGAATATAAATGCAAAGTGAGCAACAAAGCGCTGCCGGCGCCGATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCAGCCCG</u>CAGCTGTATAGCGCGCTGGCGAACAAA
TGCTGCCATGTGGGCTGCACCAAACGCAGCCTGGCGCGCTTTTGC<u>GG
CGGCGGCGGCAGCGGCGGCGGCGGCAGCGGCGGCGGCGGCAGC</u>AG
CTGGATGGAAGAAGTGATTAAACTGTGTGGCCGCGAACTGGTGCGCGC
GCAGATTGCGATTTGCGGCATGAGCACCTGGAGCTGA (SEQ ID NO: 1)

Amino acid sequence

DKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK<u>GGSP</u>QLYSALANKCCHVGCTKRSLA
RFC<u>GGGGSGGGGSGGGGS</u>SWMEEVIKLCGRELVRAQIAICGMSTWS
(SEQ ID NO: 2)

Figure 2

Fc-TM_hRLX2_4-15AA

<u>Nucleotide sequence</u>

GATAAAACCCATACCTGCCCGCCGTGCCCGGCGCCGGAA<u>TTTGAA</u>GGC
GGCCCGAGCGTGTTTCTGTTTCCGCCGAAACCGAAAGATACCCTGATG
ATTAGCCGCACCCCGGAAGTGACCTGCGTGGTGGTGGATGTGAGCCAT
GAAGATCCGGAAGTGAAATTTAACTGGTATGTGGATGGCGTGGAAGTG
CATAACGCGAAAACCAAACCGCGCGAAGAACAGTATAACAGCACCTATC
GCGTGGTGAGCGTGCTGACCGTGCTGCATCAGGATTGGCTGAACGGC
AAAGAATATAAATGCAAAGTGAGCAACAAAGCGCTGCCGGCG<u>AGC</u>ATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCAGCCCG</u>CAGCTGTATAGCGCGCTGGCGAACAAA
TGCTGCCATGTGGGCTGCACCAAACGCAGCCTGGCGCGCTTTTGC<u>GG
CGGCGGCGGCAGCGGCGGCGGCGGCAGCGGCGGCGGCGGCAGC</u>AG
CTGGATGGAAGAAGTGATTAAACTGTGTGGCCGCGAACTGGTGCGCGC
GCAGATTGCGATTTGCGGCATGAGCACCTGGAGCTGA (SEQ ID NO: 3)

<u>Amino acid sequence</u>

DKTHTCPPCPAPE<u>FE</u>GGPSVFLFPPKPKDTLMISRTPEVTCVVVDVSHEDP
EVKFNWYVDGVEVHNAKTKPREEQYNSTYRVVSVLTVLHQDWLNGKEYK
CKVSNKALPA<u>S</u>IEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK<u>GGSP</u>QLYSALANKCCHVGCTKRSLA
RFC<u>GGGGSGGGGSGGGGS</u>SWMEEVIKLCGRELVRAQIAICGMSTWS
(SEQ ID NO: 4)

Figure 3

Fc-FQQ_hRLX2_4-15AA

Nucleotide sequence

GATAAAACCCATACCTGCCCGCCGTGCCCGGCGCCGGAA<u>TTTCA</u>GGGC
GGCCCGAGCGTGTTTCTGTTTCCGCCGAAACCGAAAGATACCCTGATG
ATTAGCCGCACCCCGGAAGTGACCTGCGTGGTGGATGTGAGCCAT
GAAGATCCGGAAGTGAAATTTAACTGGTATGTGGATGGCGTGGAAGTG
CATAACGCGAAAACCAAACCGCGCGAAGAACAGTATAACAGCACCTATC
GCGTGGTGAGCGTGCTGACCGTGCTGCATCAGGATTGGCTGAACGGC
AAAGAATATAAATGC<u>CAG</u>GTGAGCAACAAAGCGCTGCCGGCGCCGATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCAGCCCG</u>CAGCTGTATAGCGCGCTGGCGAACAAA
TGCTGCCATGTGGGCTGCACCAAACGCAGCCTGGCGCGCTTTTGC<u>GG
CGGCGGCGGCAGCGGCGGCGGCGGCAGCGGCGGCGGCGGCAGC</u>AG
CTGGATGGAAGAAGTGATTAAACTGTGTGGCCGCGAACTGGTGCGCGC
GCAGATTGCGATTTGCGGCATGAGCACCTGGAGCTGA (SEQ ID NO: 5)

Amino acid sequence

DKTHTCPPCPAPE<u>FQ</u>QGGPSVFLFPPKPKDTLMISRTPEVTCVVVDVSHE
DPEVKFNWYVDGVEVHNAKTKPREEQYNSTYRVVSVLTVLHQDWLNGKE
YKC<u>Q</u>VSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK<u>GGSP</u>QLYSALANKCCHVGCTKR
SLARFC<u>GGGGSGGGGSGGGGS</u>SWMEEVIKLCGRELVRAQIAICGMSTW
S (SEQ ID NO: 6)

Figure 4

Fc-YTE_hRLX2_4-15AA

Nucleotide sequence

GATAAAACCCATACCTGCCCGCCGTGCCCGGCGCCGGAACTGCTGGG
CGGCCCGAGCGTGTTTCTGTTTCCGCCGAAACCGAAAGATACCCTG<u>TA
TATTA</u><u>C</u>CCGC<u>GAA</u>CCGGAAGTGACCTGCGTGGTGGTGGATGTGAGCC
ATGAAGATCCGGAAGTGAAATTTAACTGGTATGTGGATGGCGTGGAAGT
GCATAACGCGAAAACCAAACCGCGCGAAGAACAGTATAACAGCACCTAT
CGCGTGGTGAGCGTGCTGACCGTGCTGCATCAGGATTGGCTGAACGG
CAAAGAATATAAATGCAAAGTGAGCAACAAAGCGCTGCCGGCGCCGATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCAGCCCG</u>CAGCTGTATAGCGCGCTGGCGAACAAA
TGCTGCCATGTGGGCTGCACCAAACGCAGCCTGGCGCGCTTTTGC<u>GG
CGGCGGCGGCAGCGGCGGCGGCGGCAGCGGCGGCGGCGGCAGC</u>AG
CTGGATGGAAGAAGTGATTAAACTGTGTGGCCGCGAACTGGTGCGCGC
GCAGATTGCGATTTGCGGCATGAGCACCTGGAGCTGATAA (SEQ ID NO: 7)

Amino acid sequence
DKTHTCPPCPAPELLGGPSVFLFPPKPKDTL<u>Y</u>I<u>TRE</u>PEVTCVVVDVSHEDP
EVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK<u>GGSP</u>QLYSALANKCCHVGCTKRSLA
RFC<u>GGGGSGGGGSGGGGS</u>SWMEEVIKLCGRELVRAQIAICGMSTWS
(SEQ ID NO: 8)

Figure 5

Fc-YTE-TM_hRLX2_4-15AA

Nucleotide sequence

GATAAAACCCATACCTGCCCGCCGTGCCCGGCGCCGGAA<u>TTTGAA</u>GGC
GGCCCGAGCGTGTTTCTGTTTCCGCCGAAACCGAAAGATACCCTG<u>TAT</u>
ATTA<u>C</u>CCGC<u>GAA</u>CCGGAAGTGACCTGCGTGGTGGATGTGAGCCAT
GAAGATCCGGAAGTGAAATTTAACTGGTATGTGGATGGCGTGGAAGTG
CATAACGCGAAAACCAAACCGCGCGAAGAACAGTATAACAGCACCTATC
GCGTGGTGAGCGTGCTGACCGTGCTGCATCAGGATTGGCTGAACGGC
AAAGAATATAAATGCAAAGTGAGCAACAAAGCGCTGCCGGCG<u>AGC</u>ATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCAGCCCG</u>CAGCTGTATAGCGCGCTGGCGAACAAA
TGCTGCCATGTGGGCTGCACCAAACGCAGCCTGGCGCGCTTTGC<u>GG
CGGCGGCGGCAGCGGCGGCGGCGGCAGCGGCGGCGGCGGCAGC</u>AG
CTGGATGGAAGAAGTGATTAAACTGTGTGGCCGCGAACTGGTGCGCGC
GCAGATTGCGATTTGCGGCATGAGCACCTGGAGCTGA (SEQ ID NO: 9)

Amino acid sequence

DKTHTCPPCPAPE<u>FE</u>GGPSVFLFPPKPKDTL<u>YITRE</u>PEVTCVVVDVSHEDP
EVKFNWYVDGVEVHNAKTKPREEQYNSTYRVVSVLTVLHQDWLNGKEYK
CKVSNKALPA<u>S</u>IEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK<u>GGSP</u>QLYSALANKCCHVGCTKRSLA
RFC<u>GGGGSGGGGSGGGGS</u>SWMEEVIKLCGRELVRAQIAICGMSTWS
(SEQ ID NO: 10)

Figure 6

Fc-YTE-FQQ_hRLX2_4-15AA

Nucleotide sequence

GATAAAACCCATACCTGCCCGCCGTGCCCGGCGCCGGAA<u>TTTC</u><u>A</u>GGGC
GGCCCGAGCGTGTTTCTGTTTCCGCCGAAACCGAAAGATACCCTG<u>TAT</u>
ATTA<u>C</u>CCGC<u>GAA</u>CCGGAAGTGACCTGCGTGGTGGTGGATGTGAGCCAT
GAAGATCCGGAAGTGAAATTTAACTGGTATGTGGATGGCGTGGAAGTG
CATAACGCGAAAACCAAACCGCGCGAAGAACAGTATAACAGCACCTATC
GCGTGGTGAGCGTGCTGACCGTGCTGCATCAGGATTGGCTGAACGGC
AAAGAATATAAATGC<u>CAG</u>GTGAGCAACAAAGCGCTGCCGGCGCCGATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCAGCCCG</u>CAGCTGTATAGCGCGCTGGCGAACAAA
TGCTGCCATGTGGGCTGCACCAAACGCAGCCTGGCGCGCTTTTGC<u>GG</u>
<u>CGGCGGCGGCAGCGGCGGCGGCGGCAGCGGCGGCGGCGGCAGC</u>AG
CTGGATGGAAGAAGTGATTAAACTGTGTGGCCGCGAACTGGTGCGCGC
GCAGATTGCGATTTGCGGCATGAGCACCTGGAGCTGATAA (SEQ ID NO: 11)

Amino acid sequence

DKTHTCPPCPAPE<u>FQ</u>GGPSVFLFPPKPKDTL<u>Y</u><u>IT</u><u>R</u>EPEVTCVVVDVSHEDP
EVKFNWYVDGVEVHNAKTKPREEQYNSTYRVVSVLTVLHQDWLNGKEYK
C<u>Q</u>VSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK<u>GGSP</u>QLYSALANKCCHVGCTKRSLA
RFC<u>GGGGSGGGGSGGGGS</u>SWMEEVIKLCGRELVRAQIAICGMSTWS
(SEQ ID NO: 12)

Figure 7

Fc-G4P_hRLX2_4-15AA

Nucleotide sequence

GAATCTAAGTACGGCCCTCCCTGCCCACCCTGCCCTGCCCCTGAATTT
CTGGGCGGACCCTCCGTGTTCCTGTTCCCACCCAAGCCCAAGGACAC
CCTGATGATCAGCCGGACCCCTGAAGTGACCTGCGTGGTGGTGGACG
TGTCCCAGGAAGATCCCGAGGTCCAGTTCAATTGGTACGTGGACGGCG
TGGAAGTGCACAACGCCAAGACCAAGCCCAGAGAGGAACAGTTCAACA
GCACCTACCGGGTGGTGTCCGTGCTGACCGTGCTGCACCAGGACTGG
CTGAACGGCAAGAGTACAAGTGCAAGGTGTCCAACAAGGGCCTGCC
CAGCTCCATCGAGAAAACCATCAGCAAGGCCAAGGGCCAGCCCCGCG
AGCCCCAGGTCTACACACTGCCTCCAGCCAGGAAGAGATGACCAAGA
ACCAGGTGTCCCTGACCTGTCTGGTGAAAGGCTTCTACCCCAGCGATA
TCGCCGTGGAATGGGAGAGCAACGGCCAGCCCGAGAACAACTACAAG
ACCACCCCTCCCGTGCTGGACAGCGACGGCAGCTTCTTTCTGTACTCC
CGGCTGACCGTGGACAAGAGCCGGTGGCAGGAAGGCAACGTCTTCAG
CTGCAGCGTGATGCACGAGGCCCTGCACAACCACTACACCCAGAAGTC
CCTGAGCCTGAGCCTGGGCAAG<u>GGCGGCAGCCCG</u>CAGCTGTATAGCG
CGCTGGCGAACAAATGCTGCCATGTGGGCTGCACCAAACGCAGCCTG
GCGCGCTTTTGC<u>GGCGGCGGCGGCAGCGGCGGCGGCGGCAGCGGC
GGCGGCGGCAGC</u>AGCTGGATGGAAGAAGTGATTAAACTGTGTGGCCG
CGAACTGGTGCGCGCGCAGATTGCGATTTGCGGCATGAGCACCTGGA
GCTGA (SEQ ID NO: 13)

Amino acid sequence

ESKYGPPCPPCPAPEFLGGPSVFLFPPKPKDTLMISRTPEVTCVVVDVSQE
DPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSRWQE
GNVFSCSVMHEALHNHYTQKSLSLSLGK<u>GGSP</u>QLYSALANKCCHVGCTK
RSLARFC<u>GGGGSGGGGSGGGGS</u>SWMEEVIKLCGRELVRAQIAICGMST
WS (SEQ ID NO: 14)

Figure 8

Fc_hRLX2_15-15AA

Nucleotide sequence

GATAAAACCCATACCTGCCCGCCGTGCCCGGCGCCGGAACTGCTGGG
CGGCCCGAGCGTGTTTCTGTTTCCGCCGAAACCGAAAGATACCCTGAT
GATTAGCCGCACCCCGGAAGTGACCTGCGTGGTGGTGGATGTGAGCC
ATGAAGATCCGGAAGTGAAATTTAACTGGTATGTGGATGGCGTGGAAGT
GCATAACGCGAAAACCAAACCGCGCGAAGAACAGTATAACAGCACCTAT
CGCGTGGTGAGCGTGCTGACCGTGCTGCATCAGGATTGGCTGAACGG
CAAAGAATATAAATGCAAAGTGAGCAACAAAGCGCTGCCGGCGCCGATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAAGGCGGCGGCGGCAGCGGCGGCGGCGGCAGCGGCGGCG
GCGGCAGCCAGCTGTATAGCGCGCTGGCGAACAAATGCTGCCATGTGG
GCTGCACCAAACGCAGCCTGGCGCGCTTTGCGGCGGCGGCGGCAG
CGGCGGCGGCGGCAGCGGCGGCGGCGGCAGCAGCTGGATGGAAGA
AGTGATTAAACTGTGTGGCCGCGAACTGGTGCGCGCGCAGATTGCGAT
TTGCGGCATGAGCACCTGGAGCTGA (SEQ ID NO: 15)

Amino acid sequence

DKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGKGGGGSGGGGSGGGGSQLYSALAN
KCCHVGCTKRSLARFCGGGGSGGGGSGGGGSSWMEEVIKLCGRELVRA
QIAICGMSTWS (SEQ ID NO: 16)

Figure 9

Fc-TM_hRLX2_15-15AA

<u>Nucleotide sequence</u>

GATAAAACCCATACCTGCCCGCCGTGCCCGGCGCCGGAA<u>TTTGAA</u>GGC
GGCCCGAGCGTGTTTCTGTTTCCGCCGAAACCGAAAGATACCCTGATG
ATTAGCCGCACCCCGGAAGTGACCTGCGTGGTGGTGGATGTGAGCCAT
GAAGATCCGGAAGTGAAATTTAACTGGTATGTGGATGGCGTGGAAGTG
CATAACGCGAAAACCAAACCGCGCGAAGAACAGTATAACAGCACCTATC
GCGTGGTGAGCGTGCTGACCGTGCTGCATCAGGATTGGCTGAACGGC
AAAGAATATAAATGCAAAGTGAGCAACAAAGCGCTGCCGGCG<u>AGC</u>ATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCGGCGGCAGCGGCGGCGGCGGCAGCGGCGGCG
GCGGCAGC</u>CAGCTGTATAGCGCGCTGGCGAACAAATGCTGCCATGTGG
GCTGCACCAAACGCAGCCTGGCGCGCTTTGC<u>GGCGGCGGCGGCAG
CGGCGGCGGCGGCAGCGGCGGCGGCGGCAGC</u>AGCTGGATGGAAGA
AGTGATTAAACTGTGTGGCCGCGAACTGGTGCGCGCGCAGATTGCGAT
TTGCGGCATGAGCACCTGGAGCTGA (SEQ ID NO: 17)

<u>Amino acid sequence</u>

DKTHTCPPCPAPE<u>FE</u>GGPSVFLFPPKPKDTLMISRTPEVTCVVVDVSHEDP
EVKFNWYVDGVEVHNAKTKPREEQYNSTYRVVSVLTVLHQDWLNGKEYK
CKVSNKALPA<u>S</u>IEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK<u>GGGGSGGGGSGGGGS</u>QLYSALAN
KCCHVGCTKRSLARFC<u>GGGGSGGGGSGGGGS</u>SWMEEVIKLCGRELVRA
QIAICGMSTWS (SEQ ID NO: 18)

Fc-FQQ_hRLX2_15-15AA

Nucleotide sequence

GATAAAACCCATACCTGCCCGCCGTGCCCGGCGCCGGAA<u>TTCA</u>GGGC
GGCCCGAGCGTGTTTCTGTTTCCGCCGAAACCGAAAGATACCCTGATG
ATTAGCCGCACCCCGGAAGTGACCTGCGTGGTGGTGGATGTGAGCCAT
GAAGATCCGGAAGTGAAATTTAACTGGTATGTGGATGGCGTGGAAGTG
CATAACGCGAAAACCAAACCGCGCGAAGAACAGTATAACAGCACCTATC
GCGTGGTGAGCGTGCTGACCGTGCTGCATCAGGATTGGCTGAACGGC
AAAGAATATAAATGC<u>CAG</u>GTGAGCAACAAAGCGCTGCCGGCGCCGATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCGGCGGCAGCGGCGGCGGCGGCAGCGGCGGCG
GCGGCAGC</u>CAGCTGTATAGCGCGCTGGCGAACAAATGCTGCCATGTGG
GCTGCACCAAACGCAGCCTGGCGCGCTTTTGC<u>GGCGGCGGCGGCAG
CGGCGGCGGCGGCAGCGGCGGCGGCGGCAGC</u>AGCTGGATGGAAGA
AGTGATTAAACTGTGTGGCCGCGAACTGGTGCGCGCGCAGATTGCGAT
TTGCGGCATGAGCACCTGGAGCTGA (SEQ ID NO: 19)

Amino acid sequence

DKTHTCPPCPAPE<u>FQ</u>QGGPSVFLFPPKPKDTLMISRTPEVTCVVVDVSHE
DPEVKFNWYVDGVEVHNAKTKPREEQYNSTYRVVSVLTVLHQDWLNGKE
YKC<u>Q</u>VSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK<u>GGGGSGGGGSGGGGS</u>QLYSAL
ANKCCHVGCTKRSLARFC<u>GGGGSGGGGSGGGGS</u>SWMEEVIKLCGRELV
RAQIAICGMSTWS (SEQ ID NO: 20)

Figure 11

Fc-YTE_hRLX2_15-15AA

Nucleotide sequence

GATAAACCCATACCTGCCCGCCGTGCCCGGCGCCGGAACTGCTGGG
CGGCCCGAGCGTGTTTCTGTTTCCGCCGAAACCGAAAGATACCCTG<u>TA
TATTA</u>C<u>CCGCGAA</u>CCGGAAGTGACCTGCGTGGTGGTGGATGTGAGCC
ATGAAGATCCGGAAGTGAAATTTAACTGGTATGTGGATGGCGTGGAAGT
GCATAACGCGAAAACCAAACCGCGCGAAGAACAGTATAACAGCACCTAT
CGCGTGGTGAGCGTGCTGACCGTGCTGCATCAGGATTGGCTGAACGG
CAAAGAATATAAATGCAAAGTGAGCAACAAAGCGCTGCCGGCGCCGATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCGGCGGCAGCGGCGGCGGCGGCAGCGGCGGCG
GCGGCAGC</u>CAGCTGTATAGCGCGCTGGCGAACAAATGCTGCCATGTGG
GCTGCACCAAACGCAGCCTGGCGCGCTTTTGC<u>GGCGGCGGCGGCAG
CGGCGGCGGCGGCAGCGGCGGCGGCGGCAGC</u>AGCTGGATGGAAGA
AGTGATTAAACTGTGTGGCCGCGAACTGGTGCGCGCGCAGATTGCGAT
TTGCGGCATGAGCACCTGGAGCTGATAA (SEQ ID NO: 21)

Amino acid sequence

DKTHTCPPCPAPELLGGPSVFLFPPKPKDTL<u>YITRE</u>PEVTCVVVDVSHEDP
EVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK<u>GGGGSGGGGSGGGGS</u>QLYSALAN
KCCHVGCTKRSLARFC<u>GGGGSGGGGSGGGGS</u>SWMEEVIKLCGRELVRA
QIAICGMSTWS (SEQ ID NO: 22)

Figure 12

Fc-YTE-TM_hRLX2_15-15AA

Nucleotide sequence

GATAAAACCCATACCTGCCCGCCGTGCCCGGCGCCGGAA<u>TTTGAA</u>GGC
GGCCCGAGCGTGTTTCTGTTTCCGCCGAAACCGAAAGATACCCTG<u>TAT</u>
ATTA<u>C</u>CCGC<u>GAA</u>CCGGAAGTGACCTGCGTGGTGGTGGATGTGAGCCAT
GAAGATCCGGAAGTGAAATTTAACTGGTATGTGGATGGCGTGGAAGTG
CATAACGCGAAAACCAAACCGCGCGAAGAACAGTATAACAGCACCTATC
GCGTGGTGAGCGTGCTGACCGTGCTGCATCAGGATTGGCTGAACGGC
AAAGAATATAAATGCAAAGTGAGCAACAAAGCGCTGCCGGCG<u>AGC</u>ATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCGGCGGCAGCGGCGGCGGCGGCAGCGGCGGCG
GCGGCAGC</u>CAGCTGTATAGCGCGCTGGCGAACAAATGCTGCCATGTGG
GCTGCACCAAACGCAGCCTGGCGCGCTTTTGC<u>GGCGGCGGCGGCAG
CGGCGGCGGCGGCAGCGGCGGCGGCGGCAGC</u>AGCTGGATGGAAGA
AGTGATTAAACTGTGTGGCCGCGAACTGGTGCGCGCGCAGATTGCGAT
TTGCGGCATGAGCACCTGGAGCTGA (SEQ ID NO: 23)

Amino acid sequence

DKTHTCPPCPAPE<u>FE</u>GGPSVFLFPPKPKDTL<u>YITRE</u>PEVTCVVVDVSHEDP
EVKFNWYVDGVEVHNAKTKPREEQYNSTYRVVSVLTVLHQDWLNGKEYK
CKVSNKALPA<u>S</u>IEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK<u>GGGGSGGGGSGGGGS</u>QLYSALAN
KCCHVGCTKRSLARFC<u>GGGGSGGGGSGGGGS</u>SWMEEVIKLCGRELVRA
QIAICGMSTWS (SEQ ID NO: 24)

Fc-YTE-FQQ_hRLX2_15-15AA

<u>Nucleotide sequence</u>

GATAAAACCCATACCTGCCCGCCGTGCCCGGCGCCGGAA<u>TTTCA</u>GGGC
GGCCCGAGCGTGTTTCTGTTTCCGCCGAAACCGAAAGATACCCTG<u>TAT</u>
<u>ATTA</u><u>C</u>CCGC<u>GAA</u>CCGGAAGTGACCTGCGTGGTGGATGTGAGCCAT
GAAGATCCGGAAGTGAAATTTAACTGGTATGTGGATGGCGTGGAAGTG
CATAACGCGAAAACCAAACCGCGCGAAGAACAGTATAACAGCACCTATC
GCGTGGTGAGCGTGCTGACCGTGCTGCATCAGGATTGGCTGAACGGC
AAAGAATATAAATGC<u>CAG</u>GTGAGCAACAAAGCGCTGCCGGCGCCGATT
GAAAAAACCATTAGCAAAGCGAAAGGCCAGCCGCGCGAACCGCAGGT
GTATACCCTGCCGCCGAGCCGCGATGAACTGACCAAAAACCAGGTGAG
CCTGACCTGCCTGGTGAAAGGCTTTTATCCGAGCGATATTGCGGTGGA
ATGGGAAAGCAACGGCCAGCCGGAAAACAACTATAAAACCACCCCGCC
GGTGCTGGATAGCGATGGCAGCTTTTTTCTGTATAGCAAACTGACCGTG
GATAAAAGCCGCTGGCAGCAGGGCAACGTGTTTAGCTGCAGCGTGATG
CATGAAGCGCTGCATAACCATTATACCCAGAAAAGCCTGAGCCTGAGCC
CGGGCAAA<u>GGCGGCGGCGGCAGCGGCGGCGGCGGCAGCGGCGGCG</u>
<u>GCGGCAGC</u>CAGCTGTATAGCGCGCTGGCGAACAAATGCTGCCATGTGG
GCTGCACCAAACGCAGCCTGGCGCGCTTTTGC<u>GGCGGCGGCGGCAG</u>
<u>CGGCGGCGGCGGCAGCGGCGGCGGCGGCAGC</u>AGCTGGATGGAAGA
AGTGATTAAACTGTGTGGCCGCGAACTGGTGCGCGCGCAGATTGCGAT
TTGCGGCATGAGCACCTGGAGCTGATAA (SEQ ID NO: 25)

<u>Amino acid sequence</u>

DKTHTCPPCPAPE<u>FQ</u>GGPSVFLFPPKPKDTL<u>YITRE</u>PEVTCVVVDVSHEDP
EVKFNWYVDGVEVHNAKTKPREEQYNSTYRVVSVLTVLHQDWLNGKEYK
C<u>Q</u>VSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNV
FSCSVMHEALHNHYTQKSLSLSPGK<u>GGGGSGGGGSGGGGS</u>QLYSALAN
KCCHVGCTKRSLARFC<u>GGGGSGGGGSGGGGS</u>SWMEEVIKLCGRELVRA
QIAICGMSTWS (SEQ ID NO: 26)

Fc-G4P_hRLX2_15-15AA

Nucleotide sequence

GAATCTAAGTACGGCCCTCCCTGCCCACCCTGCCCTGCCCCTGAATTT
CTGGGCGGACCCTCCGTGTTCCTGTTCCCACCCAAGCCCAAGGACAC
CCTGATGATCAGCCGGACCCCTGAAGTGACCTGCGTGGTGGTGGACG
TGTCCCAGGAAGATCCCGAGGTCCAGTTCAATTGGTACGTGGACGGCG
TGGAAGTGCACAACGCCAAGACCAAGCCCAGAGAGGAACAGTTCAACA
GCACCTACCGGGTGGTGTCCGTGCTGACCGTGCTGCACCAGGACTGG
CTGAACGGCAAAGAGTACAAGTGCAAGGTGTCCAACAAGGGCCTGCC
CAGCTCCATCGAGAAAACCATCAGCAAGGCCAAGGGCCAGCCCCGCG
AGCCCCAGGTCTACACACTGCCTCCAGCCAGGAAGAGATGACCAAGA
ACCAGGTGTCCCTGACCTGTCTGGTGAAAGGCTTCTACCCCAGCGATA
TCGCCGTGGAATGGGAGAGCAACGGCCAGCCCGAGAACAACTACAAG
ACCACCCCTCCCGTGCTGGACAGCGACGGCAGCTTCTTTCTGTACTCC
CGGCTGACCGTGGACAAGAGCCGGTGGCAGGAAGGCAACGTCTTCAG
CTGCAGCGTGATGCACGAGGCCCTGCACAACCACTACACCCAGAAGTC
CCTGAGCCTGAGCCTGGGCAAG<u>GGCGGCGGCGGCAGCGGCGGCGG
CGGCAGCGGCGGCGGCGGCAGC</u>CAGCTGTATAGCGCGCTGGCGAAC
AAATGCTGCCATGTGGGCTGCACCAAACGCAGCCTGGCGCGCTTTTGC
<u>GGCGGCGGCGGCAGCGGCGGCGGCGGCAGCGGCGGCGGCGGCAG
C</u>AGCTGGATGGAAGAAGTGATTAAACTGTGTGGCCGCGAACTGGTGCG
CGCGCAGATTGCGATTTGCGGCATGAGCACCTGGAGCTGA (SEQ ID
NO: 27)

Amino acid sequence

ESKYGPPCPPCPAPEFLGGPSVFLFPPKPKDTLMISRTPEVTCVVVDVSQE
DPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSRWQE
GNVFSCSVMHEALHNHYTQKSLSLSLGK<u>GGGGSGGGGSGGGGS</u>QLYSA
LANKCCHVGCTKRSLARFC<u>GGGGSGGGGSGGGGS</u>SWMEEVIKLCGREL
VRAQIAICGMSTWS (SEQ ID NO: 28)

Fc-TMΔTHTΔK_hRLX2_21-15AA

Nucleotide sequence

GGAGGTGGAAGCGCTTGTCCTCCATGCCCGGCGCCTGAGTTCGAGG
GCGGACCCTCCGTGTTCCTGTTCCCCCCAAAGCCCAAGGACACCCTGA
TGATCTCCCGGACCCCCGAAGTGACCTGCGTGGTGGTGGACGTGTCC
CACGAGGACCCTGAAGTGAAGTTCAATTGGTACGTGGACGGCGTGGAA
GTGCACAACGCCAAGACCAAGCCCAGAGAGGAACAGTACAACTCCACC
TACCGGGTGGTGTCCGTGCTGACCGTGCTGCACCAGGACTGGCTGAA
CGGCAAAGAGTACAAGTGCAAGGTCTCCAACAAGGCCCTGCCCGCCT
CCATCGAAAAGACCATCTCCAAGGCCAAGGGCCAGCCCCGCGAGCCT
CAGGTGTACACACTGCCCCCAGCCGGGAAGAGATGACCAAGAACCA
GGTGTCCCTGACCTGTCTGGTGAAAGGCTTCTACCCCTCCGATATCGC
TGTGGAATGGGAGTCCAACGGCCAGCCCGAGAACAACTACAAGACCAC
CCCCCCTGTGCTGGACTCCGACGGCTCATTCTTCCTGTACTCCAAGCT
GACCGTGGACAAGTCCCGGTGGCAGCAGGGCAACGTGTTCTCCTGCT
CCGTGATGCACGAGGCCCTGCACAACCACTACACCCAGAAGTCTCTAA
GCTTGAGCCCCGGCGGAGGTGGTGGAAGCGGAGGAGGTGGCTCTGG
AGGGGGTGGAAGCGGAGGTGGAGGTGGATCCCAGCTGTATAGCGCGC
TGGCGAACAAATGCTGCCATGTGGGCTGCACCAAACGCAGCCTGGCG
CGCTTTTGCGGCGGCGGCGGCAGCGGCGGCGGCGGCAGCGGCGGC
GGCGGCAGCAGCTGGATGGAAGAAGTGATTAAACTGTGTGGCCGCGA
ACTGGTGCGCGCGCAGATTGCGATTTGCGGCATGAGCACCTGGAGC
(SEQ ID NO: 61)

Amino acid sequence

GGGSACPPCPAPEFEGGPSVFLFPPKPKDTLMISRTPEVTCVVVDVSHED
PEVKFNWYVDGVEVHNAKTKPREEQYNSTYRVVSVLTVLHQDWLNGKEY
KCKVSNKALPASIEKTISKAKGQPREPQVYTLPPSREEMTKNQVSLTCLVK
GFYPSDIAVEWESNGQPENNYKTTPPVLDSDGSFFLYSKLTVDKSRWQQG
NVFSCSVMHEALHNHYTQKSLSLSPGGGGSGGGGSGGGGSGGGGS
QLYSALANKCCHVGCTKRSLARFCGGGGSGGGGSGGGGSSWMEEVIKL
CGRELVRAQIAICGMSTWS (SEQ ID NO: 62)

Figure 16

Fc-TMΔTHTΔK_hRLX2(BA)_21-15AA

Nucleotide sequence

GGAGGTGGAAGCGCTTGTCCTCCATGCCCGGCGCCTGAGTTCGAGG
GCGGACCCTCCGTGTTCCTGTTCCCCCCAAAGCCCAAGGACACCCTGA
TGATCTCCCGGACCCCCGAAGTGACCTGCGTGGTGGTGGACGTGTCC
CACGAGGACCCTGAAGTGAAGTTCAATTGGTACGTGGACGGCGTGGAA
GTGCACAACGCCAAGACCAAGCCCAGAGAGGAACAGTACAACTCCACC
TACCGGGTGGTGTCCGTGCTGACCGTGCTGCACCAGGACTGGCTGAA
CGGCAAAGAGTACAAGTGCAAGGTCTCCAACAAGGCCCTGCCCGCCT
CCATCGAAAAGACCATCTCCAAGGCCAAGGGCCAGCCCCGCGAGCCT
CAGGTGTACACACTGCCCCCAGCCGGGAAGAGATGACCAAGAACCA
GGTGTCCCTGACCTGTCTGGTGAAAGGCTTCTACCCCTCCGATATCGC
TGTGGAATGGGAGTCCAACGGCCAGCCCGAGAACAACTACAAGACCAC
CCCCCCTGTGCTGGACTCCGACGGCTCATTCTTCCTGTACTCCAAGCT
GACCGTGGACAAGTCCCGGTGGCAGCAGGGCAACGTGTTCTCCTGCT
CCGTGATGCACGAGGCCCTGCACAACCACTACACCCAGAAGTCTCTAA
GCTTGAGCCCCGGCGGAGGTGGTGGAAGCGGAGGAGGTGGCTCTGG
AGGGGGTGGAAGCGGAGGTGGAGGTGGATCCTCCTGGATGGAGGAG
GTTATCAAGCTGTGTGGACGCGAACTGGTGCGCGCTCAGATCGCGATA
TGCGGGATGTCCACATGGTCA<u>GGCGGCGGAGGCAGCGGCGGTGGCG</u>
<u>GCAGCGGCGGGGGAGGTTCT</u>CAGCTCTACTCAGCGCTCGCTAATAAGT
GTTGTCATGTGGGATGCACAAAGCGGTCTCTCGCCAGATTCTGC (SEQ
ID NO: 63)

Amino acid sequence

GGGSACPPCPAPEFEGGPSVFLFPPKPKDTLMISRTPEVTCVVVDVSHED
PEVKFNWYVDGVEVHNAKTKPREEQYNSTYRVVSVLTVLHQDWLNGKEY
KCKVSNKALPASIEKTISKAKGQPREPQVYTLPPSREEMTKNQVSLTCLVK
GFYPSDIAVEWESNGQPENNYKTTPPVLDSDGSFFLYSKLTVDKSRWQQG
NVFSCSVMHEALHNHYTQKSLSLSP<u>GGGGSGGGGSGGGGSGGGGS</u>
SWMEEVIKLCGRELVRAQIAICGMSTWS<u>GGGGSGGGGSGGGGS</u>QLYSAL
ANKCCHVGCTKRSLARFC (SEQ ID NO: 64)

Figure 17 hRLX2-Fc-TMΔTHTΔK_15-24AA

Nucleotide sequence

CAGCTGTATAGCGCGCTGGCGAACAAATGCTGCCATGTGGGCTGCACC
AAACGCAGCCTGGCGCGCTTTTGC<u>GGCGGCGGCGGCAGCGGCGGCG
GCGGCAGCGGCGGCGGCGGCAGCAGC</u>TGGATGGAAGAAGTGATTAAA
CTGTGTGGCCGCGAACTGGTGCGCGCGCAGATTGCGATTTGCGGCAT
GAGCACCTGGAGC<u>GCGGCCGCGGGTGGAGGTGGATCCGGAGGAGGT
GGAAGCGGAGGAGGTGGAAGCGGAGGAGGTGGAAGC</u>GCTTGTCCTC
CATGCCCGGCGCCTGAG<u>TTCGAG</u>GGCGGACCCTCCGTGTTCCTGTTC
CCCCCAAAGCCCAAGGACACCCTGATGATCTCCCGGACCCCCGAAGTG
ACCTGCGTGGTGGTGGACGTGTCCCACGAGGACCCTGAAGTGAAGTT
CAATTGGTACGTGGACGGCGTGGAAGTGCACAACGCCAAGACCAAGC
CCAGAGAGGAACAGTACAACTCCACCTACCGGGTGGTGTCCGTGCTGA
CCGTGCTGCACCAGGACTGGCTGAACGGCAAAGAGTACAAGTGCAAG
GTCTCCAACAAGGCCCTGCCCGCC<u>TCC</u>ATCGAAAAGACCATCTCCAAG
GCCAAGGGCCAGCCCCGCGAGCCTCAGGTGTACACACTGCCCCCCAG
CCGGGAAGAGATGACCAAGAACCAGGTGTCCCTGACCTGTCTGGTGA
AAGGCTTCTACCCCTCCGATATCGCTGTGGAATGGGAGTCCAACGGCC
AGCCCGAGAACAACTACAAGACCACCCCCCCTGTGCTGGACTCCGAC
GGCTCATTCTTCCTGTACTCCAAGCTGACCGTGGACAAGTCCCGGTGG
CAGCAGGGCAACGTGTTCTCCTGCTCCGTGATGCACGAGGCCCTGCA
CAACCACTACACCCAGAAGTCTCTGTCCCTGAGCCCC<u>GGC</u> (SEQ ID
NO: 65)

Amino acid sequence

QLYSALANKCCHVGCTKRSLARFC<u>GGGGSGGGGSGGGGS</u>SWMEEVIKL
CGRELVRAQIAICGMSTWS<u>AAAGGGGSGGGGSGGGGSGGGGS</u>ACPPC
PAPE<u>FE</u>GGPSVFLFPPKPKDTLMISRTPEVTCVVVDVSHEDPEVKFNWYV
DGVEVHNAKTKPREEQYNSTYRVVSVLTVLHQDWLNGKEYKCKVSNKAL
PA<u>S</u>IEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMH
EALHNHYTQKSLSLSP<u>G</u> (SEQ ID NO: 66)

Figure 18 hRLX2(BA)-Fc-TMΔTHTΔK_15-24AA

Nucleotide sequence

TCCTGGATGGAGGAGGTTATCAAGCTGTGTGGACGCGAACTGGTGCG
CGCTCAGATCGCGATATGCGGGATGTCCACATGGTCA<u>GGCGGCGGAG
GCAGCGGCGGTGGCGGCAGCGGCGGGGGAGGTTCT</u>CAGCTCTACTC
AGCGCTCGCTAATAAGTGTTGTCATGTGGGATGCACAAAGCGGTCTCTC
GCCAGATTCTG<u>CGCGGCCGCGGGTGGAGGTGGATCCGGAGGAGGTG
GAAGCGGAGGAGGTGGAAGCGGAGGAGGTGGAAGC</u>GCTTGTCCTCC
ATGCCCGGCGCCTGAG<u>TTCGAG</u>GGCGGACCCTCCGTGTTCCTGTTCC
CCCCAAAGCCCAAGGACACCCTGATGATCTCCCGGACCCCCGAAGTGA
CCTGCGTGGTGGTGGACGTGTCCACGAGGACCCTGAAGTGAAGTTC
AATTGGTACGTGGACGGCGTGGAAGTGCACAACGCCAAGACCAAGCC
CAGAGAGGAACAGTACAACTCCACCTACCGGGTGGTGTCCGTGCTGAC
CGTGCTGCACCAGGACTGGCTGAACGGCAAAGAGTACAAGTGCAAGG
TCTCCAACAAGGCCCTGCCCGCC<u>TCC</u>ATCGAAAAGACCATCTCCAAGG
CCAAGGGCCAGCCCCGCGAGCCTCAGGTGTACACACTGCCCCCCAGC
CGGGAAGAGATGACCAAGAACCAGGTGTCCCTGACCTGTCTGGTGAAA
GGCTTCTACCCCTCCGATATCGCTGTGGAATGGGAGTCCAACGGCCAG
CCCGAGAACAACTACAAGACCACCCCCCCTGTGCTGGACTCCGACGG
CTCATTCTTCCTGTACTCCAAGCTGACCGTGGACAAGTCCCGGTGGCA
GCAGGGCAACGTGTTCTCCTGCTCCGTGATGCACGAGGCCCTGCACA
ACCACTACACCCAGAAGTCTCTGTCCCTGAGCCCC<u>GGC</u> (SEQ ID NO: 67)

Amino acid sequence

SWMEEVIKLCGRELVRAQIAICGMSTWS<u>GGGGSGGGGSGGGGS</u>QLYSAL
ANKCCHVGCTKRSLARFC<u>AAAGGGGSGGGGSGGGGSGGGGS</u>ACPPCP
APEFEGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
SIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHE
ALHNHYTQKSLCLSPG (SEQ ID NO: 68)

Figure 19

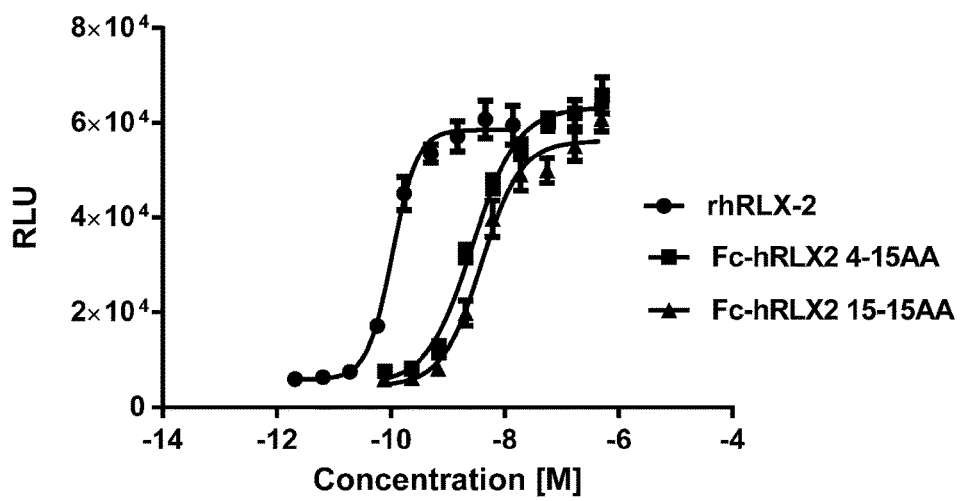
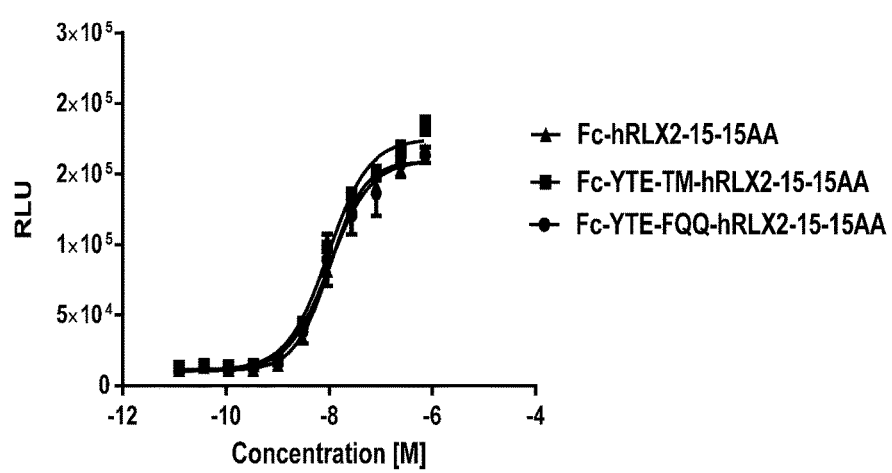
Figure 20

|  | Half-life ($T_{1/2}$) (Day) | CL or CL/F (mL/hr/kg) |
|---|---|---|
| Mice IV (6 mg/kg) | 5.58 (0.43) | 16.75 (0.75) |
| Mice SC (6 mg/kg) | 7.06 (1.75) | 9.87 (1.31) |

|  | Half-life ($T_{1/2}$) (Day) | Dose-normalized Cmax (kg*ng/mL/mg) | CL/F (mL/hr/kg) |
|---|---|---|---|
| Mice SC (1 mg/kg) | 4.59 (0.76) | 1360.57 (165.57) | 3.55 (0.40) |
| Mice SC (6 mg/kg) | 7.06 (1.75) | 740.31 (21.62) | 9.87 (1.31) |
| Mice SC (30 mg/kg) | 5.38 (0.79) | 324.98 (76.73) | 20.80 (0.93) |

A
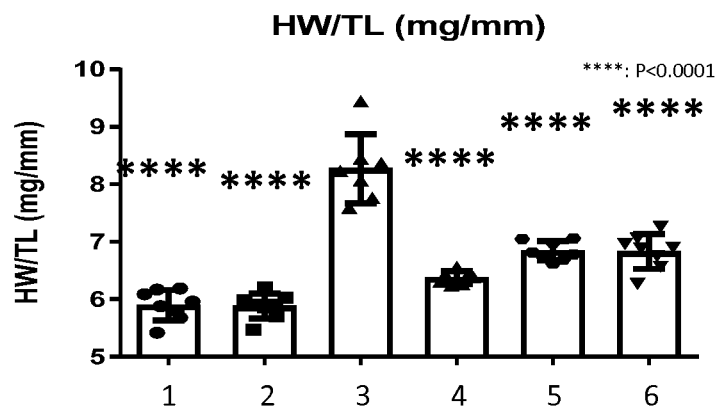
B
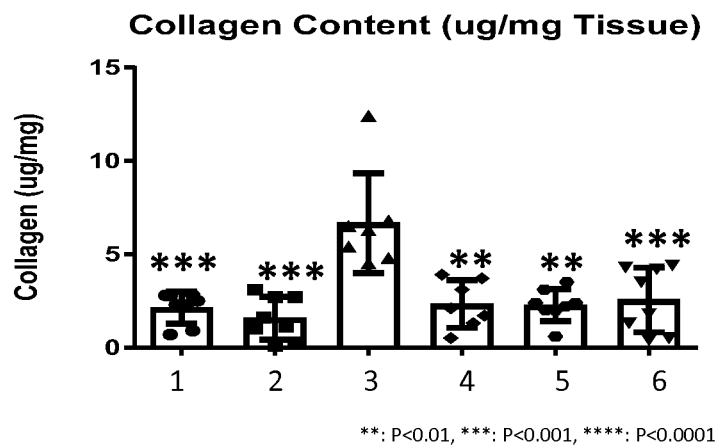
Figure 29

SEQUENCE LISTING

```
<160> NUMBER OF SEQ ID NOS: 70

<210> SEQ ID NO 1
<211> LENGTH: 897
<212> TYPE: DNA
<213> ORGANISM: Artificial Sequence
<220> FEATURE:
<223> OTHER INFORMATION: DNA encoding fusion protein

<400> SEQUENCE: 1
gataaaaccc atacctgccc gccgtgcccg gcgccggaac tgctgggcgg cccgagcgtg      60
tttctgtttc cgccgaaacc gaaagatacc ctgatgatta gccgcacccc ggaagtgacc     120
tgcgtggtgg tggatgtgag ccatgaagat ccggaagtga aatttaactg gtatgtggat     180
ggcgtggaag tgcataacgc gaaaaccaaa ccgcgcgaag aacagtataa cagcacctat     240
cgcgtggtga gcgtgctgac cgtgctgcat caggattggc tgaacggcaa agaatataaa     300
tgcaaagtga gcaacaaagc gctgccggcg ccgattgaaa aaaccattag caaagcgaaa     360
ggccagccgc gcgaaccgca ggtgtatacc ctgccgccga gccgcgatga actgaccaaa     420
aaccaggtga gcctgacctg cctggtgaaa ggcttttatc cgagcgatat tgcggtggaa     480
tgggaaagca acggccagcc ggaaaacaac tataaaacca cccgccggt gctggatagc     540 gatggcagct tttttctgta tagcaaactg accgtggata aagccgctg gcagcagggc     600 aacgtgttta gctgcagcgt gatgcatgaa gcgctgcata accattatac ccagaaaagc     660
ctgagcctga gcccgggcaa aggcggcagc ccgcagctgt atagcgcgct ggcgaacaaa     720
tgctgccatg tgggctgcac caaacgcagc ctggcgcgct tttgcggcgg cggcggcagc     780
ggcggcggcg gcagcggcgg cggcggcagc agctggatgg aagaagtgat taaactgtgt     840
ggccgcgaac tggtgcgcgc gcagattgcg atttgcggca tgagcacctg gagctga      897
```

<210> SEQ ID NO 2
<211> LENGTH: 298

<212> TYPE: PRT
<213> ORGANISM: Artificial Sequence
<220> FEATURE:
<223> OTHER INFORMATION: fusion protein

<400> SEQUENCE: 2

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys Gly Gly Ser Pro Gln Leu Tyr Ser Ala Leu Ala Asn Lys
225                 230                 235                 240
Cys Cys His Val Gly Cys Thr Lys Arg Ser Leu Ala Arg Phe Cys Gly
                245                 250                 255
Gly Gly Gly Ser Gly Gly Gly Gly Ser Gly Gly Gly Gly Ser Ser Trp
            260                 265                 270
Met Glu Glu Val Ile Lys Leu Cys Gly Arg Glu Leu Val Arg Ala Gln
        275                 280                 285
Ile Ala Ile Cys Gly Met Ser Thr Trp Ser
    290                 295
```

<210> SEQ ID NO 3
<211> LENGTH: 897
<212> TYPE: DNA
<213> ORGANISM: Artificial Sequence
<220> FEATURE:
<223> OTHER INFORMATION: DNA encoding fusion protein

<400> SEQUENCE: 3

```
gataaaaccc atacctgccc gccgtgcccg gcgccggaat tgaaggcgg cccgagcgtg      60 tttctgtttc cgccgaaacc gaaagatacc ctgatgatta gccgcacccc ggaagtgacc     120
tgcgtggtgg tggatgtgag ccatgaagat ccggaagtga aatttaactg gtatgtggat     180
```

```
ggcgtggaag tgcataacgc gaaaaccaaa ccgcgcgaag aacagtataa cagcacctat    240
cgcgtggtga gcgtgctgac cgtgctgcat caggattggc tgaacggcaa agaatataaa    300
tgcaaagtga gcaacaaagc gctgccggcg agcattgaaa aaaccattag caaagcgaaa    360
ggccagccgc gcgaaccgca ggtgtatacc ctgccgccga ccgcgatga actgaccaaa     420 aaccaggtga gcctgacctg cctggtgaaa ggcttttatc cgagcgatat tgcggtggaa    480
tgggaaagca acggccagcc ggaaaacaac tataaaacca ccccgccggt gctggatagc    540
gatggcagct ttttctgta tagcaaactg accgtggata aaagccgctg gcagcagggc     600
aacgtgttta gctgcagcgt gatgcatgaa gcgctgcata accattatac ccagaaaagc    660
ctgagcctga gcccgggcaa aggcggcagc ccgcagctgt atagcgcgct ggcgaacaaa    720
tgctgccatg tgggctgcac caaacgcagc ctggcgcgct tttgcggcgg cggcggcagc    780
ggcggcggcg gcagcggcgg cggcggcagc agctggatgg aagaagtgat taaactgtgt    840
ggccgcgaac tggtgcgcgc gcagattgcg atttgcggca tgagcacctg gagctga      897
```

`<210>` SEQ ID NO 4
`<211>` LENGTH: 298
`<212>` TYPE: PRT
`<213>` ORGANISM: Artificial Sequence
`<220>` FEATURE:
`<223>` OTHER INFORMATION: Fusion protein

`<400>` SEQUENCE: 4

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Pro Gln Leu Tyr Ser Ala Leu Ala Asn Lys
225                 230                 235                 240
```

```
Cys Cys His Val Gly Cys Thr Lys Arg Ser Leu Ala Arg Phe Cys Gly
            245                 250                 255

Gly Gly Gly Ser Gly Gly Gly Ser Gly Gly Gly Ser Ser Trp
        260                 265                 270

Met Glu Glu Val Ile Lys Leu Cys Gly Arg Glu Leu Val Arg Ala Gln
        275                 280                 285

Ile Ala Ile Cys Gly Met Ser Thr Trp Ser
        290                 295
```

<210> SEQ ID NO 5
<211> LENGTH: 897
<212> TYPE: DNA
<213> ORGANISM: Artificial Sequence
<220> FEATURE:
<223> OTHER INFORMATION: DNA encoding fusion protein

<400> SEQUENCE: 5

```
gataaaaccc atacctgccc gccgtgcccg gcgccggaat tcagggcgg cccgagcgtg    60
tttctgtttc gccgaaaacc gaaagatacc ctgatgatta gccgcacccc ggaagtgacc   120
tgcgtggtgg tggatgtgag ccatgaagat ccggaagtga atttaactg gtatgtggat   180
ggcgtggaag tgcataacgc gaaaaccaaa ccgcgcgaag aacagtataa cagcacctat   240
cgcgtggtga gcgtgctgac cgtgctgcat caggattggc tgaacggcaa agaatataaa   300
tgccaggtga gcaacaaagc gctgccggcg ccgattgaaa aaaccattag caaagcgaaa   360
ggccagccgc gcgaaccgca ggtgtatacc ctgccgccga ccgcgatga actgaccaaa   420
aaccaggtga gcctgacctg cctggtgaaa ggctttttatc cgagcgatat tgcggtggaa   480
tgggaaagca cggccagcc ggaaaacaac tataaaacca ccccgccggt gctggatagc   540
gatggcagct ttttctgtta tagcaaactg accgtggata aaagccgctg gcagcagggc   600
aacgtgttta gctgcagcgt gatgcatgaa gcgctgcata accattatac ccagaaaagc   660
ctgagcctga gcccgggcaa aggcggcagc ccgcagctgt atagcgcgct ggcgaacaaa   720
tgctgccatg tgggctgcac caaacgcagc ctggcgcgct tttgcggcgg cggcggcagc   780
ggcggcggcg gcagcggcgg cggcggcagc agctggatgg aagaagtgat taaactgtgt   840
ggccgcgaac tggtgcgcgc gcagattgcg atttgcggca tgagcacctg gagctga     897
```

<210> SEQ ID NO 6
<211> LENGTH: 299
<212> TYPE: PRT
<213> ORGANISM: Artificial Sequence
<220> FEATURE:
<223> OTHER INFORMATION: Fusion protein

<400> SEQUENCE: 6

```
Asp Lys Thr His Thr Cys Pro Pro Cys Pro Ala Pro Glu Phe Gln Gln
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
```

```
                     85                  90                  95
Gly Lys Glu Tyr Lys Cys Gln Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
                195                 200                 205

Met His Glu Ala Leu His Asn His Tyr Thr Gln Lys Ser Leu Ser Leu
            210                 215                 220

Ser Pro Gly Lys Gly Gly Ser Pro Gln Leu Tyr Ser Ala Leu Ala Asn
225                 230                 235                 240

Lys Cys Cys His Val Gly Cys Thr Lys Arg Ser Leu Ala Arg Phe Cys
                245                 250                 255

Gly Gly Gly Gly Ser Gly Gly Gly Ser Gly Gly Gly Gly Ser Ser
                260                 265                 270

Trp Met Glu Glu Val Ile Lys Leu Cys Gly Arg Glu Leu Val Arg Ala
            275                 280                 285

Gln Ile Ala Ile Cys Gly Met Ser Thr Trp Ser
290                 295
```

<210> SEQ ID NO 7
<211> LENGTH: 900
<212> TYPE: DNA
<213> ORGANISM: Artificial Sequence
<220> FEATURE:
<223> OTHER INFORMATION: DNA encoding fusion protein

<400> SEQUENCE: 7

```
gataaaaccc atacctgccc gccgtgcccg gcgccggaac tgctgggcgg cccgagcgtg    60
tttctgtttc cgccgaaacc gaaagatacc ctgtatatta cccgcgaacc ggaagtgacc   120
tgcgtggtgg tggatgtgag ccatgaagat ccggaagtga aatttaactg gtatgtggat   180
ggcgtggaag tgcataacgc gaaaaccaaa ccgcgcgaag aacagtataa cagcaccctt   240
cgcgtggtga gcgtgctgac cgtgctgcat caggattggc tgaacggcaa agaatataaa   300
tgcaaagtga gcaacaaagc gctgccggcg ccgattgaaa aaaccattag caaagcgaaa   360
ggccagccgc gcgaaccgca ggtgtatacc ctgccgccga gccgcgatga actgaccaaa   420
aaccaggtga gcctgacctg cctggtgaaa ggcttttatc cgagcgatat tgcggtggaa   480
tgggaaagca acggccagcc ggaaaacaac tataaaacca ccccgccggt gctggatagc   540
gatggcagct tttttctgta tagcaaactg accgtggata aaagccgctg cagcagggc    600
aacgtgttta gctgcagcgt gatgcatgaa gcgctgcata accattatac ccagaaaagc   660
ctgagcctga gcccgggcaa aggcggcagc ccgcagctgt atagcgcgct ggcgaacaaa   720
tgctgccatg tgggctgcac caaacgcagc ctggcgcgct tttgcggcgg cggcggcagc   780
ggcggcggcg gcagcggcgg cggcggcagc agctggatga agaagtgat taaactgtgt   840
```
ggccgcgaac tggtgcgcgc gcagattgcg atttgcggca tgagcacctg gagctgataa    900

<210> SEQ ID NO 8
<211> LENGTH: 298
<212> TYPE: PRT
<213> ORGANISM: Artificial Sequence
<220> FEATURE:
<223> OTHER INFORMATION: Fusion protein

<400> SEQUENCE: 8

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Pro Gln Leu Tyr Ser Ala Leu Ala Asn Lys
225                 230                 235                 240

Cys Cys His Val Gly Cys Thr Lys Arg Ser Leu Ala Arg Phe Cys Gly
                245                 250                 255

Gly Gly Gly Ser Gly Gly Gly Ser Gly Gly Gly Ser Ser Trp
            260                 265                 270

Met Glu Glu Val Ile Lys Leu Cys Gly Arg Glu Leu Val Arg Ala Gln
        275                 280                 285

Ile Ala Ile Cys Gly Met Ser Thr Trp Ser
    290                 295
```

<210> SEQ ID NO 9
<211> LENGTH: 897
<212> TYPE: DNA
<213> ORGANISM: Artificial Sequence
<220> FEATURE:
<223> OTHER INFORMATION: DNA encoding fusion protein

<400> SEQUENCE: 9

```
gataaaaccc atacctgccc gccgtgcccg gcgccggaat ttgaaggcgg cccgagcgtg    60
tttctgtttc cgccgaaacc gaaagatacc ctgtatatta cccgcgaacc ggaagtgacc   120
tgcgtggtgg tggatgtgag ccatgaagat ccggaagtga atttaactg gtatgtggat    180
ggcgtggaag tgcataacgc gaaaaccaaa ccgcgcgaag aacagtataa cagcacctat   240
cgcgtggtga gcgtgctgac cgtgctgcat caggattggc tgaacggcaa agaatataaa   300
tgcaaagtga gcaacaaagc gctgccggcg agcattgaaa aaaccattag caaagcgaaa   360
ggccagccgc gcgaaccgca ggtgtatacc ctgccgccga ccgcgatga actgaccaaa    420
aaccaggtga gcctgacctg cctggtgaaa ggcttttatc cgagcgatat tgcggtggaa   480
tgggaaagca acggccagcc ggaaaacaac tataaaacca ccccgccggt gctggatagc   540
gatggcagct ttttctgta tagcaaactg accgtggata aagccgctg gcagcagggc    600
aacgtgttta gctgcagcgt gatgcatgaa gcgctgcata accattatac ccagaaaagc   660
ctgagcctga gcccgggcaa aggcggcagc ccgcagctgt atagcgcgct ggcgaacaaa   720
tgctgccatg tgggctgcac caaacgcagc ctggcgcgct tttgcggcgg cggcggcagc   780
ggcggcggcg cagcggcgg cggcggcagc agctggatgg aagaagtgat taaactgtgt   840
ggccgcgaac tggtgcgcgc gcagattgcg atttgcggca tgagcacctg gagctga      897
```

<210> SEQ ID NO 10
<211> LENGTH: 298
<212> TYPE: PRT
<213> ORGANISM: Artificial Sequence
<220> FEATURE:
<223> OTHER INFORMATION: Fusion protein

<400> SEQUENCE: 10

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
    210                 215                 220
Pro Gly Lys Gly Gly Ser Pro Gln Leu Tyr Ser Ala Leu Ala Asn Lys
225                 230                 235                 240
Cys Cys His Val Gly Cys Thr Lys Arg Ser Leu Ala Arg Phe Cys Gly
                245                 250                 255
Gly Gly Gly Ser Gly Gly Gly Ser Gly Gly Gly Ser Ser Trp
            260                 265                 270
Met Glu Glu Val Ile Lys Leu Cys Gly Arg Glu Leu Val Arg Ala Gln
            275                 280                 285
Ile Ala Ile Cys Gly Met Ser Thr Trp Ser
            290                 295
```

<210> SEQ ID NO 11
<211> LENGTH: 900
<212> TYPE: DNA
<213> ORGANISM: Artificial Sequence
<220> FEATURE:
<223> OTHER INFORMATION: DNA encoding fusion protein

<400> SEQUENCE: 11

```
gataaaaccc atacctgccc gccgtgcccg gcgccggaat tcagggcgg cccgagcgtg    60
tttctgtttc cgccgaaacc gaaagatacc ctgtatatta cccgcgaacc ggaagtgacc   120
tgcgtggtgg tggatgtgag ccatgaagat ccggaagtga atttaactg gtatgtggat   180
ggcgtggaag tgcataacgc gaaaaccaaa ccgcgcgaag aacagtataa cagcacctat   240
cgcgtggtga gcgtgctgac cgtgctgcat caggattggc tgaacggcaa agaatataaa   300
tgccaggtga gcaacaaagc gctgccggcg ccgattgaaa aaccattag caaagcgaaa   360
ggccagcccg cgaaccgca ggtgtatacc ctgccgccga ccgcgatga actgaccaaa   420
aaccaggtga gcctgacctg cctggtgaaa ggctttttatc cgagcgatat tgcggtggaa   480
tgggaaagca acggccagcc ggaaaacaac tataaaacca ccccgccggt gctggatagc   540
gatggcagct tttttctgta tagcaaactg accgtggata aaagccgctg gcagcagggc   600
aacgtgttta gctgcagcgt gatgcatgaa gcgctgcata accattatac ccagaaaagc   660
ctgagcctga gcccgggcaa aggcggcagc ccgcagctgt atagcgcgct ggcgaacaaa   720
tgctgccatg tgggctgcac caaacgcagc ctggcgcgct tttgcggcgg cggcggcagc   780
ggcggcggcg gcagcggcgg cggcggcagc agctggatgg aagaagtgat taaactgtgt   840
ggccgcgaac tggtgcgcgc gcagattgcg atttgcggca tgagcacctg gagctgataa   900
```

<210> SEQ ID NO 12
<211> LENGTH: 298
<212> TYPE: PRT
<213> ORGANISM: Artificial Sequence
<220> FEATURE:
<223> OTHER INFORMATION: Fusion protein

<400> SEQUENCE: 12

```
Asp Lys Thr His Thr Cys Pro Pro Cys Pro Ala Pro Glu Phe Gln Gly
1               5                  10                  15
Gly Pro Ser Val Phe Leu Phe Pro Pro Lys Pro Lys Asp Thr Leu Tyr
            20                  25                  30
Ile Thr Arg Glu Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
             85                  90                  95

Lys Glu Tyr Lys Cys Gln Val Ser Asn Lys Ala Leu Pro Ala Pro Ile
        100                 105                 110

Glu Lys Thr Ile Ser Lys Ala Lys Gly Gln Pro Arg Glu Pro Gln Val
    115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Pro Gln Leu Tyr Ser Ala Leu Ala Asn Lys
225                 230                 235                 240

Cys Cys His Val Gly Cys Thr Lys Arg Ser Leu Ala Arg Phe Cys Gly
                245                 250                 255

Gly Gly Gly Ser Gly Gly Gly Gly Ser Gly Gly Gly Gly Ser Ser Trp
            260                 265                 270

Met Glu Glu Val Ile Lys Leu Cys Gly Arg Glu Leu Val Arg Ala Gln
        275                 280                 285

Ile Ala Ile Cys Gly Met Ser Thr Trp Ser
        290                 295

<210> SEQ ID NO 13
<211> LENGTH: 903
<212> TYPE: DNA
<213> ORGANISM: Artificial Sequence
<220> FEATURE:
<223> OTHER INFORMATION: DNA encoding fusion protein

<400> SEQUENCE: 13
gaatctaagt acggccctcc ctgcccaccc tgccctgccc ctgaatttct gggcggaccc      60
tccgtgttcc tgttcccacc caagcccaag gacaccctga tgatcagccg gacccctgaa     120
gtgacctgcg tggtggtgga cgtgtcccag gaagatcccg aggtccagtt caattggtac     180
gtggacggcg tggaagtgca caacgccaag accaagccca gaggaacagt tcaacagc      240 acctaccggg tggtgtccgt gctgaccgtg ctgcaccagg actggctgaa cggcaaagag     300
tacaagtgca aggtgtccaa caagggcctg cccagctcca tcgagaaaac catcagcaag     360
gccaagggcc agccccgcga gccccaggtc tacacactgc ctcccagcca ggaagagatg     420
accaagaacc aggtgtccct gacctgtctg gtgaaaggct tctacccag cgatatcgcc     480 gtggaatggg agagcaacgg ccagcccgag aacaactaca agaccacccc tcccgtgctg     540
gacagcgacg gcagcttctt tctgtactcc cggctgaccg tggacaagag ccggtggcag     600
gaaggcaact cttcagctg cagcgtgatg cacgaggccc tgcacaacca ctacacccag     660
aagtccctga gcctgagcct gggcaagggc ggcagcccgc agctgtatag cgcgctggcg     720

```
aacaaatgct gccatgtggg ctgcaccaaa cgcagcctgg cgcgcttttg cggcggcggc    780
ggcagcggcg gcggcggcag cggcggcggc ggcagcagct ggatggaaga agtgattaaa    840
ctgtgtggcc gcgaactggt gcgcgcgcag attgcgattt gcggcatgag cacctggagc    900
tga                                                                  903
```

```
<210> SEQ ID NO 14
<211> LENGTH: 300
<212> TYPE: PRT
<213> ORGANISM: Artificial Sequence
<220> FEATURE:
<223> OTHER INFORMATION: fusion protein

<400> SEQUENCE: 14
```

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Ser Pro Gln Leu Tyr Ser Ala Leu Ala
225                 230                 235                 240

Asn Lys Cys Cys His Val Gly Cys Thr Lys Arg Ser Leu Ala Arg Phe
                245                 250                 255

Cys Gly Gly Gly Ser Gly Gly Gly Gly Ser Gly Gly Gly Gly Ser
            260                 265                 270

Ser Trp Met Glu Glu Val Ile Lys Leu Cys Gly Arg Glu Leu Val Arg
        275                 280                 285

Ala Gln Ile Ala Ile Cys Gly Met Ser Thr Trp Ser
    290                 295                 300

```
<210> SEQ ID NO 15
<211> LENGTH: 930
```

```
<212> TYPE: DNA
<213> ORGANISM: Artificial Sequence
<220> FEATURE:
<223> OTHER INFORMATION: DNA encoding fusion protein

<400> SEQUENCE: 15
gataaaaccc atacctgccc gccgtgcccg gcgccggaac tgctgggcgg cccgagcgtg    60
tttctgtttc cgccgaaacc gaaagatacc ctgatgatta gccgcacccc ggaagtgacc   120
tgcgtggtgg tggatgtgag ccatgaagat ccggaagtga aatttaactg gtatgtggat   180
ggcgtggaag tgcataacgc gaaaaccaaa ccgcgcgaag aacagtataa cagcacctat   240
cgcgtggtga gcgtgctgac cgtgctgcat caggattggc tgaacggcaa agaatataaa   300
tgcaaagtga gcaacaaagc gctgccggcg ccgattgaaa aaaccattag caaagcgaaa   360
ggccagccgc gcgaaccgca ggtgtatacc ctgccgccga ccgcgatgaa actgaccaaa   420
aaccaggtga gcctgacctg cctggtgaaa ggcttttatc cgagcgatat tgcggtggaa   480
tgggaaagca acggccagcc ggaaaacaac tataaaacca ccccgccggt gctggatagc   540
gatggcagct ttttttctgta tagcaaactg accgtggata aaagccgctg gcagcagggc   600
aacgtgttta gctgcagcgt gatgcatgaa gcgctgcata accattatac ccagaaaagc   660
ctgagcctga gcccgggcaa aggcggcggc ggcagcggcg gcggcggcag cggcggcggc   720
ggcagccagc tgtatagcgc gctggcgaac aaatgctgcc atgtgggctg caccaaacgc   780
agcctggcgc gcttttgcgg cggcggcggc agcggcggcg gcggcagcgg cggcggcggc   840
agcagctgga tggaagaagt gattaaactg tgtggccgcg aactggtgcg cgcgcagatt   900
gcgatttgcg gcatgagcac ctggagctga                                   930
```

```
<210> SEQ ID NO 16
<211> LENGTH: 309
<212> TYPE: PRT
<213> ORGANISM: Artificial Sequence
<220> FEATURE:
<223> OTHER INFORMATION: fusion protein

<400> SEQUENCE: 16

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
```

```
Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
        180                 185                 190

Asp Lys Ser Arg Trp Gln Gln Gly Asn Val Phe Ser Cys Ser Val Met
    195                 200                 205

His Glu Ala Leu His Asn His Tyr Thr Gln Lys Ser Leu Ser Leu Ser
210                 215                 220

Pro Gly Lys Gly Gly Gly Ser Gly Gly Gly Ser Gly Gly
225                 230                 235                 240

Gly Ser Gln Leu Tyr Ser Ala Leu Ala Asn Lys Cys Cys His Val Gly
            245                 250                 255

Cys Thr Lys Arg Ser Leu Ala Arg Phe Cys Gly Gly Gly Ser Gly
            260                 265                 270

Gly Gly Ser Gly Gly Gly Ser Ser Trp Met Glu Glu Val Ile
        275                 280                 285

Lys Leu Cys Gly Arg Glu Leu Val Arg Ala Gln Ile Ala Ile Cys Gly
    290                 295                 300

Met Ser Thr Trp Ser
305
```

<210> SEQ ID NO 17
<211> LENGTH: 930
<212> TYPE: DNA
<213> ORGANISM: Artificial Sequence
<220> FEATURE:
<223> OTHER INFORMATION: DNA encoding fusion protein

<400> SEQUENCE: 17

```
gataaaaccc atacctgccc gccgtgcccg gcgccggaat tgaaggcgg cccgagcgtg      60
tttctgtttc cgccgaaacc gaaagatacc ctgatgatta ccgcacccc ggaagtgacc     120
tgcgtggtgg tggatgtgag ccatgaagat ccggaagtga aatttaactg gtatgtggat     180
ggcgtggaag tgcataacgc gaaaaccaaa ccgcgcgaag aacagtataa cagcacctat     240
cgcgtggtga gcgtgctgac cgtgctgcat caggattggc tgaacggcaa agaatataaa     300
tgcaaagtga gcaacaaagc gctgccggcg agcattgaaa aaaccattag caaagcgaaa     360
ggccagccgc gcgaaccgca ggtgtatacc ctgccgccga ccgcgatga actgaccaaa     420
aaccaggtga gcctgacctg cctggtgaaa ggcttttatc cgagcgatat tgcggtggaa     480
tgggaaagca acggccagcc ggaaaacaac tataaaacca cccgccggt gctggatagc     540
gatggcagct ttttctgta tagcaaactg accgtggata aaagccgctg cagcagggc     600
aacgtgttta gctgcagcgt gatgcatgaa gcgctgcata accattatac ccagaaaagc     660
ctgagcctga gcccgggcaa aggcggcggc ggcagcggcg gcggcggcag cggcggcggc     720
ggcagccagc tgtatagcgc gctggcgaac aaatgctgcc atgtgggctg caccaaacgc     780
agcctggcgc gcttttgcgg cggcggcggc agcggcggcg gcggcagcgg cggcggcggc     840
agcagctgga tggaagaagt gattaaactg tgtggccgcg aactggtgcg cgcgcagatt     900
gcgatttgcg gcatgagcac ctggagctga                                      930
```

<210> SEQ ID NO 18
<211> LENGTH: 309
<212> TYPE: PRT
<213> ORGANISM: Artificial Sequence
<220> FEATURE:
<223> OTHER INFORMATION: fusion protein

<400> SEQUENCE: 18

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Gly Gly Ser Gly Gly Gly Ser Gly Gly Gly Gly Gly
225                 230                 235                 240

Gly Ser Gln Leu Tyr Ser Ala Leu Ala Asn Lys Cys Cys His Val Gly
                245                 250                 255

Cys Thr Lys Arg Ser Leu Ala Arg Phe Cys Gly Gly Gly Ser Gly
            260                 265                 270

Gly Gly Gly Ser Gly Gly Gly Gly Ser Ser Trp Met Glu Glu Val Ile
        275                 280                 285

Lys Leu Cys Gly Arg Glu Leu Val Arg Ala Gln Ile Ala Ile Cys Gly
290                 295                 300

Met Ser Thr Trp Ser
305

<210> SEQ ID NO 19
<211> LENGTH: 930
<212> TYPE: DNA
<213> ORGANISM: Artificial Sequence
<220> FEATURE:
<223> OTHER INFORMATION: DNA encoding fusion protein

<400> SEQUENCE: 19
gataaaaccc ataccctgccc gccgtgcccg cgccggaat tcagggcgg cccgagcgtg      60 tttctgtttc cgccgaaacc gaaagatacc ctgatgatta gccgcacccc ggaagtgacc    120
tgcgtggtgg tggatgtgag ccatgaagat ccggaagtga aatttaactg gtatgtggat    180

```
ggcgtggaag tgcataacgc gaaaaccaaa ccgcgcgaag aacagtataa cagcacctat      240
cgcgtggtga gcgtgctgac cgtgctgcat caggattggc tgaacggcaa agaatataaa      300
tgccaggtga gcaacaaagc gctgccggcg ccgattgaaa aaaccattag caaagcgaaa      360
ggccagccgc gcgaaccgca ggtgtatacc ctgccgccga ccgcgatga actgaccaaa       420 aaccaggtga gcctgacctg cctggtgaaa ggcttttatc cgagcgatat tgcggtggaa      480
tgggaaagca acggccagcc ggaaaacaac tataaaacca ccccgccggt gctggatagc      540
gatggcagct ttttctgtga tagcaaactg accgtggata aaagccgctg gcagcagggc      600
aacgtgttta gctgcagcgt gatgcatgaa gcgctgcata accattatac ccagaaaagc      660
ctgagcctga gcccgggcaa aggcggcggc ggcagcggcg gcggcggcag cggcggcggc      720
ggcagccagc tgtatagcgc gctggcgaac aaatgctgcc atgtgggctg caccaaacgc      780
agcctggcgc gcttttgcgg cggcggcggc agcggcggcg gcgcagcgg cggcggcggc        840 agcagctgga tggaagaagt gattaaactg tgtggccgcg aactggtgcg cgcgcagatt      900
gcgatttgcg gcatgagcac ctggagctga                                        930
```

<210> SEQ ID NO 20
<211> LENGTH: 310
<212> TYPE: PRT
<213> ORGANISM: Artificial Sequence
<220> FEATURE:
<223> OTHER INFORMATION: fusion protein

<400> SEQUENCE: 20

```
Asp Lys Thr His Thr Cys Pro Pro Cys Pro Ala Pro Glu Phe Gln Gln
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Gln Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ser Gly Gly Gly Gly Ser Gly Gly
```

```
225                 230                 235                 240
Gly Gly Ser Gln Leu Tyr Ser Ala Leu Ala Asn Lys Cys Cys His Val
                245                 250                 255
Gly Cys Thr Lys Arg Ser Leu Ala Arg Phe Cys Gly Gly Gly Gly Ser
            260                 265                 270
Gly Gly Gly Gly Ser Gly Gly Gly Ser Ser Trp Met Glu Glu Val
                275                 280                 285
Ile Lys Leu Cys Gly Arg Glu Leu Val Arg Ala Gln Ile Ala Ile Cys
        290                 295                 300
Gly Met Ser Thr Trp Ser
305                 310
```

<210> SEQ ID NO 21
<211> LENGTH: 933
<212> TYPE: DNA
<213> ORGANISM: Artificial Sequence
<220> FEATURE:
<223> OTHER INFORMATION: DNA encoding fusion protein

<400> SEQUENCE: 21

```
gataaaaccc atacctgccc gccgtgcccg gcgccggaac tgctgggcgg cccgagcgtg      60
tttctgtttc cgccgaaacc gaaagatacc ctgtatatta cccgcgaacc ggaagtgacc     120
tgcgtggtgg tggatgtgag ccatgaagat ccggaagtga aatttaactg gtatgtggat     180
ggcgtggaag tgcataacgc gaaaaccaaa ccgcgcgaag aacagtataa cagcacctat     240
cgcgtggtga gcgtgctgac cgtgctgcat caggattggc tgaacggcaa agaatataaa     300
tgcaaagtga gcaacaaagc gctgccggcg ccgattgaaa aaccattagc aaagcgaaa      360
ggccagccgc gcgaaccgca ggtgtatacc ctgccgccga ccgcgatgaa actgaccaaa     420
aaccaggtga gcctgacctg cctggtgaaa ggcttttatc cgagcgatat tgcggtggaa     480
tgggaaagca acggccagcc ggaaaacaac tataaaaccc cccgccggt gctggatagc     540
gatggcagct ttttctgta tagcaaactg accgtggata aaagccgctg cagcagggc      600
aacgtgttta gctgcagcgt gatgcatgaa gcgctgcata ccattatac ccagaaaagc     660
ctgagcctga gcccgggcaa aggcggcggc ggcagcggcg gcggcggcag cggcggcggc     720
ggcagccagc tgtatagcgc gctggcgaac aaatgctgcc atgtgggctg caccaaacgc     780
agcctggcgc gctttgcgg cggcggcggc agcggcggcg gcggcagcgg cggcggcggc     840
agcagctgga tggaagaagt gattaaactg tgtggccgcg aactggtgcg cgcgcagatt     900
gcgatttgcg gcatgagcac ctggagctga taa                                 933
```

<210> SEQ ID NO 22
<211> LENGTH: 309
<212> TYPE: PRT
<213> ORGANISM: Artificial Sequence
<220> FEATURE:
<223> OTHER INFORMATION: fusion protein

<400> SEQUENCE: 22

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Tyr
            20                  25                  30
Ile Thr Arg Glu Pro Glu Val Thr Cys Val Val Val Asp Val Ser His
        35                  40                  45
Glu Asp Pro Glu Val Lys Phe Asn Trp Tyr Val Asp Gly Val Glu Val
```

|  |  |  |  | 50 |  |  |  |  | 55 |  |  |  |  | 60 |  |

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Ser Gly Gly Gly Ser Gly Gly Gly
225                 230                 235                 240

Gly Ser Gln Leu Tyr Ser Ala Leu Ala Asn Lys Cys Cys His Val Gly
                245                 250                 255

Cys Thr Lys Arg Ser Leu Ala Arg Phe Cys Gly Gly Gly Ser Gly
            260                 265                 270

Gly Gly Gly Ser Gly Gly Gly Gly Ser Ser Trp Met Glu Glu Val Ile
        275                 280                 285

Lys Leu Cys Gly Arg Glu Leu Val Arg Ala Gln Ile Ala Ile Cys Gly
    290                 295                 300

Met Ser Thr Trp Ser
305

<210> SEQ ID NO 23
<211> LENGTH: 930
<212> TYPE: DNA
<213> ORGANISM: Artificial Sequence
<220> FEATURE:
<223> OTHER INFORMATION: DNA encoding fusion protein

<400> SEQUENCE: 23
gataaaaccc atacctgccc gccgtgcccg gcgccggaat tgaaggcgg cccgagcgtg    60 tttctgtttc cgccgaaacc gaaagatacc ctgtatatta cccgcgaacc ggaagtgacc   120
tgcgtggtgg tggatgtgag ccatgaagat ccggaagtga aatttaactg gtatgtggat   180
ggcgtggaag tgcataacgc gaaaaccaaa ccgcgcgaag aacagtataa cagcacctat   240
cgcgtggtga gcgtgctgac cgtgctgcat caggattggc tgaacggcaa agaatataaa   300
tgcaaagtga gcaacaaagc gctgccggcg agcattgaaa aaaccattag caaagcgaaa   360
ggccagccgc gcgaaccgca ggtgtatacc ctgccgccga gcgcgatga actgaccaaa   420 aaccaggtga gcctgacctg cctggtgaaa ggctttatc cgagcgatat tgcggtggaa   480
tgggaaagca cggcagcc ggaaaacaac tataaaacca cccgccggt gctggatagc   540 gatggcagct ttttctgta tagcaaactg accgtggata aaagccgctg gcagcagggc   600

```
aacgtgttta gctgcagcgt gatgcatgaa gcgctgcata accattatac ccagaaaagc    660
ctgagcctga gcccgggcaa aggcggcggc ggcagcggcg gcggcggcag cggcggcggc    720
ggcagccagc tgtatagcgc gctggcgaac aaatgctgcc atgtgggctg caccaaacgc    780
agcctggcgc gcttttgcgg cggcggcggc agcggcggcg gcggcagcgg cggcggcggc    840
agcagctgga tggaagaagt gattaaactg tgtggccgcg aactggtgcg cgcgcagatt    900
gcgatttgcg gcatgagcac ctggagctga                                    930
```

```
<210> SEQ ID NO 24
<211> LENGTH: 309
<212> TYPE: PRT
<213> ORGANISM: Artificial Sequence
<220> FEATURE:
<223> OTHER INFORMATION: fusion protein

<400> SEQUENCE: 24
```

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Ser Gly Gly Gly Gly
225                 230                 235                 240

Gly Ser Gln Leu Tyr Ser Ala Leu Ala Asn Lys Cys Cys His Val Gly
                245                 250                 255

Cys Thr Lys Arg Ser Leu Ala Arg Phe Cys Gly Gly Gly Ser Gly
            260                 265                 270

Gly Gly Gly Ser Gly Gly Gly Gly Ser Ser Trp Met Glu Glu Val Ile
        275                 280                 285

Lys Leu Cys Gly Arg Glu Leu Val Arg Ala Gln Ile Ala Ile Cys Gly
    290                 295                 300

Met Ser Thr Trp Ser
305

<210> SEQ ID NO 25
<211> LENGTH: 933
<212> TYPE: DNA
<213> ORGANISM: Artificial Sequence
<220> FEATURE:
<223> OTHER INFORMATION: DNA encoding fusion protein

<400> SEQUENCE: 25

| | |
|---|---|
| gataaaaccc atacctgccc gccgtgcccg gcgccggaat tcagggcgg cccgagcgtg | 60 |
| tttctgtttc cgccgaaacc gaaagatacc ctgtatatta cccgcgaacc ggaagtgacc | 120 |
| tgcgtggtgg tggatgtgag ccatgaagat ccggaagtga aatttaactg gtatgtggat | 180 |
| ggcgtggaag tgcataacgc gaaaaccaaa ccgcgcgaag aacagtataa cagcacctat | 240 |
| cgcgtggtga gcgtgctgac cgtgctgcat caggattggc tgaacggcaa agaatataaa | 300 |
| tgccaggtga gcaacaaagc gctgccggcg ccgattgaaa aaaccattag caaagcgaaa | 360 |
| ggccagccgc gcgaaccgca ggtgtatacc ctgccgccga ccgcgatga actgaccaaa | 420 |
| aaccaggtga gcctgacctg cctggtgaaa ggctttttatc cgagcgatat tgcggtggaa | 480 |
| tgggaaagca cggccagcc ggaaaacaac tataaaacca ccccgccggt gctggatagc | 540 |
| gatggcagct ttttctgta tagcaaactg accgtggata aaagccgctg gcagcagggc | 600 |
| aacgtgttta gctgcagcgt gatgcatgaa gcgctgcata accattatac ccagaaaagc | 660 |
| ctgagcctga gccccgggcaa aggcggcggc ggcagcggcg gcggcggcag cggcggcggc | 720 |
| ggcagccagc tgtatagcgc gctggcgaac aaatgctgcc atgtgggctg caccaaacgc | 780 |
| agcctggcgc gcttttgcgg cggcggcggc agcggcggcg gcggcagcgg cggcggcggc | 840 |
| agcagctgga tggaagaagt gattaaactg tgtggccgcg aactggtgcg cgcgcagatt | 900 |
| gcgatttgcg gcatgagcac ctggagctga taa | 933 |

<210> SEQ ID NO 26
<211> LENGTH: 309
<212> TYPE: PRT
<213> ORGANISM: Artificial Sequence
<220> FEATURE:
<223> OTHER INFORMATION: fusion protein

<400> SEQUENCE: 26

Asp Lys Thr His Thr Cys Pro Pro Cys Pro Ala Pro Glu Phe Gln Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

```
Tyr Thr Leu Pro Pro Ser Arg Asp Glu Leu Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
210                 215                 220
Pro Gly Lys Gly Gly Gly Ser Gly Gly Gly Ser Gly Gly Gly
225                 230                 235                 240
Gly Ser Gln Leu Tyr Ser Ala Leu Ala Asn Lys Cys Cys His Val Gly
                245                 250                 255
Cys Thr Lys Arg Ser Leu Ala Arg Phe Cys Gly Gly Gly Ser Gly
                260                 265                 270
Gly Gly Gly Ser Gly Gly Gly Gly Ser Ser Trp Met Glu Glu Val Ile
            275                 280                 285
Lys Leu Cys Gly Arg Glu Leu Val Arg Ala Gln Ile Ala Ile Cys Gly
290                 295                 300
Met Ser Thr Trp Ser
305
```

<210> SEQ ID NO 27
<211> LENGTH: 936
<212> TYPE: DNA
<213> ORGANISM: Artificial Sequence
<220> FEATURE:
<223> OTHER INFORMATION: DNA encoding fusion protein

<400> SEQUENCE: 27

```
gaatctaagt acggccctcc ctgcccaccc tgccctgccc ctgaatttct gggcggaccc      60
tccgtgttcc tgttcccacc caagcccaag gacaccctga tgatcagccg gacccctgaa     120
gtgacctgcg tggtggtgga cgtgtcccag gaagatcccg aggtccagtt caattggtac     180
gtggacggcg tggaagtgca caacgccaag accaagccca gaggaacag gttcaacagc     240
acctaccggg tggtgtccgt gctgaccgtg ctgcaccagg actggctgaa cggcaaagag     300
tacaagtgca aggtgtccaa caagggcctg cccagctcca tcgagaaaac catcagcaag     360
gccaagggcc agccccgcga gccccaggtc tacacactgc ctcccagcca ggaagagatg     420
accaagaacc aggtgtccct gacctgtctg gtgaaaggct cctacccag cgatatcgcc     480
gtggaatggg agagcaacgg ccagcccgag aacaactaca agaccacccc tcccgtgctg     540
gacagcgacg gcagcttctt tctgtactcc cggctgaccg tggacaagag ccggtggcag     600
gaaggcaacg tcttcagctg cagcgtgatg cacgaggccc tgcacaacca ctacacccag     660
aagtccctga gcctgagcct gggcaagggc ggcggcggca gcggcggcgg cggcagcggc     720
ggcggcggca gccagctgta tagcgcgctg gcgaacaaat gctgccatgt gggctgcacc     780
aaacgcagcc tggcgcgctt tgcggcggc ggcggcagcg gcggcggcgg cagcggcggc     840
ggcggcagca gctggatgga agaagtgatt aaactgtgtg gccgcgaact ggtgcgcgcg     900
cagattgcga tttgcggcat gagcacctgg agctga                                936
```

<210> SEQ ID NO 28
<211> LENGTH: 311
<212> TYPE: PRT
<213> ORGANISM: Artificial Sequence
<220> FEATURE:
<223> OTHER INFORMATION: fusion protein

<400> SEQUENCE: 28

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Gly Gly Gly Ser Gly Gly Gly Ser Gly
225                 230                 235                 240

Gly Gly Gly Ser Gln Leu Tyr Ser Ala Leu Ala Asn Lys Cys Cys His
                245                 250                 255

Val Gly Cys Thr Lys Arg Ser Leu Ala Arg Phe Cys Gly Gly Gly
            260                 265                 270

Ser Gly Gly Gly Ser Gly Gly Gly Ser Ser Trp Met Glu Glu
        275                 280                 285

Val Ile Lys Leu Cys Gly Arg Glu Leu Val Arg Ala Gln Ile Ala Ile
    290                 295                 300

Cys Gly Met Ser Thr Trp Ser
305                 310
```

<210> SEQ ID NO 29
<211> LENGTH: 681
<212> TYPE: DNA
<213> ORGANISM: Artificial Sequence
<220> FEATURE:
<223> OTHER INFORMATION: Fc-TM

<400> SEQUENCE: 29

```
gataaaaccc atacctgccc gccgtgcccg gcgccggaat ttgaaggcgg cccgagcgtg      60
tttctgtttc cgccgaaacc gaaagatacc ctgatgatta gccgcacccc ggaagtgacc     120
tgcgtggtgg tggatgtgag ccatgaagat ccggaagtga aatttaactg gtatgtggat     180
ggcgtggaag tgcataacgc gaaaaccaaa ccgcgcgaag aacagtataa cagcacctat     240
cgcgtggtga gcgtgctgac cgtgctgcat caggattggc tgaacggcaa agaatataaa     300
tgcaaagtga gcaacaaagc gctgccggcg agcattgaaa aaaccattag caaagcgaaa     360
ggccagccgc gcgaaccgca ggtgtatacc ctgccgccga gccgcgatga actgaccaaa     420
aaccaggtga gcctgacctg cctggtgaaa ggctttttatc cgagcgatat tgcggtggaa     480
tgggaaagca acggccagcc ggaaaacaac tataaaacca ccccgccggt gctggatagc     540
gatggcagct ttttctgtta tagcaaactg accgtggata aaagccgctg cagcagggc      600 aacgtgttta gctgcagcgt gatgcatgaa gcgctgcata accattatac ccagaaaagc     660
ctgagcctga gcccgggcaa a                                                681
```

<210> SEQ ID NO 30
<211> LENGTH: 227
<212> TYPE: PRT
<213> ORGANISM: Artificial Sequence
<220> FEATURE:
<223> OTHER INFORMATION: Fc-TM

<400> SEQUENCE: 30

```
Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 31
<211> LENGTH: 681
<212> TYPE: DNA
<213> ORGANISM: Artificial Sequence
<220> FEATURE:
<223> OTHER INFORMATION: Fc-FQQ

<400> SEQUENCE: 31

```
gataaaaccc atacctgccc gccgtgcccg gcgccggaat tcagggcgg cccgagcgtg      60
tttctgtttc cgccgaaacc gaaagatacc ctgatgatta ccgcacccc ggaagtgacc     120
tgcgtggtgg tggatgtgag ccatgaagat ccggaagtga aatttaactg gtatgtggat    180
ggcgtggaag tgcataacgc gaaaaccaaa ccgcgcgaag aacagtataa cagcacctat    240
cgcgtggtga gcgtgctgac cgtgctgcat caggattggc tgaacggcaa agaatataaa    300
tgccaggtga gcaacaaagc gctgccggcg ccgattgaaa aaaccattag caaagcgaaa    360
ggccagccgc gcgaaccgca ggtgtatacc ctgccgccga ccgcgatga actgaccaaa    420
aaccaggtga gcctgacctg cctggtgaaa ggctttatc cgagcgatat tgcggtggaa    480
tgggaaagca acggccagcc ggaaaacaac tataaaacca cccgccggt gctggatagc    540
gatggcagct ttttctgta tagcaaactg accgtggata aaagccgctg cagcagggc    600
aacgtgttta gctgcagcgt gatgcatgaa gcgctgcata accattatac ccagaaaagc    660
ctgagcctga gcccgggcaa a                                             681
```

<210> SEQ ID NO 32
<211> LENGTH: 228
<212> TYPE: PRT
<213> ORGANISM: Artificial Sequence
<220> FEATURE:
<223> OTHER INFORMATION: Fc-FQQ

<400> SEQUENCE: 32

```
Asp Lys Thr His Thr Cys Pro Pro Cys Pro Ala Pro Glu Phe Gln Gln
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Gln Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
```

```
                  180                 185                 190
Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
210                 215                 220

Ser Pro Gly Lys
225

<210> SEQ ID NO 33
<211> LENGTH: 681
<212> TYPE: DNA
<213> ORGANISM: Artificial Sequence
<220> FEATURE:
<223> OTHER INFORMATION: Fc-YTE

<400> SEQUENCE: 33
gataaaaccc atacctgccc gccgtgcccg gcgccggaac tgctgggcgg cccgagcgtg    60
tttctgtttc cgccgaaacc gaaagatacc ctgtatatta cccgcgaacc ggaagtgacc   120
tgcgtggtgg tggatgtgag ccatgaagat ccggaagtga aatttaactg gtatgtggat   180
ggcgtggaag tgcataacgc gaaaaccaaa ccgcgcgaag aacagtataa cagcacctat   240
cgcgtggtga gcgtgctgac cgtgctgcat caggattggc tgaacggcaa agaatataaa   300
tgcaaagtga gcaacaaagc gctgccggcg ccgattgaaa aaaccattag caaagcgaaa   360
ggccagccgc gcgaaccgca ggtgtatacc ctgccgccga gccgcgatga actgaccaaa   420
aaccaggtga gcctgacctg cctggtgaaa ggcttttatc cgagcgatat tgcggtggaa   480
tgggaaagca cggccagcc ggaaaacaac tataaaacca ccccgccggt gctggatagc   540
gatggcagct ttttcctgta tagcaaactg accgtggata aaagccgctg gcagcagggc   600
aacgtgttta gctgcagcgt gatgcatgaa gcgctgcata accattatac ccagaaaagc   660
ctgagcctga gcccgggcaa a                                             681

<210> SEQ ID NO 34
<211> LENGTH: 227
<212> TYPE: PRT
<213> ORGANISM: Artificial Sequence
<220> FEATURE:
<223> OTHER INFORMATION: Fc-YTE

<400> SEQUENCE: 34

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

-continued

```
Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 35
<211> LENGTH: 681
<212> TYPE: DNA
<213> ORGANISM: Artificial Sequence
<220> FEATURE:
<223> OTHER INFORMATION: Fc-YTE-TM

<400> SEQUENCE: 35
gataaaaccc atacctgccc gccgtgcccg gcgccggaat ttgaaggcgg cccgagcgtg      60
tttctgtttc cgccgaaacc gaaagatacc ctgtatatta cccgcgaacc ggaagtgacc     120
tgcgtggtgg tggatgtgag ccatgaagat ccggaagtga aatttaactg gtatgtggat     180
ggcgtggaag tgcataacgc gaaaaccaaa ccgcgcgaag aacagtataa cagcacctat     240
cgcgtggtga gcgtgctgac cgtgctgcat caggattggc tgaacggcaa agaatataaa     300
tgcaaagtga gcaacaaagc gctgccggcg agcattgaaa aaaccattag caaagcgaaa     360
ggccagccgc gcgaaccgca ggtgtatacc ctgccgccga ccgcgatgaa actgaccaaa     420
aaccaggtga gcctgacctg cctggtgaaa ggcttttatc cgagcgatat tgcggtggaa     480
tgggaaagca acggccagcc ggaaaacaac tataaaacca cccgccggt gctggatagc     540 gatggcagct ttttctgta tagcaaactg accgtggata aaagccgctg gcagcagggc     600
aacgtgttta gctgcagcgt gatgcatgaa gcgctgcata accattatac ccagaaaagc     660
ctgagcctga gcccgggcaa a                                              681

<210> SEQ ID NO 36
<211> LENGTH: 227
<212> TYPE: PRT
<213> ORGANISM: Artificial Sequence
<220> FEATURE:
<223> OTHER INFORMATION: Fc-YTE-TM

<400> SEQUENCE: 36

Asp Lys Thr His Thr Cys Pro Pro Cys Pro Ala Pro Glu Phe Glu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 37
<211> LENGTH: 681
<212> TYPE: DNA
<213> ORGANISM: Artificial Sequence
<220> FEATURE:
<223> OTHER INFORMATION: Fc-YTE-FQQ

<400> SEQUENCE: 37
gataaaaccc atacctgccc gccgtgcccg gcgccggaat tcagggcgg cccgagcgtg      60 tttctgtttc cgccgaaacc gaaagatacc ctgtatatta cccgcgaacc ggaagtgacc    120
tgcgtggtgg tggatgtgag ccatgaagat ccggaagtga aatttaactg gtatgtggat    180
ggcgtggaag tgcataacgc gaaaaccaaa ccgcgcgaag aacagtataa cagcacctat    240
cgcgtggtga gcgtgctgac cgtgctgcat caggattggc tgaacggcaa agaatataaa    300
tgccaggtga gcaacaaagc gctgccggcg ccgattgaaa aaaccattag caaagcgaaa    360
ggccagccgc gcgaaccgca ggtgtatacc ctgccgccga ccgcgatga actgaccaaa    420 aaccaggtga gcctgacctg cctggtgaaa ggcttttatc cgagcgatat tgcggtggaa    480
tgggaaagca cggccagcc ggaaacaac tataaaacca ccccgccggt gctggatagc    540
gatggcagct tttttctgta tagcaaactg accgtggata aagccgctg gcagcagggc    600 aacgtgttta gctgcagcgt gatgcatgaa gcgctgcata accattatac ccagaaaagc    660
ctgagcctga gcccgggcaa a                                              681

<210> SEQ ID NO 38
<211> LENGTH: 227
<212> TYPE: PRT
<213> ORGANISM: Artificial Sequence
<220> FEATURE:
<223> OTHER INFORMATION: Fc-YTE-FQQ

<400> SEQUENCE: 38

Asp Lys Thr His Thr Cys Pro Pro Cys Pro Ala Pro Glu Phe Gln Gly
1               5                   10                  15

Gly Pro Ser Val Phe Leu Phe Pro Pro Lys Pro Lys Asp Thr Leu Tyr

```
                    20                  25                  30
Ile Thr Arg Glu Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 39
<211> LENGTH: 687
<212> TYPE: DNA
<213> ORGANISM: Artificial Sequence
<220> FEATURE:
<223> OTHER INFORMATION: Fc-G4P

<400> SEQUENCE: 39
gaatctaagt acggccctcc ctgcccaccc tgccctgccc ctgaatttct gggcggaccc      60
tccgtgttcc tgttcccacc caagcccaag gacaccctga tgatcagccg gacccctgaa     120
gtgacctgcg tggtggtgga cgtgtcccag gaagatcccg aggtccagtt caattggtac     180
gtggacggcg tggaagtgca caacgccaag accaagccca gagaggaaca gttcaacagc     240
acctaccggg tggtgtccgt gctgaccgtg ctgcaccagg actggctgaa cggcaaagag     300
tacaagtgca aggtgtccaa caagggcctg cccagctcca tcgagaaaac catcagcaag     360
gccaagggcc agccccgcga gccccaggtc tacacactgc ctcccagcca ggaagagatg     420
accaagaacc aggtgtccct gacctgtctg gtgaaaggct tctacccag cgatatcgcc      480 gtggaatggg agagcaacgg ccagcccgag aacaactaca agaccacccc tcccgtgctg     540
gacagcgacg gcagcttctt tctgtactcc cggctgaccg tggacaagag ccggtggcag     600
gaaggcaacg tcttcagctg cagcgtgatg cacgaggccc tgcacaacca ctacacccag     660
aagtccctga gcctgagcct gggcaag                                         687

<210> SEQ ID NO 40
<211> LENGTH: 229
<212> TYPE: PRT
```

<213> ORGANISM: Artificial Sequence
<220> FEATURE:
<223> OTHER INFORMATION: Fc-G4P

<400> SEQUENCE: 40

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 41
<211> LENGTH: 72
<212> TYPE: DNA
<213> ORGANISM: Homo sapiens

<400> SEQUENCE: 41
cagctgtata gcgcgctggc gaacaaatgc tgccatgtgg gctgcaccaa acgcagcctg        60
gcgcgctttt gc                                                           72

<210> SEQ ID NO 42
<211> LENGTH: 24
<212> TYPE: PRT
<213> ORGANISM: Homo sapiens

<400> SEQUENCE: 42

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 43

```
<211> LENGTH: 90
<212> TYPE: DNA
<213> ORGANISM: Homo sapiens

<400> SEQUENCE: 43
gacagctgga tggaagaagt gattaaactg tgtggccgcg aactggtgcg cgcgcagatt    60
gcgatttgcg gcatgagcac ctggagctga                                    90

<210> SEQ ID NO 44
<211> LENGTH: 29
<212> TYPE: PRT
<213> ORGANISM: Homo sapiens

<400> SEQUENCE: 44

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 45
<211> LENGTH: 87
<212> TYPE: DNA
<213> ORGANISM: Artificial Sequence
<220> FEATURE:
<223> OTHER INFORMATION: Human Relaxin 2 chain B variant

<400> SEQUENCE: 45
agctggatgg aagaagtgat taaactgtgt ggccgcgaac tggtgcgcgc gcagattgcg    60
atttgcggca tgagcacctg gagctga                                       87

<210> SEQ ID NO 46
<211> LENGTH: 28
<212> TYPE: PRT
<213> ORGANISM: Artificial Sequence
<220> FEATURE:
<223> OTHER INFORMATION: Human Relaxin 2 chain B variant

<400> SEQUENCE: 46

Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser
            20                  25

<210> SEQ ID NO 47
<211> LENGTH: 306
<212> TYPE: DNA
<213> ORGANISM: Homo sapiens

<400> SEQUENCE: 47
tctttgtctc aagaggatgc tccacagaca cccagaccag tggccgagat tgtccccagc    60
tttataaaca agacactga gaccataaac atgatgtccg aattcgtcgc aaatctgcct    120
caggagctta agctcactct ctctgagatg caaccagcac tgcctcagct gcagcagcac    180
gtccctgtgc tgaaggactc cagcctgttg tttgaagaat taaaaaaact tattcgcaac    240
cgccagtccg aggccgctga ctcaagcccc tcagagctga agtacctggg actggacact    300
cacagt                                                              306

<210> SEQ ID NO 48
<211> LENGTH: 102
<212> TYPE: PRT
<213> ORGANISM: Homo sapiens
```

<400> SEQUENCE: 48

Ser Leu Ser Gln Glu Asp Ala Pro Gln Thr Pro Arg Pro Val Ala Glu
1               5                   10                  15

Ile Val Pro Ser Phe Ile Asn Lys Asp Thr Glu Thr Ile Asn Met Met
            20                  25                  30

Ser Glu Phe Val Ala Asn Leu Pro Gln Glu Leu Lys Leu Thr Leu Ser
        35                  40                  45

Glu Met Gln Pro Ala Leu Pro Gln Leu Gln Gln His Val Pro Val Leu
    50                  55                  60

Lys Asp Ser Ser Leu Leu Phe Glu Glu Phe Lys Lys Leu Ile Arg Asn
65                  70                  75                  80

Arg Gln Ser Glu Ala Ala Asp Ser Ser Pro Ser Glu Leu Lys Tyr Leu
                85                  90                  95

Gly Leu Asp Thr His Ser
            100

<210> SEQ ID NO 49
<211> LENGTH: 72
<212> TYPE: DNA
<213> ORGANISM: Homo sapiens

<400> SEQUENCE: 49
gatgtcctgg ctggcctttc cagcagctgc tgcaagtggg ggtgtagcaa aagtgaaatc      60
agtagccttt gc                                                         72

<210> SEQ ID NO 50
<211> LENGTH: 24
<212> TYPE: PRT
<213> ORGANISM: Homo sapiens

<400> SEQUENCE: 50

Asp Val Leu Ala Gly Leu Ser Ser Ser Cys Cys Lys Trp Gly Cys Ser
1               5                   10                  15

Lys Ser Glu Ile Ser Ser Leu Cys
            20

<210> SEQ ID NO 51
<211> LENGTH: 81
<212> TYPE: DNA
<213> ORGANISM: Homo sapiens

<400> SEQUENCE: 51
cgggcagcgc cttacggggt caggctttgc ggccgagaat tcatccgagc agtcatcttc      60
acctgcgggg gctcccggtg g                                               81

<210> SEQ ID NO 52
<211> LENGTH: 27
<212> TYPE: PRT
<213> ORGANISM: Homo sapiens

<400> SEQUENCE: 52

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp
            20                  25

<210> SEQ ID NO 53
<211> LENGTH: 192

<212> TYPE: DNA
<213> ORGANISM: Homo sapiens

<400> SEQUENCE: 53
tcagacatcc tggcccacga ggctatggga gatacctcc cggatgcaga tgctgatgaa    60
gacagtctgg caggcgagct ggatgaggcc atggggtcca gcgagtggct ggccctgacc   120
aagtcacccc aggccttta caggggggcga cccagctggc aaggaaccc tgggggttctt   180 cggggcagcc ga                                                       192

<210> SEQ ID NO 54
<211> LENGTH: 64
<212> TYPE: PRT
<213> ORGANISM: Homo sapiens

<400> SEQUENCE: 54

Ser Asp Ile Leu Ala His Glu Ala Met Gly Asp Thr Phe Pro Asp Ala
1               5                   10                  15

Asp Ala Asp Glu Asp Ser Leu Ala Gly Glu Leu Asp Glu Ala Met Gly
            20                  25                  30

Ser Ser Glu Trp Leu Ala Leu Thr Lys Ser Pro Gln Ala Phe Tyr Arg
        35                  40                  45

Gly Arg Pro Ser Trp Gln Gly Thr Pro Gly Val Leu Arg Gly Ser Arg
    50                  55                  60

<210> SEQ ID NO 55
<211> LENGTH: 8
<212> TYPE: PRT
<213> ORGANISM: Artificial Sequence
<220> FEATURE:
<223> OTHER INFORMATION: conserved motif
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 55

Arg Xaa Xaa Xaa Arg Xaa Xaa Ile
1               5

<210> SEQ ID NO 56
<211> LENGTH: 4
<212> TYPE: PRT
<213> ORGANISM: Artificial Sequence
<220> FEATURE:
<223> OTHER INFORMATION: connector

<400> SEQUENCE: 56

Gly Gly Ser Pro
1

<210> SEQ ID NO 57
<211> LENGTH: 15
<212> TYPE: PRT
<213> ORGANISM: Artificial Sequence
<220> FEATURE:
<223> OTHER INFORMATION: connector or linker

<400> SEQUENCE: 57

Gly Gly Gly Gly Ser Gly Gly Gly Ser Gly Gly Gly Gly Ser
1               5                   10                  15

<210> SEQ ID NO 58
<211> LENGTH: 5
<212> TYPE: PRT
<213> ORGANISM: Artificial Sequence
<220> FEATURE:
<223> OTHER INFORMATION: linker

<400> SEQUENCE: 58

Gly Gly Gly Gly Ser
1               5

<210> SEQ ID NO 59
<211> LENGTH: 27
<212> TYPE: PRT
<213> ORGANISM: Artificial Sequence
<220> FEATURE:
<223> OTHER INFORMATION: linker

<400> SEQUENCE: 59

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 60
<211> LENGTH: 8
<212> TYPE: PRT
<213> ORGANISM: Artificial Sequence
<220> FEATURE:
<223> OTHER INFORMATION: conserved motif 2
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 60

Arg Xaa Xaa Xaa Arg Xaa Xaa Val
1               5

<210> SEQ ID NO 61
<211> LENGTH: 942
<212> TYPE: DNA
<213> ORGANISM: Artificial Sequence
<220> FEATURE:
<223> OTHER INFORMATION: DNA encoding fusion protein

<400> SEQUENCE: 61
ggaggtggaa gcgcttgtcc tccatgcccg gcgcctgagt tcgagggcgg accctccgtg      60
ttcctgttcc ccccaaagcc caaggacacc ctgatgatct cccggacccc cgaagtgacc     120
tgcgtggtgg tggacgtgtc ccacgaggac cctgaagtga agttcaattg gtacgtggac     180
ggcgtggaag tgcacaacgc caagaccaag cccagagagg aacagtacaa ctccacctac     240
cgggtggtgt ccgtgctgac cgtgctgcac caggactggc tgaacggcaa agagtacaag     300
tgcaaggtct ccaacaaggc cctgcccgcc tccatcgaaa agaccatctc caaggccaag     360
ggccagcccc gcgagcctca ggtgtacaca ctgcccccca gcggggaaga gatgaccaag     420
aaccaggtgt ccctgacctg tctggtgaaa ggcttctacc cctccgatat cgctgtggaa     480
tgggagtcca acggccagcc cgagaacaac tacaagacca cccccctgt gctggactcc     540

```
gacggctcat tcttcctgta ctccaagctg accgtggaca agtcccggtg gcagcagggc    600
aacgtgttct cctgctccgt gatgcacgag gccctgcaca accactacac ccagaagtct    660
ctaagcttga gccccggcgg aggtggtgga agcggaggag gtggctctgg aggggggtgga   720 agcggaggtg gaggtggatc ccagctgtat agcgcgctgg cgaacaaatg ctgccatgtg    780
ggctgcacca acgcagcct ggcgcgcttt tgcggcggcg gcggcagcgg cggcggcggc    840
agcggcggcg gcggcagcag ctggatggaa gaagtgatta aactgtgtgg ccgcgaactg    900
gtgcgcgcgc agattgcgat tgcggcatg agcacctgga gc                       942
```

<210> SEQ ID NO 62
<211> LENGTH: 314
<212> TYPE: PRT
<213> ORGANISM: Artificial Sequence
<220> FEATURE:
<223> OTHER INFORMATION: fusion protein

<400> SEQUENCE: 62

```
Gly Gly Gly Ser Ala Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Gly Gly Gly Gly Ser Gln Leu Tyr Ser Ala Leu Ala Asn Lys
            245                 250                 255

Cys Cys His Val Gly Cys Thr Lys Arg Ser Leu Ala Arg Phe Cys Gly
        260                 265                 270

Gly Gly Gly Ser Gly Gly Gly Gly Ser Gly Gly Gly Ser Ser Trp
    275                 280                 285

Met Glu Glu Val Ile Lys Leu Cys Gly Arg Glu Leu Val Arg Ala Gln
```

Ile Ala Ile Cys Gly Met Ser Thr Trp Ser
305                 310

<210> SEQ ID NO 63
<211> LENGTH: 942
<212> TYPE: DNA
<213> ORGANISM: Artificial Sequence
<220> FEATURE:
<223> OTHER INFORMATION: DNA encoding fusion protein

<400> SEQUENCE: 63

```
ggaggtggaa gcgcttgtcc tccatgcccg gcgcctgagt tcgagggcgg accctccgtg      60
ttcctgttcc ccccaaagcc caaggacacc ctgatgatct cccggacccc cgaagtgacc     120
tgcgtggtgg tggacgtgtc ccacgaggac cctgaagtga agttcaattg gtacgtggac     180
ggcgtggaag tgcacaacgc caagaccaag cccagagagg aacagtacaa ctccacctac     240
cgggtggtgt ccgtgctgac cgtgctgcac caggactggc tgaacggcaa agagtacaag     300
tgcaaggtct ccaacaaggc cctgcccgcc tccatcgaaa agaccatctc caaggccaag     360
ggccagcccc gcgagcctca ggtgtacaca ctgcccccca gccgggaaga tgaccaag      420
aaccaggtgt ccctgacctg tctggtgaaa ggcttctacc cctccgatat cgctgtggaa     480
tgggagtcca acggccagcc cgagaacaac tacaagacca cccccctgt gctggactcc     540
gacggctcat tcttcctgta ctccaagctg accgtggaca agtcccggtg cagcagggc      600
aacgtgttct cctgctccgt gatgcacgag gccctgcaca accactacac ccagaagtct     660
ctaagcttga gccccggcgg aggtggtgga agcggaggag gtggctctgg agggggtgga     720
agcggaggtg gaggtggatc ctcctggatg gaggaggtta tcaagctgtg tggacgcgaa     780
ctggtgcgcg ctcagatcgc gatatgcggg atgtccacat ggtcaggcgg cggaggcagc     840
ggcggtggcg gcagcggcgg gggaggttct cagctctact cagcgctcgc taataagtgt     900
tgtcatgtgg gatgcacaaa gcggtctctc gccagattct gc                        942
```

<210> SEQ ID NO 64
<211> LENGTH: 314
<212> TYPE: PRT
<213> ORGANISM: Artificial Sequence
<220> FEATURE:
<223> OTHER INFORMATION: fusion protein

<400> SEQUENCE: 64

Gly Gly Gly Ser Ala Cys Pro Pro Cys Pro Ala Pro Glu Phe Glu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val

|   |   | 115 |   |   |   | 120 |   |   |   | 125 |   |
|---|---|---|---|---|---|---|---|---|---|---|---|

Tyr Thr Leu Pro Pro Ser Arg Glu Glu Met Thr Lys Asn Gln Val Ser
    130                  135                  140

Leu Thr Cys Leu Val Lys Gly Phe Tyr Pro Ser Asp Ile Ala Val Glu
145                 150                  155                  160

Trp Glu Ser Asn Gly Gln Pro Glu Asn Asn Tyr Lys Thr Thr Pro Pro
                165                  170                  175

Val Leu Asp Ser Asp Gly Ser Phe Phe Leu Tyr Ser Lys Leu Thr Val
            180                  185                  190

Asp Lys Ser Arg Trp Gln Gln Gly Asn Val Phe Ser Cys Ser Val Met
        195                  200                  205

His Glu Ala Leu His Asn His Tyr Thr Gln Lys Ser Leu Ser Leu Ser
    210                  215                  220

Pro Gly Gly Gly Gly Ser Gly Gly Gly Ser Gly Gly Gly Gly
225                 230                  235                  240

Ser Gly Gly Gly Gly Ser Ser Trp Met Glu Glu Val Ile Lys Leu
            245                  250                  255

Cys Gly Arg Glu Leu Val Arg Ala Gln Ile Ala Ile Cys Gly Met Ser
        260                  265                  270

Thr Trp Ser Gly Gly Gly Ser Gly Gly Gly Ser Gly Gly Gly
        275                  280                  285

Gly Ser Gln Leu Tyr Ser Ala Leu Ala Asn Lys Cys Cys His Val Gly
    290                  295                  300

Cys Thr Lys Arg Ser Leu Ala Arg Phe Cys
305                 310

<210> SEQ ID NO 65
<211> LENGTH: 936
<212> TYPE: DNA
<213> ORGANISM: Artificial Sequence
<220> FEATURE:
<223> OTHER INFORMATION: DNA encoding fusion protein

<400> SEQUENCE: 65

```
cagctgtata gcgcgctggc gaacaaatgc tgccatgtgg gctgcaccaa acgcagcctg      60
gcgcgctttt gcggcggcgg cggcagcggc ggcggcggca gcggcggcgg cggcagcagc     120
tggatggaag aagtgattaa actgtgtggc cgcgaactgg tgcgcgcgca gattgcgatt     180
tgcggcatga gcacctggag cgcggccgcg gtggaggtga tccggagg aggtggaagc      240
ggaggaggtg gaagcggagg aggtggaagc gcttgtcctc catgcccggc gcctgagttc     300
gagggcggac cctccgtgtt cctgttcccc ccaaagccca aggacaccct gatgatctcc     360
cggacccccg aagtgacctg cgtggtggtg gacgtgtccc acgaggaccc tgaagtgaag     420
ttcaattggt acgtggacgg cgtggaagtg cacaacgcca agaccaagcc agagaggaa      480
cagtacaact ccacctaccg ggtggtgtcc gtgctgaccg tgctgcacca ggactggctg     540
aacggcaaag agtacaagtg caaggtctcc aacaaggccc tgcccgcctc atcgaaaaag     600
accatctcca aggccaaggg ccagccccgc gagcctcagg tgtacacact gccccccagc     660
cgggaagaga tgaccaagaa ccaggtgtcc ctgacctgtc tggtgaaagg cttctacccc     720
tccgatatcg ctgtggaatg ggagtccaac ggccagcccg agaacaacta caagaccacc     780
cccctgtgc tggactccga cggctcattc ttcctgtact ccaagctgac cgtggacaag     840
tcccggtgga gcagggcaa cgtgttctcc tgctccgtga tgcacgaggc cctgcacaac     900
cactacaccc agaagtctct gtccctgagc cccggc                              936
```

```
<210> SEQ ID NO 66
<211> LENGTH: 312
<212> TYPE: PRT
<213> ORGANISM: Artificial Sequence
<220> FEATURE:
<223> OTHER INFORMATION: fusion protein

<400> SEQUENCE: 66
```

| | | | | | | | | | | | | | | |
|---|---|---|---|---|---|---|---|---|---|---|---|---|---|---|
| Gln | Leu | Tyr | Ser | Ala | Leu | Ala | Asn | Lys | Cys | Cys | His | Val | Gly | Cys | Thr |
| 1 | | | | 5 | | | | | 10 | | | | | 15 | |

| Lys | Arg | Ser | Leu | Ala | Arg | Phe | Cys | Gly | Gly | Gly | Ser | Gly | Gly | Gly |
|---|---|---|---|---|---|---|---|---|---|---|---|---|---|---|
| | | | 20 | | | | 25 | | | | 30 | | | |

| Gly | Ser | Gly | Gly | Gly | Ser | Ser | Trp | Met | Glu | Val | Ile | Lys | Leu |
|---|---|---|---|---|---|---|---|---|---|---|---|---|---|
| | | 35 | | | | 40 | | | | 45 | | | |

| Cys | Gly | Arg | Glu | Leu | Val | Arg | Ala | Gln | Ile | Ala | Ile | Cys | Gly | Met | Ser |
|---|---|---|---|---|---|---|---|---|---|---|---|---|---|---|---|
| | 50 | | | | | 55 | | | | | 60 | | | | |

| Thr | Trp | Ser | Ala | Ala | Ala | Gly | Gly | Gly | Ser | Gly | Gly | Gly | Ser |
|---|---|---|---|---|---|---|---|---|---|---|---|---|---|
| 65 | | | | | 70 | | | | 75 | | | | 80 |

| Gly | Gly | Gly | Gly | Ser | Gly | Gly | Gly | Ser | Ala | Cys | Pro | Cys | Pro |
|---|---|---|---|---|---|---|---|---|---|---|---|---|---|
| | | | | 85 | | | | 90 | | | | 95 | |

| Ala | Pro | Glu | Phe | Glu | Gly | Gly | Pro | Ser | Val | Phe | Leu | Phe | Pro | Pro | Lys |
|---|---|---|---|---|---|---|---|---|---|---|---|---|---|---|---|
| | | | | 100 | | | | | 105 | | | | | 110 | |

| Pro | Lys | Asp | Thr | Leu | Met | Ile | Ser | Arg | Thr | Pro | Glu | Val | Thr | Cys | Val |
|---|---|---|---|---|---|---|---|---|---|---|---|---|---|---|---|
| | | | 115 | | | | | 120 | | | | | 125 | | |

| Val | Val | Asp | Val | Ser | His | Glu | Asp | Pro | Glu | Val | Lys | Phe | Asn | Trp | Tyr |
|---|---|---|---|---|---|---|---|---|---|---|---|---|---|---|---|
| | 130 | | | | | 135 | | | | | 140 | | | | |

| Val | Asp | Gly | Val | Glu | Val | His | Asn | Ala | Lys | Thr | Lys | Pro | Arg | Glu | Glu |
|---|---|---|---|---|---|---|---|---|---|---|---|---|---|---|---|
| 145 | | | | | 150 | | | | | 155 | | | | | 160 |

| Gln | Tyr | Asn | Ser | Thr | Tyr | Arg | Val | Val | Ser | Val | Leu | Thr | Val | Leu | His |
|---|---|---|---|---|---|---|---|---|---|---|---|---|---|---|---|
| | | | | 165 | | | | | 170 | | | | | 175 | |

| Gln | Asp | Trp | Leu | Asn | Gly | Lys | Glu | Tyr | Lys | Cys | Lys | Val | Ser | Asn | Lys |
|---|---|---|---|---|---|---|---|---|---|---|---|---|---|---|---|
| | | | 180 | | | | | 185 | | | | | 190 | | |

| Ala | Leu | Pro | Ala | Ser | Ile | Glu | Lys | Thr | Ile | Ser | Lys | Ala | Lys | Gly | Gln |
|---|---|---|---|---|---|---|---|---|---|---|---|---|---|---|---|
| | | 195 | | | | | 200 | | | | | 205 | | | |

| Pro | Arg | Glu | Pro | Gln | Val | Tyr | Thr | Leu | Pro | Pro | Ser | Arg | Glu | Glu | Met |
|---|---|---|---|---|---|---|---|---|---|---|---|---|---|---|---|
| 210 | | | | | 215 | | | | | 220 | | | | | |

| Thr | Lys | Asn | Gln | Val | Ser | Leu | Thr | Cys | Leu | Val | Lys | Gly | Phe | Tyr | Pro |
|---|---|---|---|---|---|---|---|---|---|---|---|---|---|---|---|
| 225 | | | | | 230 | | | | | 235 | | | | | 240 |

| Ser | Asp | Ile | Ala | Val | Glu | Trp | Glu | Ser | Asn | Gly | Gln | Pro | Glu | Asn | Asn |
|---|---|---|---|---|---|---|---|---|---|---|---|---|---|---|---|
| | | | | 245 | | | | | 250 | | | | | 255 | |

| Tyr | Lys | Thr | Thr | Pro | Pro | Val | Leu | Asp | Ser | Asp | Gly | Ser | Phe | Phe | Leu |
|---|---|---|---|---|---|---|---|---|---|---|---|---|---|---|---|
| | | | 260 | | | | | 265 | | | | | 270 | | |

| Tyr | Ser | Lys | Leu | Thr | Val | Asp | Lys | Ser | Arg | Trp | Gln | Gln | Gly | Asn | Val |
|---|---|---|---|---|---|---|---|---|---|---|---|---|---|---|---|
| | | 275 | | | | | 280 | | | | | 285 | | | |

| Phe | Ser | Cys | Ser | Val | Met | His | Glu | Ala | Leu | His | Asn | His | Tyr | Thr | Gln |
|---|---|---|---|---|---|---|---|---|---|---|---|---|---|---|---|
| 290 | | | | | 295 | | | | | 300 | | | | | |

| Lys | Ser | Leu | Ser | Leu | Ser | Pro | Gly |
|---|---|---|---|---|---|---|---|
| 305 | | | | 310 | | | |

```
<210> SEQ ID NO 67
<211> LENGTH: 936
<212> TYPE: DNA
<213> ORGANISM: Artificial Sequence
<220> FEATURE:
<223> OTHER INFORMATION: DNA encoding fusion protein
```

<400> SEQUENCE: 67

```
tcctggatgg aggaggttat caagctgtgt ggacgcgaac tggtgcgcgc tcagatcgcg    60
atatgcggga tgtccacatg gtcaggcggc ggaggcagcg gcggtggcgg cagcggcggg   120
ggaggttctc agctctactc agcgctcgct aataagtgtt gtcatgtggg atgcacaaag   180
cggtctctcg ccagattctg cgcggccgcg ggtggaggtg gatccggagg aggtggaagc   240
ggaggaggtg gaagcggagg aggtggaagc gcttgtcctc catgcccggc gcctgagttc   300
gagggcggac cctccgtgtt cctgttcccc ccaaagccca aggacaccct gatgatctcc   360
cggaccccCg aagtgacctg cgtggtggtg gacgtgtccc acgaggaccc tgaagtgaag   420
ttcaattggt acgtggacgg cgtggaagtg cacaacgcca agaccaagcc cagagaggaa   480
cagtacaact ccacctaccg ggtggtgtcc gtgctgaccg tgctgcacca ggactggctg   540
aacggcaaag agtacaagtg caaggtctcc aacaaggccc tgcccgcctc catcgaaaag   600
accatctcca aggccaaggg ccagccccgc gagcctcagg tgtacacact gcccccagc    660
cgggaagaga tgaccaagaa ccaggtgtcc ctgacctgtc tggtgaaagg cttctacccc   720
tccgatatcg ctgtggaatg ggagtccaac ggccagcccg agaacaacta caagaccacc   780
cccctgtgc tggactccga cggctcattc ttcctgtact ccaagctgac cgtggacaag   840
tcccggtggc agcagggcaa cgtgttctcc tgctccgtga tgcacgaggc cctgcacaac   900
cactacaccc agaagtctct gtccctgagc cccggc                             936
```

<210> SEQ ID NO 68
<211> LENGTH: 312
<212> TYPE: PRT
<213> ORGANISM: Artificial Sequence
<220> FEATURE:
<223> OTHER INFORMATION: fusion protein

<400> SEQUENCE: 68

```
Ser Trp Met Glu Glu Val Ile Lys Leu Cys Gly Arg Glu Leu Val Arg
1               5                   10                  15
Ala Gln Ile Ala Ile Cys Gly Met Ser Thr Trp Ser Gly Gly Gly Gly
            20                  25                  30
Ser Gly Gly Gly Ser Gly Gly Gly Ser Gln Leu Tyr Ser Ala
        35                  40                  45
Leu Ala Asn Lys Cys Cys His Val Gly Cys Thr Lys Arg Ser Leu Ala
    50                  55                  60
Arg Phe Cys Ala Ala Gly Gly Gly Ser Gly Gly Gly Ser
65                  70                  75                  80
Gly Gly Gly Gly Ser Gly Gly Gly Ser Ala Cys Pro Pro Cys Pro
                85                  90                  95
Ala Pro Glu Phe Glu Gly Gly Pro Ser Val Phe Leu Phe Pro Pro Lys
            100                 105                 110
Pro Lys Asp Thr Leu Met Ile Ser Arg Thr Pro Glu Val Thr Cys Val
        115                 120                 125
Val Val Asp Val Ser His Glu Asp Pro Glu Val Lys Phe Asn Trp Tyr
    130                 135                 140
Val Asp Gly Val Glu Val His Asn Ala Lys Thr Lys Pro Arg Glu Glu
145                 150                 155                 160
Gln Tyr Asn Ser Thr Tyr Arg Val Val Ser Val Leu Thr Val Leu His
                165                 170                 175
Gln Asp Trp Leu Asn Gly Lys Glu Tyr Lys Cys Lys Val Ser Asn Lys
            180                 185                 190
```

```
Ala Leu Pro Ala Ser Ile Glu Lys Thr Ile Ser Lys Ala Lys Gly Gln
            195                 200                 205

Pro Arg Glu Pro Gln Val Tyr Thr Leu Pro Pro Ser Arg Glu Glu Met
    210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
    275                 280                 285

Phe Ser Cys Ser Val Met His Glu Ala Leu His Asn His Tyr Thr Gln
    290                 295                 300

Lys Ser Leu Cys Leu Ser Pro Gly
305                 310

<210> SEQ ID NO 69
<211> LENGTH: 21
<212> TYPE: PRT
<213> ORGANISM: Artificial Sequence
<220> FEATURE:
<223> OTHER INFORMATION: Connector

<400> SEQUENCE: 69

Gly Gly Gly Gly Ser Gly Gly Gly Ser Gly Gly Gly Gly Ser Gly
1               5                   10                  15

Gly Gly Gly Ser
            20

<210> SEQ ID NO 70
<211> LENGTH: 24
<212> TYPE: PRT
<213> ORGANISM: Artificial Sequence
<220> FEATURE:
<223> OTHER INFORMATION: Connector

<400> SEQUENCE: 70

Ala Ala Ala Gly Gly Gly Gly Ser Gly Gly Gly Gly Ser Gly Gly Gly
1               5                   10                  15

Gly Ser Gly Gly Gly Gly Ser Ala
            20
```

RELAXIN FUSION POLYPEPTIDES AND USES THEREOF

CROSS-REFERENCE TO RELATED APPLICATIONS

This application is a U.S. National Stage application of International Application No. PCT/EP2018/051757, filed on Jan. 24, 2018, said International Application No. PCT/EP2018/051757 claims benefit under 35 U.S.C. §119(e) of the U.S. Provisional Application No. 62/450,338, filed Jan. 25, 2017. Each of the above listed applications is incorporated by reference herein in its entirety for all purposes.

REFERENCE TO THE SEQUENCE LISTING

This application incorporates by reference a Sequence Listing filed together with this application in computer readable form (CRF) as a text file entitled "Sequence Listing" created on Jan. 24, 2018 and having a size of 63.9 kilobytes 99,253 bytes.

FIELD OF THE INVENTION

The present invention relates to Relaxin fusion polypeptides. In particular, the present invention relates to Relaxin 2 fusion polypeptides and uses thereof.

BACKGROUND

Relaxin is a peptide hormone that belongs to the insulin superfamily. In humans, the Relaxin peptide family includes seven peptides of high structural but low sequence similarity: Relaxin 1, 2 and 3, and the insulin-like peptides INSL3, INSL4, INSL5 and INSL6. The coding region of the relaxin genes starts with the signal peptide followed by a B polypeptide chain, C peptide and an A polypeptide chain. The signal peptide and the C peptide are proteolytically removed to produce the mature Relaxin protein, which consists of the A and B chains covalently linked by two inter-chain disulphide bonds. The A chain has an additional intra-chain disulphide bond. The mature Relaxin protein has a molecular weight of approximately 6000 Da.

Relaxin is a pleiotropic hormone that is known to mediate systemic haemodynamic and renal adaptive changes during pregnancy. Relaxin has also been shown to have anti-fibrotic properties and to have beneficial effects in heart failure. Heart failure is associated with significant morbidity and mortality. It is characterized by complex tissue remodelling involving increased cardiomyocyte death and interstitial fibrosis (Bathgate et al., 2013; Felker et al., 2014; Mentz et al., 2013; Tietjens et al., 2016; Wilson et al., 2015). Relaxin activates a number of signalling cascades which have been shown to be beneficial in the setting of ischemia-reperfusion and heart failure (Bathgate et al., 2013). These signalling pathways include activation of the phosphoinositide 3-kinase pathway and activation of the nitric oxide signalling pathway (Bathgate et al., 2013).

Clinical trials have been conducted using unmodified recombinant human Relaxin 2, serelaxin. Serelaxin is currently in a phase III clinical trial for acute decompensated heart failure (ADHF). In this study, serelaxin was dosed by continuous intravenous infusion for 48 hours to hospitalized heart failure patients (ClinicalTrials.gov Identifier: NCT02064868).

In previous completed clinical trials, intravenous administration of serelaxin improved the markers of cardiac, renal and hepatic damage and congestion (Felker et al., 2014; Teerlink et al., 2013; Metra et al., 2013). However, due to the rapid clearance of serelaxin from the patients' circulation, the therapeutic effect was limited to hospitalized patients and the positive effects rapidly disappeared once intravenous injection stopped. Additionally, approximately one third of the patients experienced a significant blood pressure drop (>40 mm Hg) after receiving serelaxin intravenously, with the consequence that the dose had to be reduced by half or even more.

WO 2013/004607 describes recombinant single chain Relaxin fusion polypeptides in which a Relaxin A chain polypeptide is fused to a Relaxin B chain polypeptide with a linker sequence. The authors found that a linker length of at least five amino acids and less than fifteen amino acids was required for Relaxin activity. WO 2013/004607 also describes recombinant single chain Relaxin 2 fusion polypeptides fused to the Fc domain of antibodies, which exhibited an improved half-life over wild-type Relaxin 2.

Given the promising clinical studies conducted so far with unmodified recombinant Relaxin, there remains a need for further recombinant Relaxin fusion polypeptides which retain a Relaxin biological activity and provide advantages such as an extended half-life and convenient dosing.

SUMMARY OF INVENTION

The present invention is concerned with Relaxin fusion polypeptides comprising a Relaxin A chain and a Relaxin B chain linked by a Linker polypeptide, in which the Linker polypeptide comprises at least 15 amino acids. In connection therewith, the invention provides a fusion polypeptide, a nucleic acid molecule, a vector, a host cell, a pharmaceutical composition and a kit comprising the same and uses of the same including methods of treatment.

Aspects and embodiments of the invention are set out in the appended claims. These and other aspects and embodiments of the invention are also described herein.

BRIEF DESCRIPTION OF FIGURES AND SEQUENCE LISTING

The present invention will now be described in more detail with reference to the attached Figures, in which:

FIG. 1 provides a schematic representation and abbreviated names of Relaxin 2 fusion polypeptides according to some embodiments of the invention;

FIG. 2 shows the nucleotide (top) and amino acid (bottom) sequences of a Relaxin 2 fusion polypeptide according to an embodiment of the invention (Fc_hRLX2_4-15AA) (underlined are the Connector (single underlining) and the Linker (double underlining) sequences, respectively);

FIG. 3 shows the nucleotide (top) and amino acid (bottom) sequences of a Relaxin 2 fusion polypeptide according to an embodiment of the invention (Fc-TM_hRLX2_4-15AA) (underlined are the Connector (single underlining) and the Linker (double underlining) sequences, respectively; underlined and bold are the TM mutations in the Fc part);

FIG. 4 shows the nucleotide (top) and amino acid (bottom) sequences of a Relaxin 2 fusion polypeptide according to an embodiment of the invention (Fc-FQQ_hRLX2_4-15AA) (underlined are the Connector (single underlining) and the Linker (double underlining) sequences, respectively; underlined and bold are the FQQ mutations in the Fc part);

FIG. 5 shows the nucleotide (top) and amino acid (bottom) sequences of a Relaxin 2 fusion polypeptide according to an embodiment of the invention (Fc-YTE_hRLX2_4-

Figure 21:
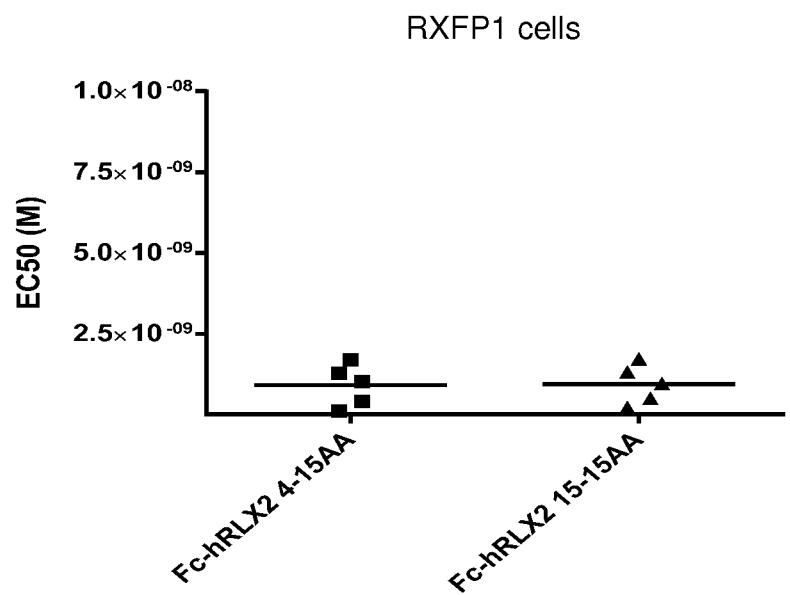
Figure 22:
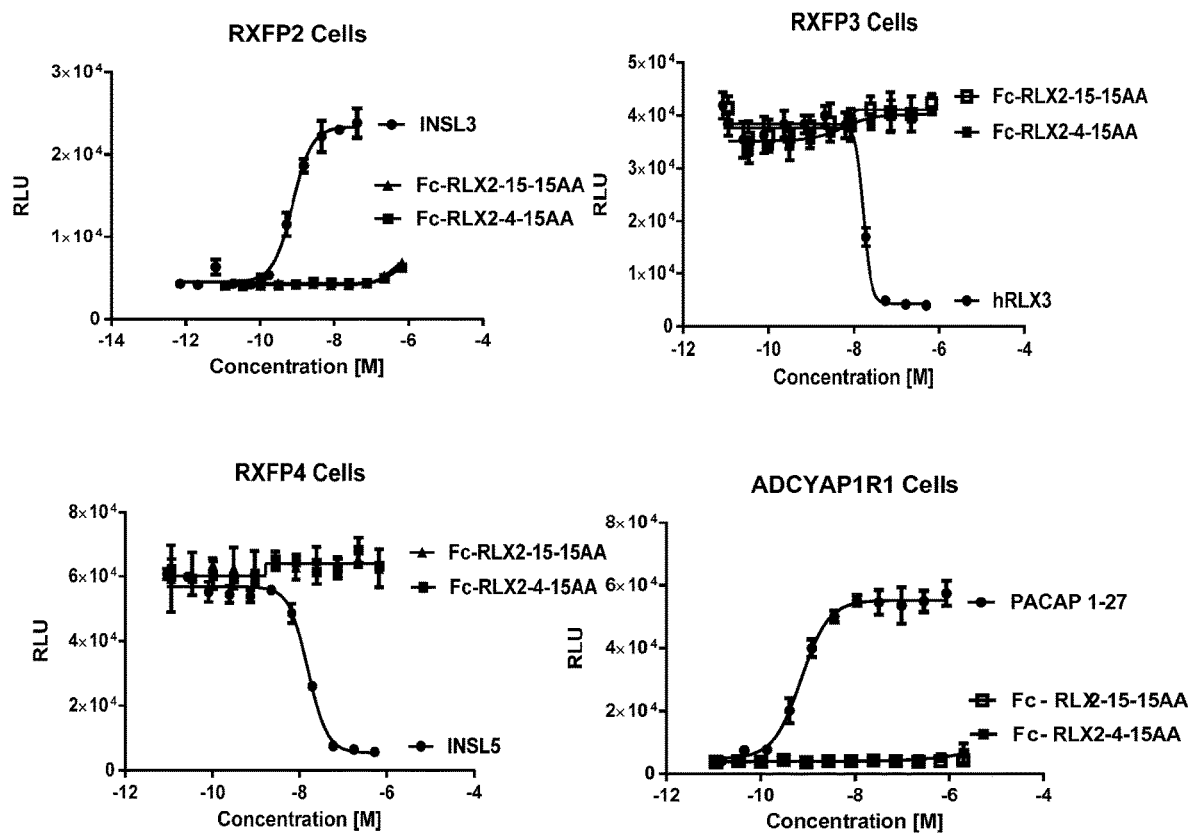
Figure 23:
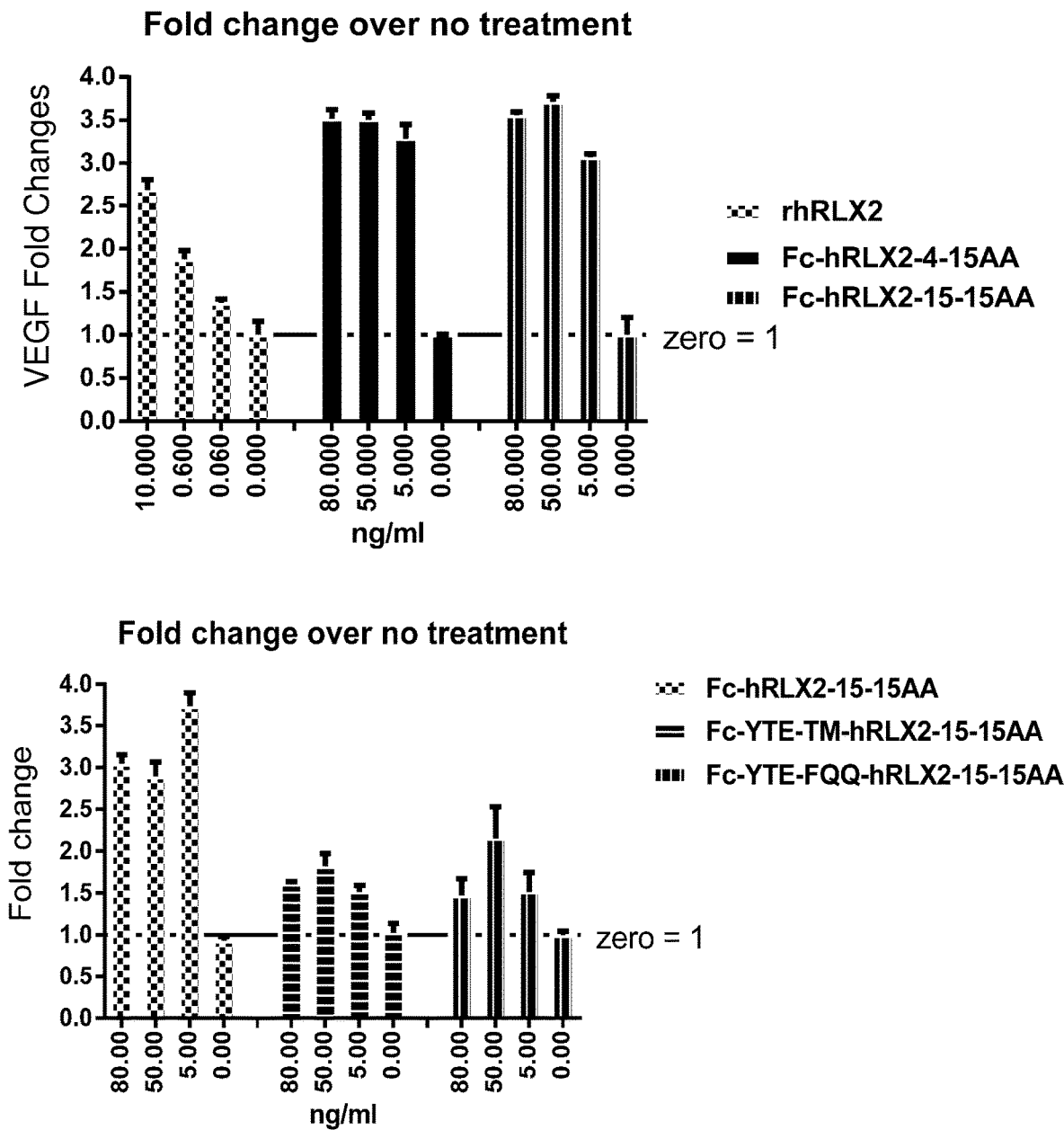
Figure 24:
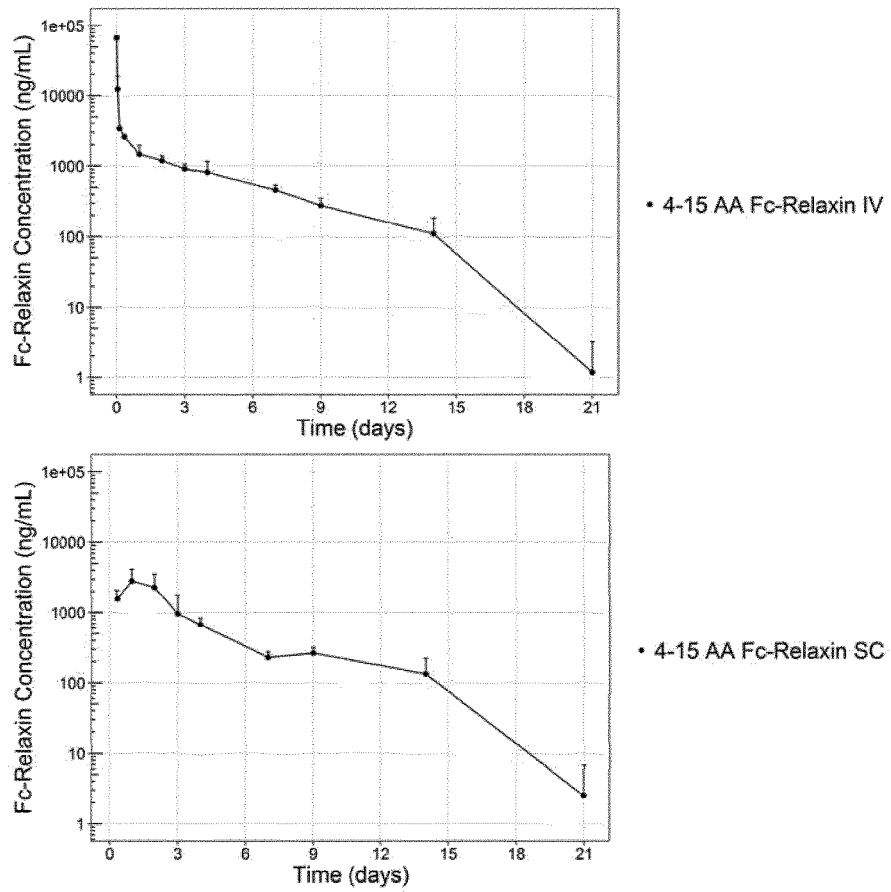
Figure 25:
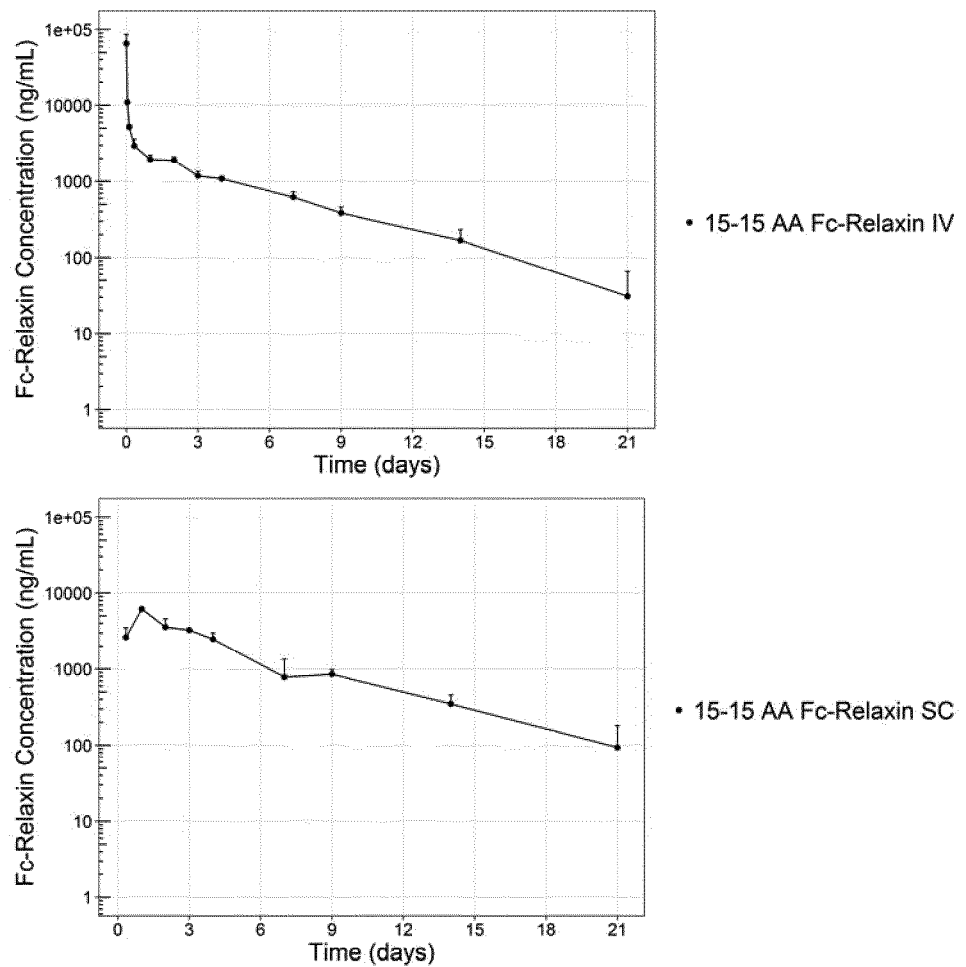
Figure 26:
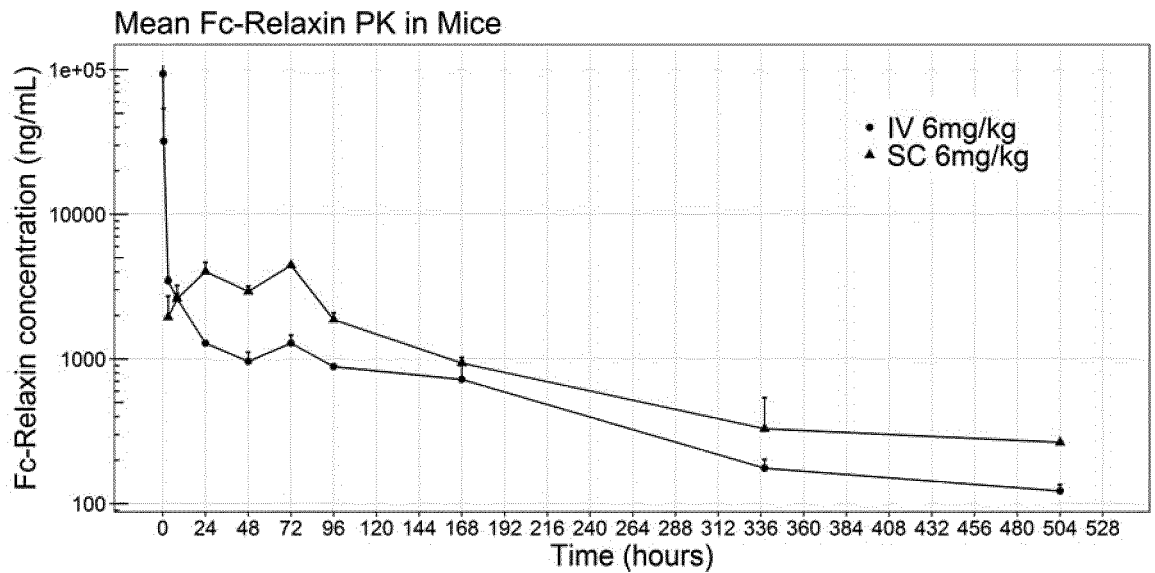
Figure 27:
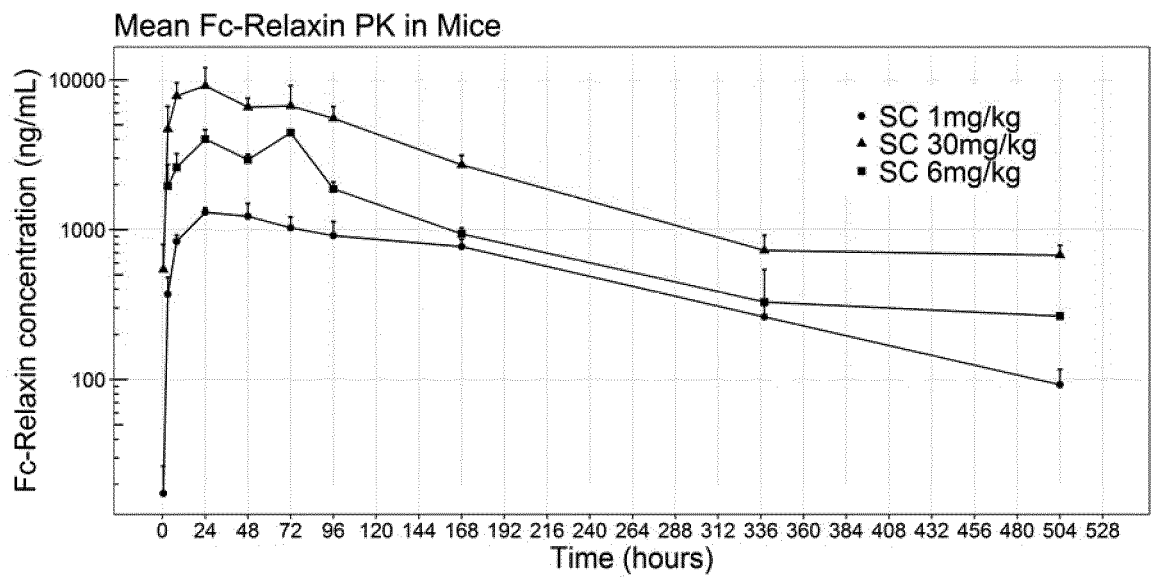
Figure 28:
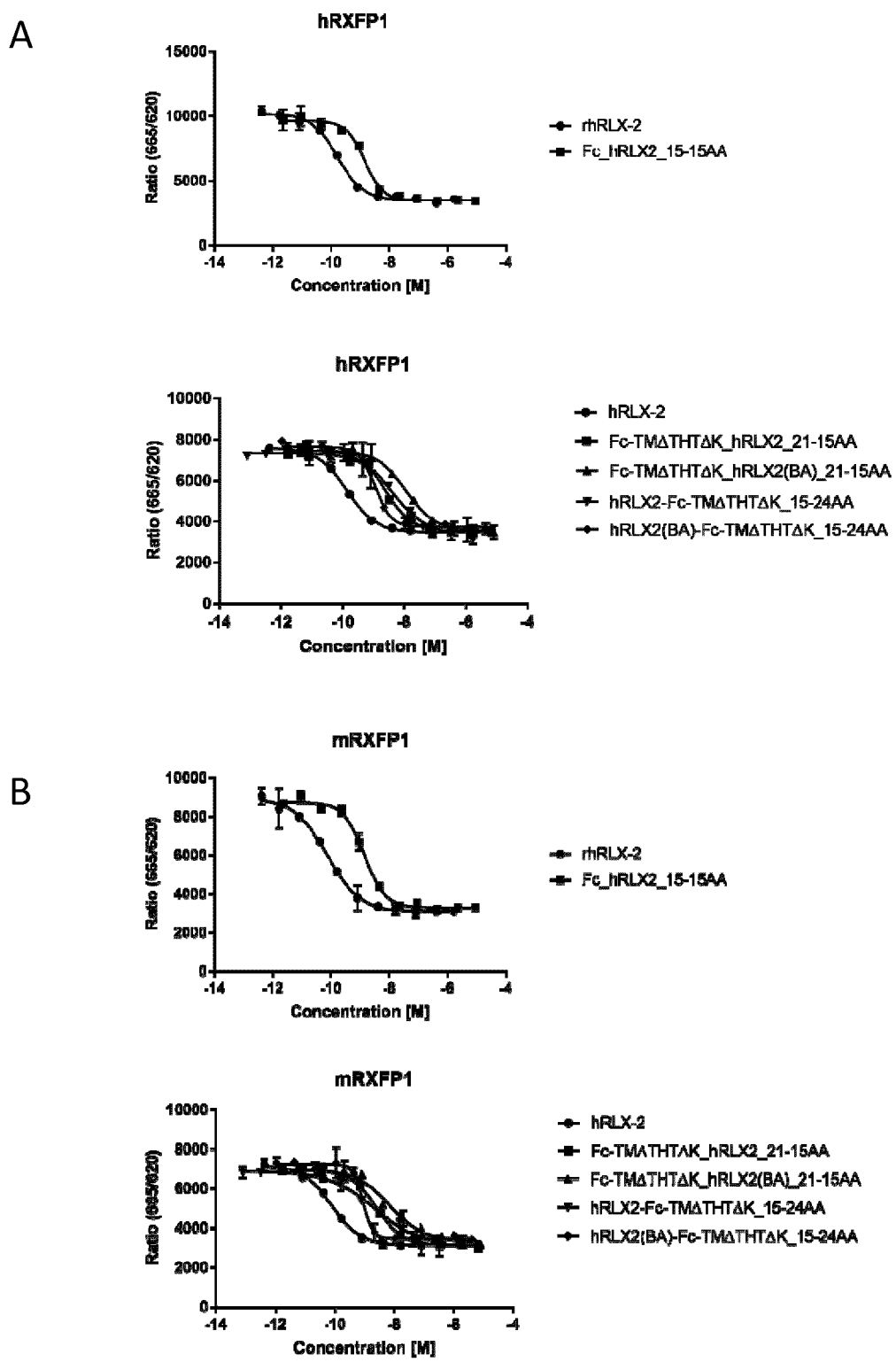
Figure 28:
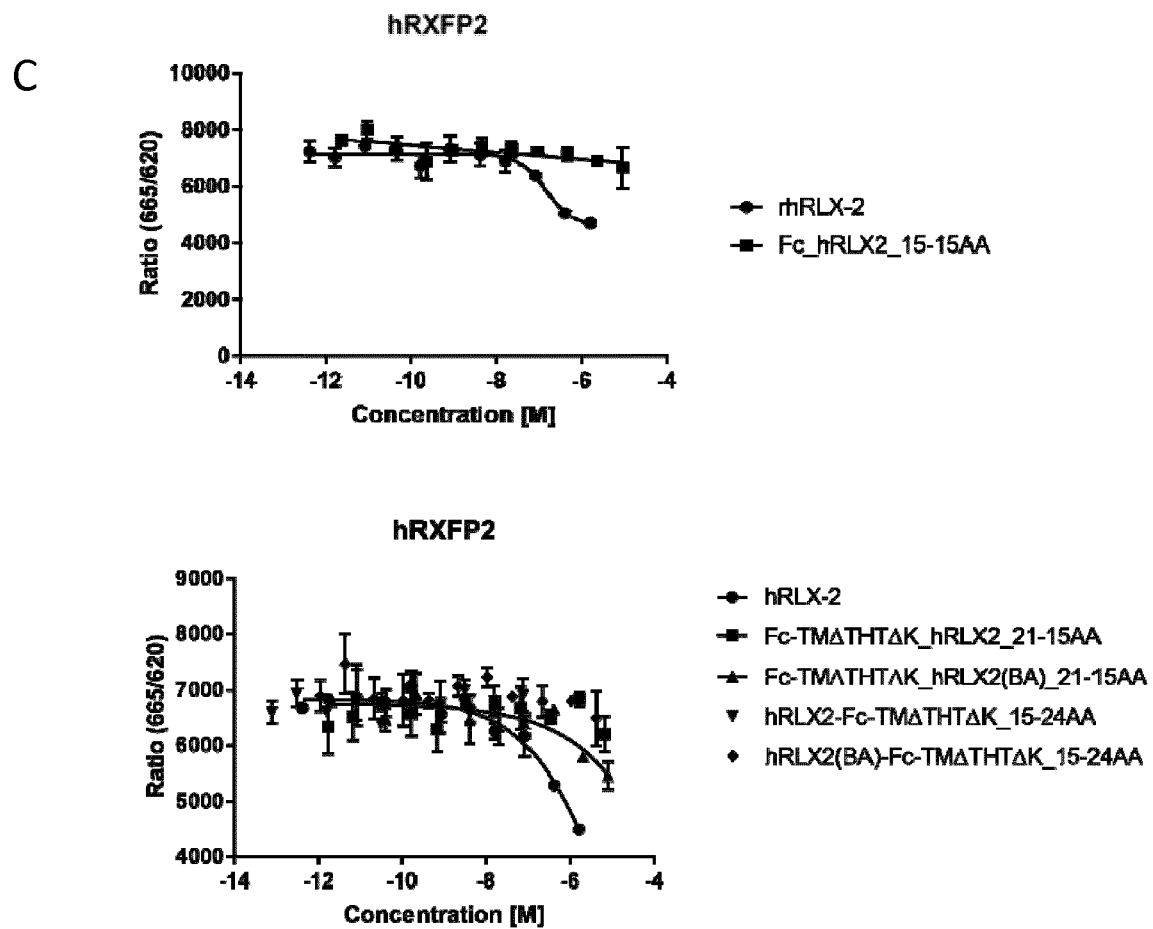

15AA) (underlined are the Connector (single underlining) and the Linker (double underlining) sequences, respectively; underlined and bold are the YTE mutations in the Fc part);

FIG. 6 shows the nucleotide (top) and amino acid (bottom) sequences of a Relaxin 2 fusion polypeptide according to an embodiment of the invention (Fc-YTE-TM_hRLX2_4-15AA) (underlined are the Connector (single underlining) and the Linker (double underlining) sequences, respectively; underlined and bold are the YTE-TM mutations in the Fc part);

FIG. 7 shows the nucleotide (top) and amino acid (bottom) sequences of a Relaxin 2 fusion polypeptide according to an embodiment of the invention (Fc-YTE-FQQ_hRLX2_4-15AA) (underlined are the Connector (single underlining) and the Linker (double underlining) sequences, respectively; underlined and bold are the YTE-FQQ mutations in the Fc part);

FIG. 8 shows the nucleotide (top) and amino acid (bottom) sequences of a Relaxin 2 fusion polypeptide according to an embodiment of the invention (Fc-G4P_hRLX2_4-15AA) (underlined are the Connector (single underlining) and the Linker (double underlining) sequences, respectively);

FIG. 9 shows the nucleotide (top) and amino acid (bottom) sequences of a Relaxin 2 fusion polypeptide according to an embodiment of the invention (Fc_hRLX2_15-15AA) (underlined are the Connector (single underlining) and the Linker (double underlining) sequences, respectively);

FIG. 10 shows the nucleotide (top) and amino acid (bottom) sequences of a Relaxin 2 fusion polypeptide according to an embodiment of the invention (Fc-TM_hRLX2_15-15AA) (underlined are the Connector (single underlining) and the Linker (double underlining) sequences, respectively; underlined and bold are the TM mutations in the Fc part);

FIG. 11 shows the nucleotide (top) and amino acid (bottom) sequences of a Relaxin 2 fusion polypeptide according to an embodiment of the invention (Fc-FQQ_hRLX2_15-15AA) (underlined are the Connector (single underlining) and the Linker (double underlining) sequences, respectively; underlined and bold are the FQQ mutations in the Fc part);

FIG. 12 shows the nucleotide (top) and amino acid (bottom) sequences of a Relaxin 2 fusion polypeptide according to an embodiment of the invention (Fc-YTE_hRLX2_15-15AA) (underlined are the Connector (single underlining) and the Linker (double underlining) sequences, respectively; underlined and bold are the YTE mutations in the Fc part);

FIG. 13 shows the nucleotide (top) and amino acid (bottom) sequences of a Relaxin 2 fusion polypeptide according to an embodiment of the invention (Fc-YTE-TM_hRLX2_15-15AA) (underlined are the Connector (single underlining) and the Linker (double underlining) sequences, respectively; underlined and bold are the YTE-TM mutations in the Fc part);

FIG. 14 shows the nucleotide (top) and amino acid (bottom) sequences of a Relaxin 2 fusion polypeptide according to an embodiment of the invention (Fc-YTE-FQQ_hRLX2_15-15AA) (underlined are the Connector (single underlining) and the Linker (double underlining) sequences, respectively; underlined and bold are the YTE-FQQ mutations in the Fc part);

FIG. 15 shows the nucleotide (top) and amino acid (bottom) sequences of a Relaxin 2 fusion polypeptide according to an embodiment of the invention (Fc-G4P_hRLX2_15-15AA) (underlined are the Connector (single underlining) and the Linker (double underlining) sequences, respectively);

FIG. 16 shows the nucleotide (top) and amino acid (bottom) sequences of a Relaxin 2 fusion polypeptide according to an embodiment of the invention (Fc-TMΔTHTΔK_hRLX2_21-15AA) (underlined are the Connector (single underlining) and the Linker (double underlining) sequences, respectively); underlined and bold are the TMΔTHTΔK mutations in the Fc part);

FIG. 17 shows the nucleotide (top) and amino acid (bottom) sequences of a Relaxin 2 fusion polypeptide according to an embodiment of the invention (Fc-TMΔTHTΔK_hRLX2(BA)_21-15AA) (underlined are the Connector (single underlining) and the Linker (double underlining) sequences, respectively); underlined and bold are the TMΔTHTΔK mutations in the Fc part);

FIG. 18 shows the nucleotide (top) and amino acid (bottom) sequences of a Relaxin 2 fusion polypeptide according to an embodiment of the invention (hRLX2_Fc-TMΔTHTΔK_15-24AA) (underlined are the Connector (single underlining) and the Linker (double underlining) sequences, respectively); underlined and bold are the TMΔTHTΔK mutations in the Fc part);

FIG. 19 shows the nucleotide (top) and amino acid (bottom) sequences of a Relaxin 2 fusion polypeptide according to an embodiment of the invention (hRLX2(BA)_Fc-TMΔTHTΔK_15-24AA) (underlined are the Connector (single underlining) and the Linker (double underlining) sequences, respectively); underlined and bold are the TMΔTHTΔK mutations in the Fc part);

FIG. 20 shows the in vitro activity of some Relaxin 2 fusion polypeptides of the invention in RXFP1-expressing cells. Relative light units (RLU) represents the stimulation of cAMP production;

FIG. 21 shows the in vitro activity (stimulation of cAMP production) of some Relaxin 2 fusion polypeptides of the invention in RXFP1-expressing cells;

FIG. 22 shows the specificity of some Relaxin 2 fusion polypeptides of the invention for the relaxin-2 receptor;

FIG. 23 shows induction of VEGF expression by some Relaxin 2 fusion polypeptides of the invention. In this figure, "zero=1" means that the activity measured with a mock "no treatment" control (i.e. without addition of RLX2 or RLX2 fusion polypeptides in the assay) was taken as the baseline (i.e. the fold change value of "no treatment" control is 1);

FIG. 24 shows rat PK profiles of the fusion polypeptide Fc_hRLX2_4-15AA (4 mg/kg) administered intravenously (top) or subcutaneously (bottom);

FIG. 25 shows rat PK profiles of the fusion polypeptide Fc_hRLX2_15-15AA (4 mg/kg) administered intravenously (top) or subcutaneously (bottom);

FIG. 26 shows mouse PK profiles of the fusion polypeptide Fc_hRLX2_15-15AA (6 mg/kg) administered intravenously ("IV", circles) or subcutaneously ("SC", triangles). "CL" represents total body clearance of Fc-Relaxin following IV administration and "CL/F" represents the apparent total body clearance of Fc-Relaxin following SC administration;

FIG. 27 shows mouse PK profiles of the fusion polypeptide Fc_hRLX2_15-15AA (1 mg/kg (circles), 6 mg/kg (squares) and 30 mg/kg (triangles)) administered subcutaneously. "CL" represents total body clearance of Fc-Relaxin following IV administration and "CL/F" represents the apparent total body clearance of Fc-Relaxin following SC administration;

FIG. 28 shows the in vitro activity of some Fc-Relaxin-2 fusion polypeptides of the invention in human (A) and mouse (B) cell lines and RXFP2 selectivity (C), in cell-based cAMP assays;

FIG. 29 shows prevention of isoproterenol-induced cardiac hypertrophy in mice treated with Fc_hRLX2_15-15AA. (A) represents the ratio of Heart Weight (HW)/Tibia Length (TL) (mg/mm), (B) represents the Collagen content (pg/mg tissue), for the 6 groups tested: (1) vehicle, (2) Fc_hRLX2_15-15AA, (3) isoproterenol, (4) isoproterenol+enalapril, (5) isoproterenol+rhRLX2, (6) isoproterenol+Fc_hRLX2_15-15AA.

KEY TO SEQ ID NOS

| Construct | Type | SEQ ID NO. |
|---|---|---|
| Fc_hRLX2_4-15AA | DNA | 1 |
| Fc_hRLX2_4-15AA | PROTEIN | 2 |
| Fc-TM_hRLX2_4-15AA | DNA | 3 |
| Fc-TM_hRLX2_4-15AA | PROTEIN | 4 |
| Fc-FQQ_hRLX2_4-15AA | DNA | 5 |
| Fc-FQQ_hRLX2_4-15AA | PROTEIN | 6 |
| Fc-YTE_hRLX2_4-15A | DNA | 7 |
| Fc-YTE_hRLX2_4-15A | PROTEIN | 8 |
| Fc-YTE-TM-hRLX2-4-15AA | DNA | 9 |
| Fc-YTE-TM-hRLX2-4-15AA | PROTEIN | 10 |
| Fc-YTE-FQQ-hRLX2-4-15A | DNA | 11 |
| Fc-YTE-FQQ-hRLX2-4-15A | PROTEIN | 12 |
| Fc-G4P_hRLX2_4-15AA | DNA | 13 |
| Fc-G4P_hRLX2_4-15AA | PROTEIN | 14 |
| Fc_hRLX2_15-15A | DNA | 15 |
| Fc_hRLX2_15-15A | PROTEIN | 16 |
| Fc-TM_hRLX2_15-15AA | DNA | 17 |
| Fc-TM_hRLX2_15-15AA | PROTEIN | 18 |
| Fc-FQQ_hRLX2_15-15AA | DNA | 19 |
| Fc-FQQ_hRLX2_15-15AA | PROTEIN | 20 |
| Fc-YTE_hRLX2_15-15AA | DNA | 21 |
| Fc-YTE_hRLX2_15-15AA | PROTEIN | 22 |
| Fc-YTE-TM_hRLX2_15-15AA | DNA | 23 |
| Fc-YTE-TM_hRLX2_15-15AA | PROTEIN | 24 |
| Fc-YTE-FQQ_hRLX2_15-15A | DNA | 25 |
| Fc-YTE-FQQ_hRLX2_15-15A | PROTEIN | 26 |
| Fc-G4P_hRLX2_15-15AA | DNA | 27 |
| Fc-G4P_hRLX2_15-15AA | PROTEIN | 28 |
| Fc-TMΔTHTΔK_hRLX2_21-15AA | DNA | 61 |
| Fc-TMΔTHTΔK_hRLX2_21-15AA | PROTEIN | 62 |
| Fc-TMΔTHTΔK_hRLX2(BA)_21-15AA | DNA | 63 |
| Fc-TMΔTHTΔK_hRLX2(BA)_21-15AA | PROTEIN | 64 |
| hRLX2-Fc-TMΔTHTΔK_15-24AA | DNA | 65 |
| hRLX2-Fc-TMΔTHTΔK_15-24AA | PROTEIN | 66 |
| hRLX2(BA)-Fc-TMΔTHTΔK_15-24AA | DNA | 67 |
| hRLX2(BA)-Fc-TMΔTHTΔK_15-24AA | PROTEIN | 68 |
| Fc-TM | DNA | 29 |
| Fc-TM | PROTEIN | 30 |
| Fc-FQQ | DNA | 31 |
| Fc-FQQ | PROTEIN | 32 |
| Fc-YTE | DNA | 33 |
| Fc-YTE | PROTEIN | 34 |
| Fc-YTE-TM | DNA | 35 |
| Fc-YTE-TM | PROTEIN | 36 |
| Fc-YTE-FQQ | DNA | 37 |
| Fc-YTE-FQQ | PROTEIN | 38 |
| Fc-G4P | DNA | 39 |
| Fc-G4P | PROTEIN | 40 |
| Human relaxin 2 A chain | DNA | 41 |
| Human relaxin 2 A chain | PROTEIN | 42 |
| Human relaxin 2 B chain | DNA | 43 |
| Human relaxin 2 B chain | PROTEIN | 44 |
| Human relaxin 2 B chain variant | DNA | 45 |
| Human relaxin 2 B chain variant | PROTEIN | 46 |
| Human relaxin 2 C peptide | DNA | 47 |
| Human relaxin 2 C peptide | PROTEIN | 48 |
| Human relaxin 3 A chain | DNA | 49 |
| Human relaxin 3 A chain | PROTEIN | 50 |
| Human relaxin 3 B chain | DNA | 51 |
| Human relaxin 3 B chain | PROTEIN | 52 |
| Human relaxin 3 C peptide | DNA | 53 |
| Human relaxin 3 C peptide | PROTEIN | 54 |
| Conserved motif RXXXRXXI | PROTEIN | 55 |
| Connector 4AA: GGSP | PROTEIN | 56 |

-continued

| Construct | Type | SEQ ID NO. |
|---|---|---|
| Connector or linker 15AA: GGGGSGGGGSGGGGS | PROTEIN | 57 |
| Linker GGGGS | PROTEIN | 58 |
| Linker A(EAAAK)$_5$A | PROTEIN | 59 |
| Conserved motif RXXXRXXV | PROTEIN | 60 |
| Connector 21AA: (GGGGS)$_3$GGGGGS | PROTEIN | 69 |
| Connector 24AA: AAA(GGGGS)$_4$A | PROTEIN | 70 |

DETAILED DESCRIPTION

The present invention relates to Relaxin fusion polypeptides having the structure A-L-B or B-L-A, in which a Relaxin A chain (A) is linked via a linker polypeptide (L) to a Relaxin B chain (B), and in which the linker polypeptide L is at least 15 amino acids in length. In some embodiments, the Relaxin fusion polypeptides are Relaxin 2 fusion polypeptides. Relaxin 2 fusion polypeptides comprise a Relaxin 2 A chain and a Relaxin 2 B chain.

The present invention is based upon the surprising finding that fusion polypeptides in which the linker polypeptide L comprises at least 15 amino acids have Relaxin activity. Thus, the inventors have found that Relaxin 2 fusion polypeptides in which the C terminus of the A chain is connected with a linker of 15 amino acids to the N-terminus of the B chain exhibit biological activity comparable to Relaxin 2 protein having the A chain and B chain array of a mature Relaxin 2 polypeptide (i.e. without a linker between the A and B chains), such as the Relaxin 2 polypeptide of UniProtKB/Swiss-Prot Accession Number P04090.1. Similarly, the inventors have found that Relaxin 2 fusion polypeptides in which the C terminus of the B chain is connected with a linker of 15 amino acids to the N-terminus of the A chain exhibit biological activity comparable to Relaxin 2 protein having the A chain and B chain array of a mature Relaxin 2 polypeptide These findings are particularly surprising in view of the teaching in PCT publication WO 2013/004607, in which a linker length of less than fifteen amino acids was found to be necessary for biological activity.

Naturally occurring Relaxins are expressed as prohormones with the structure B-C-A, (where "B" is the B chain, "C" is the C peptide, and "A" is the A chain of Relaxin) and the mature proteins are produced by endoproteolytic cleavage of the prohormone with the Prohormone-Convertase 1 (PC1) and Prohormone-Convertase 2 (PC2) enzymes to remove the C peptide. It will be understood that the fusion polypeptides of the invention do not undergo such endoproteolytic cleavage by PC1 and PC2.

The fusion polypeptides of the invention comprise a Relaxin A chain polypeptide or a variant thereof and a Relaxin B chain polypeptide or a variant thereof. In some embodiments, the Relaxin B chain polypeptide does not have any attachments at its C-terminus. In other words, the Relaxin B chain polypeptide has a free C-terminus.

in other embodiments, the Relaxin A chain polypeptide does not have any attachments at its C-terminus. In other words, the Relaxin A chain polypeptide has a free C-terminus.

The fusion polypeptides may comprise Relaxin A and B chain polypeptides from the group of Relaxins selected from Relaxin 1, Relaxin 2 and Relaxin 3. In some embodiments, the fusion polypeptides comprise Relaxin A and B chain polypeptides from Relaxin 2 or Relaxin 3. Thus, the fusion polypeptides may comprise a Relaxin 2 A or a Relaxin 3 A chain polypeptide or a variant thereof and a Relaxin 2 B or a Relaxin 3 B chain polypeptide or a variant thereof. In some other embodiments, the fusion polypeptides comprise a Relaxin 3 A chain polypeptide or a variant thereof and a Relaxin 3 B chain polypeptide or a variant thereof. In particular, the fusion polypeptides may comprise human Relaxin A and B chain polypeptides.

The fusion polypeptides may comprise a Relaxin 2 A chain polypeptide or a variant thereof and a Relaxin 2 B chain polypeptide or a variant thereof. In particular embodiments, the Relaxin A chain polypeptide comprises a human Relaxin 2 A chain polypeptide or a variant thereof and a human Relaxin 2 B chain polypeptide or a variant thereof. The human Relaxin 2 A chain polypeptide may have the sequence as set forth in SEQ ID NO. 42 or a variant thereof and the human Relaxin 2 B chain polypeptide may have the sequence as set forth in SEQ ID NO. 44 or SEQ ID NO. 46 or variants thereof. In further embodiments, the human Relaxin 2 A chain polypeptide has the sequence as set forth in SEQ ID NO. 42 and the human Relaxin 2 B chain polypeptide has the sequence as set forth in SEQ ID NO. 46.

Relaxin A and B chain variants are known in the art. In addition, guidance on the design of Relaxin A and B chain variants is available to the skilled person. For example, it will be understood that variants may retain those amino acids that are required for Relaxin function. For example, Relaxin 2 B chain variants may comprise the conserved motif Arg-X-X-X-Arg-X-X-Ile (SEQ ID NO. 55) (Claasz et al, 2002, Wilkinson et al., 2005) or Arg-X-X-X-Arg-X-X-Val (SEQ ID NO. 60) (Bathgate et al, 2013). Variants may comprise one or more amino acid substitutions, deletions and/or insertions. For example, Relaxin 2 B chain variants may have one or more additional amino acids selected from Val23, Ala24, Lys54, Arg55 and N-terminal Met compared to SEQ ID NO. 44. Alternatively or in addition, variants may comprise one or more amino acid derivatives. For example, the first amino acid of Relaxin 2 B chain variants may be pyroglutamate.

The terms "protein", "polypeptide" and "peptide" may be used interchangeably herein to refer to a chain of two or more amino acids linked through peptide bonds.

The fusion polypeptides of the invention may be recombinant fusion polypeptides, i.e. which have been created by recombinant DNA technology. Unlike wild-type Relaxin proteins, the fusion polypeptides of the invention do not require endoproteolytic processing for biological activity.

The Relaxin family peptides mediate their biological effects, at least in part, through the activation of G protein-coupled receptors (GPCRs), and the subsequent stimulation or inhibition of the cAMP signalling pathway by the Gs or Gi protein subunit, respectively. Relaxin 2 is known to activate the GPCR RXFP1 (also known as LGR7) and, to a lesser degree, the GPCR RXFP2 (also known as LGR8), thus stimulating the Gs-cAMP-dependent signalling pathway, leading to an increase in the second messenger molecule cAMP.

As used herein, the term "Relaxin activity" refers to the ability of a Relaxin molecule to bind to a Relaxin receptor, and/or activate said Relaxin receptor and/or initiate a signalling cascade inside the cell. In embodiments in which the Relaxin activity is Relaxin 2 activity, Relaxin activity may refer to the ability to bind and/or activate the receptor RXFP1 and/or RXFP2. In embodiments in which the Relaxin activity is Relaxin 3 activity, Relaxin activity may refer to the ability to bind and/or activate the receptor RXFP1, RXFP3 and/or RXFP4 (Bathgate et al., 2013). The term "Relaxin activity" may be used interchangeably with "biological activity".

Relaxin activity may be determined by measuring binding of a Relaxin molecule to a Relaxin receptor, and/or by measuring downstream events from binding to a Relaxin receptor.

Relaxin activity may be determined in vitro and/or in vivo. In some embodiments, Relaxin activity is determined in vitro.

Relaxin activity may be determined by measuring the amount and/or presence of a molecule downstream from Relaxin activation of a receptor. For example, Relaxin activity may be determined by measuring cAMP production following Relaxin activation of a receptor. Methods for the detection of Relaxin-induced cAMP generation are known in the art. Such methods include cAMP ELISA and the HitHunter® cAMP assay. Relaxin activity may also be determined by measuring nitric oxide (NO) production following Relaxin activation of a receptor. Relaxin activity may also be determined by measuring the activation of a molecule downstream from Relaxin activation of a receptor. For example, Relaxin activity may be determined by measuring activation of p42/44 MAPK.

Alternatively or in addition, Relaxin activity may be determined by measuring the activation of a known Relaxin target gene. For example, Relaxin activity may be determined by measuring the activation of the transcription of the known Relaxin target gene, VEGF, in THP-1 cells. Methods to determine activation of transcription of a gene are known in the art and include quantitative PCR analysis of the mRNA. The relative expression of VEGF mRNA can be measured by quantitative real-time PCR induction of VEGF transcripts following incubation of THP-1 cells with Relaxin as described in Xiao et al. (2013).

Alternatively or in addition, Relaxin activity may be determined by measuring one or more downstream effects of Relaxin. For example, reduction of cardiac hypertrophy can be measured by echocardiography, left ventricular weight relative to body weight and/or tibia length according to standard methods. In another example, Relaxin activity may be determined by measuring fibrosis reduction by Masson's Trichrome stain. In another example, Relaxin activity may be determined by measuring modulation of connective tissue metabolism, such as the inhibition of profibrotic factors (such as TGF-beta), inhibition of fibroblast proliferation and differentiation, and/or activation of MMP-mediated extracellular matrix degradation (Bathgate et al, 2013).

The activity of the Relaxin fusion polypeptides of the invention may be determined in relation to a reference Relaxin protein. In some embodiments, the reference Relaxin protein is a recombinant protein. The activity of the Relaxin fusion polypeptides may be determined in relation to a reference Relaxin protein having the Relaxin A chain and Relaxin B chain array of a mature Relaxin polypeptide (i.e. without a linker between the A and B chains), such as the Relaxin 2 polypeptide of UniProtKB/Swiss-Prot Accession Number P04090.1). Such Relaxins are commercially available. For example, recombinant human Relaxin 2 having the Relaxin 2 chain A and Relaxin 2 chain B array of mature human Relaxin 2 is available from R&D systems (catalogue number 6586-RN-025). In some embodiments, the reference Relaxin protein has the same A and B Relaxin chains as the A and B Relaxin chains of the fusion polypeptides of the invention or differs from the A and B Relaxin chains of the fusion polypeptides of the invention by up to 10 amino acids, for example 1 or 2 amino acids. In other embodiments, the first amino acid of the B chain of the reference Relaxin 2 is D and this amino acid is deleted in the B chain of the fusion polypeptide of the invention. In further embodiments, when the fusion polypeptide comprises the Relaxin 2 A chain polypeptide of SEQ ID NO. 42 and the Relaxin 2 B chain polypeptide of SEQ ID NO. 44 or 46, the reference Relaxin is recombinant Relaxin 2 having the chain A and chain B array of mature human Relaxin 2 and having the amino acid sequence disclosed under UniProtKB/Swiss-Prot Accession Number P04090.1.

The fusion polypeptides of the invention may be considered to have Relaxin activity if they show at least a proportion of the activity of a reference Relaxin protein. For example, a fusion polypeptide may be considered to have Relaxin activity if it has at least about half of the activity of a reference Relaxin protein. Alternatively, a fusion polypeptide of the invention may be considered to have Relaxin activity if the ratio of the activity of said fusion polypeptide over the activity of a reference Relaxin protein is comprised between 1 and about $10^5$, between 1 and about $10^4$, between about 1 and about $10^3$, between about 1 and about 100, between about 1 and about 50, between about 1 and about 20, between about 1 and about 15, between about 1 and about 10, or between about 1 and about 5. Alternatively, a fusion polypeptide of the invention may be considered to have Relaxin activity if the ratio of the activity of said fusion polypeptide over the activity of a reference Relaxin protein is comprised between about $10^{-5}$ and about 1, between about $10^{-4}$ and about 1, between about $10^{-3}$ and about 1, between about $10^{-2}$ and about 1, between about 1/50 and about 1, between about 1/20 and about 1, between about 1/15 and about 1, between about 1/10 and about 1, between about 1/5 and about 1.

In certain embodiments, the ratio of Relaxin activity of the fusion polypeptide of the invention over the Relaxin activity of the reference Relaxin protein is comprised between about $10^{-5}$ and about $10^5$.

In some embodiments, the ratio of the activity of a fusion polypeptide of the invention over the activity of a reference Relaxin protein is comprised between about 1 and about 100, for instance between about 1 and about 50, between about 1 and about 20, or between about 1 and about 15, or between about 1 and about 10 or between about 1 and about 5.

In other embodiments, the ratio of the activity of the fusion polypeptide of the invention over the activity of a reference Relaxin protein is comprised between about $10^{-2}$ and about 1, or between about 1/50 and about 1, for instance between about 1/20 and about 1, between about 1/15 and about 1, between about 1/10 and about 1, or between about 1/5 and about 1.

In still other embodiments, the ratio of the activity of the fusion polypeptide of the invention over the activity of a reference Relaxin protein is about 1.

Relaxin activity may be determined as an EC50 value. As used herein the term "EC50" (half maximal effective concentration) refers to the effective concentration of a therapeutic compound which induces a response halfway between the baseline and maximum after a specified exposure time.

The inventors have shown that the fusion polypeptides of the invention have Relaxin activity as does a Relaxin protein having the Relaxin 2 A chain and Relaxin 2 B chain array of a mature Relaxin 2 polypeptide (i.e. without a linker between the A and B chain) such as the recombinant Relaxin protein from R&D systems (catalogue number 6586-RN-025). As shown in the experimental section, the ratio of the average EC50 value determined for some fusion polypeptides of the invention over the average EC50 value determined for the recombinant Relaxin protein from R&D systems (catalogue number 6586-RN-025) is comprised between about 1 and about 100. Accordingly, the fusion polypeptides of the invention may have an EC50 value that is the same or substantially the same as the EC50 value of a reference Relaxin protein. Alternatively, the fusion polypeptides may have an EC50 value that is greater than the EC50 value of a reference Relaxin protein. Alternatively, the fusion polypeptides may have an EC50 value that is less than the EC50 value of a reference Relaxin protein.

The fusion polypeptides of the invention may have an EC50 value that is such that the ratio of the EC50 of said fusion polypeptide over the EC50 of a reference Relaxin protein is comprised between 1 and about $10^5$, between 1 and about $10^4$, between about 1 and about $10^3$, between about 1 and about 100, between about 1 and about 50, between about 1 and about 20, between about 1 and about 15, between about 1 and about 10, or between about 1 and about 5. Alternatively, a fusion polypeptide of the invention may have an EC50 value that is such that the ratio of the EC50 of said fusion polypeptide over the EC50 of a reference Relaxin protein is comprised between about $10^{-5}$ and about 1, between about $10^{-4}$ and about 1, between about $10^{-3}$ and about 1, between about 1/100 and about 1, between about 1/50 and about 1, between about 1/20 and about 1, between about 1/15 and about 1, between about 1/10 and about 1, between about 1/5 and about 1. In certain embodiments, the ratio of the EC50 value of the fusion polypeptide of the invention over the EC50 value of the reference Relaxin protein is comprised between about $10^{-5}$ and about $10^5$.

In some embodiments, the Relaxin fusion polypeptides have an EC50 value of between about $1.10^{-11}$ and about $1.10^{-7}$ M, for instance between about $1.10^{-10}$ and about $1.10^{-8}$ M, or between about $1.10^{-10}$ and about $8.10^{-9}$ M, or between about $1.10^{-10}$ and about $5.10^{-9}$ M or between about $1.10^{-10}$ and about $1.10^{-9}$ M.

The linker polypeptide L of the fusion polypeptides is at least 15 amino acid residues in length. In some embodiments, the linker polypeptide L is at least 16, 17, 18, 19 or 20 amino acid residues in length. The linker polypeptide L can be of 15 to 30 amino acid residues in length, for instance the linker polypeptide L can be of 15 to 25 amino acid residues in length or of 15 to 20 amino acid residues in length. In a particular embodiment, the linker polypeptide L does not have an amino acid sequence length of 102 amino acids. In another embodiment, said linker polypeptide L has an amino acid sequence length of less than 100, less than 90, less than 80, less than 70, less than 60, or less than 50 amino acids.

The linker polypeptide L can be composed of any amino acid. In some embodiments, the linker polypeptide L comprises glycine and serine residues such as those described in Chen et al., 2013. In further embodiments, the linker polypeptide L comprises the motif (GGGGS)n (repeats of SEQ ID NO. 58), wherein n may be between 1 and 5, for instance wherein n is 4. In other embodiments, the linker polypeptide L comprises or consists of the sequence GGGGSGGGGSGGGGS (SEQ ID NO. 57). In alternative embodiments, the linker polypeptide L comprises or consists of the sequence A(EAAAK)nA (SEQ ID NO. 59), wherein n is 5, as described in Chen et al., 2013.

The linker polypeptide L may have an amino acid sequence that differs from Relaxin C peptide, in particular from human Relaxin 2 C peptide of amino acid sequence SEQ ID NO. 48. In particular, the linker polypeptide L may have less than 80%, less than 70%, less than 60%, less than 50%, less than 40% identity with a Relaxin C peptide, such as human Relaxin 2 C peptide of amino acid sequence SEQ ID NO. 48.

The linker polypeptide L may be an artificial polypeptide, e.g. a polypeptide that is synthesised by chemical peptide synthesis.

The fusion polypeptides of the invention also comprise a half-life extending moiety. Thus, in some embodiments the fusion polypeptides of the invention have an extended half-life compared to the corresponding reference Relaxin. It will be recognised that an extended half-life is advantageous, as it permits the therapeutic proteins to be administered according to a safe and convenient dosing schedule, e.g. lower doses that can be administered less frequently. Moreover, the achievement of lower doses may provide further advantages such as the provision of an improved safety profile and/or the activation of multiple mechanisms of action in vivo.

The inventors have shown that fusion polypeptides of the invention having a half-life extending moiety possess Relaxin activity and at the same time have extended half-lives compared to reference Relaxin. For example, the inventors have shown that fusion polypeptides having a half-life extending moiety according to some embodiments of the invention have a half-life of at least 2 days in rat and mouse models (see Examples 5 and 6). In comparison, the half-life of human Relaxin 2 following IV administration is about 0.09+/−0.04 hours, i.e. 5.4+/−2.4 minutes in humans (Chen et al. 1993).

As used herein, the term "half-life" is used to refer to the time taken for the concentration of fusion polypeptide in plasma to decline to 50% of its original level. The "half-life" of a polypeptide in plasma may depend on different factors such as the size of the polypeptide, its stability, its clearance rate, turnover rate, in vivo proteolytic degradation, the rate of absorption by the body or specific tissues, etc. Methods to determine the half-life of proteins are known in the art and are described in the Examples below.

The half-life extending moiety may be attached at the N-terminus or the C-terminus of the fusion polypeptide. In some embodiments, the half-life extending moiety is attached at the N-terminus of the fusion polypeptide. In other embodiments, the half-life extending moiety is attached at the C-terminus of the fusion polypeptide.

In some embodiments, the half-life extending moiety is a proteinaceous half-life extending moiety. The proteinaceous half-life extending moiety may be selected from the group consisting of an Fc region of an immunoglobulin, albumin-binding domain, serum albumin and transferrin. In other embodiments, the half-life extending moiety is an Fc region.

In further embodiments, the half-life extending moiety is a chemical entity that is not a protein or peptide, such as polyethylene glycol (PEG) polymer chains which may be covalently or non-covalently attached to the rest of the fusion polypeptide of the invention. PEGylation, that is the process of attaching said PEG polymer chains to a molecule, can be carried out according to methods well known in the art.

The term "Fc region" defines the C-terminal region of an immunoglobulin heavy chain, which may be generated by papain digestion of an intact antibody. The Fc region of an immunoglobulin generally comprises two constant domains, a CH2 domain and a CH3 domain, and optionally comprises a CH4 domain.

The Fc region may be derived from an immunoglobulin from any species. In some embodiments, the Fc region is derived from a human immunoglobulin. In further embodiments, the Fc region is derived from a human IgG immunoglobulin. In particular embodiments, the Fc region is derived from a human IgG1 immunoglobulin. In other embodiments, the Fc region is derived from a human IgG4 immunoglobulin.

In some embodiments, the Fc region comprises a native Fc sequence, i.e. an amino acid sequence identical to the amino acid sequence found in nature. In alternative embodiments, the Fc region comprises a variant Fc sequence, i.e. an amino acid sequence that differs from the amino acid sequence by at least one amino acid modification. The Fc region may be modified to e.g. increase the affinity of the IgG molecule for the FcRn. PCT publication WO 02/060919 discloses modified immunoglobulins comprising an Fc region having one or more amino acid modifications and is incorporated herein in its entirety by reference. For a Fc region derived from an IgG4 immunoglobulin, the Fc region may also be modified to reduce Fab arm exchange (the dynamic process by which IgG4 antibodies can exchange half-molecules), e.g. by introducing a S228P modification in the IgG4 amino acid sequence, wherein the amino acid numbering is according to the EU index as in Kabat. Methods of making Fc regions with one or more amino acid modifications are known in the art.

In some embodiments, the Fc region comprises a human IgG sequence, in particular a human IgG1 sequence, comprising at least one of the following combinations of amino acid modifications:
(i) Fc-YTE (M252Y, S254T, T256E);
(ii) Fc-FQQ (L234F, L235Q, K3220);
(iii) Fc-TM (L234F, L235E, P331S);
(iv) Fc-YTE-FQQ (M252Y, S254T, T256E, L234F, L235Q, K3220);
(v) Fc-YTE-TM ((M252Y, S254T, T256E, L234F, L235E, P331S),
(vi) Fc-TM-ΔTHT (L234F, L235E, P331S, D221G, K222G, T223G, H224S, T225A),
(vii) Fc-TM-ΔTHTΔK (L234F, L235E, P331S, D221G, K222G, T223G, H224S, T225A, ΔK447),
wherein the amino acid numbering is according to the EU index as in Kabat.

In further embodiments, the Fc region comprises a human IgG4 sequence. In particular the Fc region comprises a human IgG4 sequence wherein a Serine is modified into a Proline at position 228 ("S228P"), wherein the amino acid numbering is according to the EU index as in Kabat, said modified Fc region is abbreviated herewith as "Fc-G4P". In still further embodiments, the Fc region derived from an IgG4 comprises the S228P modification and at least one of the following combinations of amino acid modifications:
(i) Fc-YTE (M252Y, S254T, T256E);
(ii) Fc-FQQ (L234F, L235Q, K3220);
(iii) Fc-TM (L234F, L235E, P331S);
(iv) Fc-YTE-FQQ (M252Y, S254T, T256E, L234F, L235Q, K3220);
(v) Fc-YTE-TM ((M252Y, S254T, T256E, L234F, L235E, P331S),
(vi) Fc-TM-ΔTHT (L234F, L235E, P331S, D221G, K222G, T223G, H224S, T225A),
(vii) Fc-TM-ΔTHTΔK (L234F, L235E, P331S, D221G, K222G, T223G, H224S, T225A, ΔK447), wherein the amino acid numbering is according to the EU index as in Kabat.

The term "EU index as in Kabat" refers to the numbering system of the human IgGI EU antibody described in Kabat et al, Sequences of Immunological Interest, 5th Ed. Public Health Service, National Institutes of Health, Bethesda, Md. (1991). All amino acid positions referenced in the present application refer to EU index positions. For example, both "L234" and "EU L234" refer to the amino acid leucine at position 234 according to the EU index as set forth in Kabat.

According to an aspect of the invention, there is provided a modified immunoglobulin comprising an immunoglobulin constant domain comprising one or more amino acid modifications relative to a wild-type immunoglobulin constant domain, wherein the one or more amino acid modifications are at one or more of positions 234, 235 and 331, wherein the amino acid numbering is according to the EU index as in Kabat. According to another aspect, there is provided a modified immunoglobulin comprising an immunoglobulin constant domain comprising one or more amino acid modifications relative to a wild-type immunoglobulin constant domain, wherein the one or more amino acid modifications are at one or more of positions 234, 235 and 322, wherein the amino acid numbering is according to the EU index as in Kabat. According to another aspect of the invention, there is provided a modified immunoglobulin comprising an immunoglobulin constant domain comprising one or more amino acid modifications relative to a wild-type immunoglobulin constant domain, wherein the one or more amino acid modifications are at one or more of positions 221, 222, 223, 224, 225, and 447, wherein the amino acid numbering is according to the EU index as in Kabat. According to still further aspects of the invention, there is provided a modified immunoglobulin comprising an immunoglobulin constant domain comprising one or more amino acid modifications relative to a wild-type immunoglobulin constant domain, wherein the one or more amino acid modifications are at one or more of positions 221, 222, 223, 224, 225, 234, 235, 331 and 447, wherein the amino acid numbering is according to the EU index as in Kabat. In some embodiments, the one or more amino acid modifications abolish the effector function of Fc region and/or reduce or circumvent cytotoxicity, for example antibody-dependent cell-mediated cytotoxicity (ADCC) and complement-dependent cytotoxicity (CDC).

According to an aspect of the invention, there is provided a modified immunoglobulin comprising an immunoglobulin constant domain comprising one or more amino acid modifications relative to a wild-type immunoglobulin constant domain, wherein the one or more amino acid modifications are at one or more of positions 252, 254 and 256, wherein the amino acid numbering is according to the EU index as in Kabat. In some embodiments, the one or more amino acid modifications increase the half-life of the fusion polypeptide.

In some embodiments, the one or more amino acid modifications are amino acid substitutions.

In other embodiments, the one or more amino acid modifications are amino acid deletions.

In further embodiments, the one or more amino acid substitutions include one or more of: substitution with phenylalanine at position 234, substitution with glutamic acid at position 235 and/or substitution with serine at position 331. In particular embodiments, the modified immunoglobulin comprises the amino acid substitutions of phenylalanine at position 234, glutamic acid at position 235 and serine at position 331. The amino acid numbering mentioned here is according to the EU index as in Kabat.

In further embodiments, the one or more amino acid substitutions include one or more of: substitution with phenylalanine at position 234, substitution with glutamine at position 235 and/or substitution with glutamine at position 322. In particular embodiments, the modified immunoglobulin comprises the amino acid substitutions of phenylalanine at position 234, glutamine at position 235 and glutamine at position 322. The amino acid numbering mentioned here is according to the EU index as in Kabat.

In other embodiments, the one or more amino acid substitutions include one or more of: substitution with tyrosine at position 252, substitution with threonine at position 254 and/or substitution with glutamic acid at position 256. In particular embodiments, the modified immunoglobulin comprises the amino acid substitutions of tyrosine at position 252, threonine at position 254 and glutamic acid at position 256. The amino acid numbering mentioned here is according to the EU index as in Kabat.

In still other embodiments, the one or more amino acid modifications include one or more of: substitution with glycine at position 221, substitution with glycine at position 222, substitution with glycine at position 223, substitution with serine at position 224, substitution with alanine at position 225, and/or deletion of lysine at position 447, wherein the amino acid numbering is according to the EU index as in Kabat.

In still other embodiments, the one or more amino acid modifications include one or more of: substitution with glycine at position 221, substitution with glycine at position 222, substitution with glycine at position 223, substitution with serine at position 224, substitution with alanine at position 225, substitution with phenylalanine at position 234, substitution with glutamic acid at position 235, substitution with serine at position 331, and/or deletion of lysine at position 447, wherein the amino acid numbering is according to the EU index as in Kabat.

It will be understood that the modified immunoglobulin may further comprise other amino acid modifications, such as the other amino acid modifications detailed herein, or any combination thereof.

Methods for attaching the half-life extending moiety to the fusion polypeptide are known in the art. For example, the half-life extending moiety may be attached by chemical conjugation or recombinant technology. The half-life extending moiety may be attached to the fusion polypeptide directly or through a connector polypeptide. The use of a connector polypeptide may be particularly appropriate when the fusion polypeptide comprises a proteinaceous half-life extending moiety such as an Fc region.

The connector polypeptide may be any suitable length, for example between about 1 and 100 amino acids in length, between about 1 and 50 amino acids in length, between about 1 and 25 amino acids in length, between about 1 and 15 amino acids in length or between about 4 and 15 amino acids in length. In some embodiments, the connector is between 4 and 15 amino acids in length. For instance, a connector can be of 4, 5, or 15 amino acids in length. In other embodiments, the connector is between 15 and 25 amino acids in length, for instance a connector can be of 15, 16, 17, 18, 19, 20, 21, 22, 23, 24, or 25 amino acids in length.

The connector polypeptide may comprise any amino acid. Connector polypeptides suitable for the invention may include any of those described in Chen et al., 2013. In some embodiments, the connector comprises glycine and serine residues such as described in Chen et al., 2013. In further embodiments, the connector polypeptide comprises one or more repeats of the motif GGGGS (SEQ ID NO. 58). For example, the connector polypeptide may comprise the sequence GGGGSGGGGSGGGGS (SEQ ID NO. 57). In further embodiments, the connector polypeptide has a Pro-line residue at the C- and/or N-terminal end. In other embodiments, the connector polypeptide has one or more, for instance 1 to 3, alanine residue(s) at the C- and/or N-terminal end. In some embodiments, the connector polypeptide comprises or consists of the same sequence as the linker polypeptide L of the fusion polypeptide.

Examples of connectors include: GGSP (SEQ ID NO. 56), GGGGSGGGGSGGGGS (SEQ ID NO. 57), GGGGSGGGGSGGGGSGGGGS (SEQ ID NO. 69), AAAGGGGSGGGGSGGGGSGGGGSA (SEQ ID NO. 70).

The fusion polypeptides of the invention may be single chain Relaxin fusion polypeptides.

In some embodiments, the fusion polypeptides of the invention have the structure Fc-Cn-A-L-BorFc-Cn-B-L-A wherein A is a Relaxin A chain polypeptide or a variant thereof; B is a Relaxin B chain polypeptide or a variant thereof; L is a linker polypeptide comprising at least 15 amino acids; Cn is a connector polypeptide; and Fc is the Fc region of an immunoglobulin heavy chain.

In some embodiments, the fusion polypeptides of the invention have the structure A-L-B-Cn-Fc or B-L-A-Cn-Fc wherein A is a Relaxin A chain polypeptide or a variant thereof; B is a Relaxin B chain polypeptide or a variant thereof; L is a linker polypeptide comprising at least 15 amino acids; Cn is a connector polypeptide; and Fc is the Fc region of an immunoglobulin heavy chain.

In further embodiments, the fusion polypeptides of the invention are one or more of the fusion polypeptides set forth in Table 1 and FIGS. 1 to 19. In FIGS. 2 to 19, the linker L is indicated by double underlining, the connector Cn is indicated by single underlining, and nucleotide and amino acid substitutions are indicated in bold and by bold underlining.

TABLE 1

Exemplary fusion polypeptides of the invention

| Fusion polypeptide | Figure No. | SEQ ID NO. | SEQ ID NO. of a nucleic acid encoding said fusion polypeptide |
|---|---|---|---|
| Fc_hRLX2_4-15AA | 2 | 2 | 1 |
| Fc-TM_hRLX2_4-15AA | 3 | 4 | 3 |
| Fc-FQQ_hRLX2_4-15AA | 4 | 6 | 5 |
| Fc_YTE-hRLX2_4-15A | 5 | 8 | 7 |
| Fc-YTE-TM_hRLX2_4-15AA | 6 | 10 | 9 |
| Fc-YTE-FQQ_hRLX2_4-15A | 7 | 12 | 11 |
| Fc-G4P_hRLX2_4-15AA | 8 | 14 | 13 |
| Fc_hRLX2_15-15AA | 9 | 16 | 15 |
| Fc-TM_hRLX2_15-15AA | 10 | 18 | 17 |
| Fc-FQQ_hRLX2_15-15AA | 11 | 20 | 19 |
| Fc-YTE_hRLX2_15-15AA | 12 | 22 | 21 |
| Fc-YTE-TM_hRLX2_15-15AA | 13 | 24 | 23 |
| Fc-YTE-FQQ_hRLX2_15-15A | 14 | 26 | 25 |
| Fc-G4P_hRLX2_15-15AA | 15 | 28 | 27 |
| Fc-TMΔTHTΔK_hRLX2_21-15AA | 16 | 62 | 61 |
| Fc-TMΔTHTΔK_hRLX2(BA)_21-15AA | 17 | 64 | 63 |
| hRLX2-Fc-TMΔTHTΔK_15-24AA | 18 | 66 | 65 |
| hRLX2(BA)-Fc-TMΔTHTΔK_15-24AA | 19 | 68 | 67 |

The fusion polypeptides of the invention may be produced by any method known in the art. In some embodiments, the fusion polypeptides of the invention are produced by recombinant expression of a nucleic acid molecule encoding a fusion polypeptide in a host cell.

Accordingly, the present invention provides nucleic acid molecules, e.g. DNA molecules, that encode a fusion polypeptide of the invention, as well as vectors comprising the nucleic acid molecules of the invention, and host cells comprising such nucleic acid molecules and vectors.

Sequences of the nucleic acid molecules of the invention according to some embodiments are set out in FIGS. 2 to 19 and in Table 1.

Methods that are known to those skilled in the art can be used to construct expression vectors containing the nucleic acid molecules of the invention. Suitable vectors include, for example, plasmids, phagemids, phages or viral vectors.

Vectors containing the nucleic acid molecules of the invention may be transferred to a host cell by conventional techniques. Suitable host cells are known in the art. In some embodiments, the host cells are mammalian cells such as HEK293 cells or CHO cells.

The transfected cells may be cultured by conventional techniques to produce the fusion polypeptides of the invention.

Once a fusion polypeptide of the invention has been produced, for example by recombinant expression, it may be purified by any method known in the art. Exemplary protein purification techniques include chromatography (e.g. ion exchange, affinity and/or sizing column chromatography), centrifugation and differential solubility. The present invention provides isolated fusion polypeptides that have been separated from the cell culture, optionally by at least one purification step.

The fusion polypeptides of the invention may be provided in a pharmaceutical composition.

The pharmaceutical compositions of the invention may comprise one or more excipient(s). Pharmaceutically acceptable excipients are known in the art, see for instance Remington's Pharmaceutical Sciences (by Joseph P. Remington, 18th ed., Mack Publishing Co., Easton, Pa.), which is incorporated herein in its entirety.

The present invention encompasses therapies which involve administering the fusion polypeptides of the invention to an animal, in particular a mammal, for instance a human, for preventing, treating, or ameliorating symptoms associated with a disease, disorder, or infection.

Accordingly, the fusion polypeptides or a pharmaceutical composition of the invention may be used in therapy, for example for treating a disease or disorder. Also provided is a method of treating a disease or disorder comprising administering to a subject or patient in need thereof a therapeutically effective amount of the fusion polypeptides of the invention. The use or method may comprise administering a therapeutically effective schedule that has less frequent doses of the fusion polypeptides of the invention than the therapeutically effective dosing schedule of a wild-type Relaxin molecule.

It will be understood that the fusion polypeptides of the invention may be used in the treatment of cardiovascular diseases, for example for the treatment of heart failure.

As used herein, the term "heart failure" includes acute heart failure, chronic heart failure (CHF) and acute decompensated heart failure (ADHF). The term "heart failure" may also include more specific diagnoses such as heart failure with preserved ejection fraction (HFpEF), heart failure with mid-range ejection fraction or heart failure with reduced ejection fraction (HFrEF).

The fusion polypeptides of the invention may also be used in the treatment of kidney disease, lung disease and fibrotic disorders, for example fibrotic disorders of the kidney, heart, lung and liver, and in wound healing (Sherwood, 2004). The fusion polypeptides of the invention may also be used in the reversal of insulin resistance in diabetic patients (Bonner et al., 2013).

The fusion polypeptides and/or pharmaceutical compositions of the invention are suitable for parenteral administration to a subject or patient. In some embodiments the subject or patient is a mammal, in particular a human.

Wild-type human Relaxin 2 has a half-life of minutes in vivo. As a consequence, it has to be administered by continuous intravenous infusion in hospitalized patients and presents severe side effects including blood pressure drop. In contrast, it will be understood that embodiments of the fusion polypeptides and/or pharmaceutical compositions of the invention may be administered by injection, such as by intravenous, subcutaneous or intramuscular injection, to a subject or patient. In some embodiments, the fusion polypeptides and/or pharmaceutical compositions are administered by subcutaneous injection. Administration by injection, such as by subcutaneous injection, offers the advantage of better comfort for the subject or patient and the opportunity to administer to a subject or patient outside of a hospital setting. In some embodiments the fusion polypeptide or pharmaceutical composition is administered by self-administration.

In some embodiments, the fusion polypeptides of the invention have an increased half-life compared to wild-type Relaxin, which permits lower overall exposure based on molar concentration. For example, the fusion polypeptides of the invention may be administered less frequently than wild-type Relaxin, thus providing a more convenient dosing schedule.

The present invention provides a kit comprising the pharmaceutical compositions of the invention. The kit may comprise a package containing the pharmaceutical compositions of the invention and instructions. In some embodiments, the pharmaceutical compositions of the invention are formulated in single dose vials or a container closure system (e.g. pre-filled syringe). Optionally associated with such container(s) can be a notice in the form prescribed by a governmental agency regulating the manufacture, use or sale of pharmaceuticals or biological products, which notice reflects approval by the agency of manufacture, use or sale for human administration.

As used herein, the articles "a" and "an" may refer to one or to more than one (e.g. to at least one) of the grammatical object of the article.

"About" may generally mean an acceptable degree of error for the quantity measured given the nature or precision of the measurements. Exemplary degrees of error are within 20 percent (%), typically, within 10%, and more typically, within 5% of a given value or range of values.

Embodiments described herein as "comprising" one or more features may also be considered as disclosure of the corresponding embodiments "consisting of" such features.

The term "pharmaceutically acceptable" as used herein means approved by a regulatory agency of the Federal or a state government, or listed in the U.S. Pharmacopeia, European Pharmacopeia or other generally recognized pharmacopeia for use in animals, and more particularly in humans.

Concentrations, amounts, volumes, percentages and other numerical values may be presented herein in a range format. It is also to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

In the context of the present disclosure other examples and variations of the fusion polypeptides and methods described herein will be apparent to a person of skill in the art. Other examples and variations are within the scope of the disclosure, as set out in the appended claims.

All documents cited herein are each entirely incorporated by reference herein, including all data, tables, figures, and text presented in the cited documents.

EXAMPLES

Example 1: Constructs

Some DNA constructs were created to express various IgG1-Fc/connector/Relaxin 2 A chain/linker/Relaxin 2 B chain fusion polypeptides. In these constructs, the connector was either 4 amino acids (GGSP) or 15 amino acids (GGGGSGGGGSGGGGS) in length and the linker was 15 amino acids (GGGGSGGGGSGGGGS) in length. The Fc moiety was either native wild-type human IgG1 Fc moiety (abbreviated "hFc-G1") or a mutated form of human IgG1 Fc moiety comprising one or several combinations of the following mutations:
(i) M252Y, S254T, T256E (abbreviated "YTE"). The Fc moiety comprising the YTE mutations is abbreviated "hFc-G1-YTE".
(ii) L234F, L235Q, K322Q (abbreviated "FQQ"). The Fc moiety comprising the FQQ mutations is abbreviated "hFc-G1-FQQ". The Fc moiety comprising both the YTE and the FQQ mutations is abbreviated "hFc-G1-YTE-FQQ".
(iii) L234F, L235E, P331S (abbreviated "TM"). The Fc moiety comprising the TM mutations is abbreviated "hFc-G1-TM". The Fc moiety comprising both the YTE and the TM mutations is abbreviated "hFc-G1-YTE-TM".

In these constructs, the A chain was the native wild-type A chain of human Relaxin 2 (SEQ ID NO. 42) and the B chain was a B chain variant (SEQ ID NO. 46) corresponding to the native wild-type B chain of human Relaxin 2 (SEQ ID NO. 44) lacking the first amino acid (D).

The DNA for the fusion polypeptides with native human IgG-1 Fc sequence was synthesized by GeneArt® (Regensburg, Germany) and supplied as plasmid DNA. The human IgG1 Fc gene sequence was removed from GeneArt® plasmid by restriction enzyme digestion with XbaI and NotI and cloned into the pHOE vector using the same restriction digestions with XbaI and NotI. The pHOE vector was designed for expressing the heavy chain of human antibody IgG1. This cloning strategy removed all the vector antibody sequence but preserved the intron between the signal peptide and Fc sequence.

The required human IgG1 Fc mutations (YTE, FQQ and TM) occur within a 300 bp KasI restriction fragment located within the human IgG1 Fc. The KasI fragment with the appropriate mutations was synthesized by IDT (Coralville, Iowa) as a GeneBlock. The human relaxin-2 plasmid with native Fc fusion was digested with KasI and the KasI GeneBlock was cloned in pHOE vector using the NEBuilder HiFi Assembly Master Mix (NEB# E2621S) for seamless cloning.

Fc-hRLX2-4-15AA and Fc-hRLX2-15-15AA

The Fc-hRLX2-4-15AA and Fc-hRLX2-15-15AA gene sequences were synthesized by GeneArt® (Regensburg, Germany) and supplied as plasmid DNA. The gene sequences were removed from GeneArt® plasmid by restriction enzyme digestion with XbaI and NotI and independently cloned into the pHOE vector using the same restriction sites, leading to pOE-Fc-hRLX2-4-15AA plasmid and pOE-Fc-hRLX2-15-15AA plasmid, respectively. The pHOE vector is used for expressing the heavy chain portion of human IgG1. This cloning strategy removed all the vector antibody sequence but preserved the intron between the signal peptide and Fc sequence.

Fc-YTE-hRLX2-4-15AA and Fc-YTE-hRLX2-15-15AA

The YTE mutations (M252Y/S254T/T256E) occur within a 300 bp KasI fragment located in the human IgG1 Fc. The KasI fragment with appropriate mutations was synthesized by IDT (Coralville, Iowa) as a GeneBlock. The pOE-Fc-hRLX2-4-15AA plasmid and pOE-Fc-hRLX2-15-15AA plasmid were independently digested with KasI and the KasI GeneBlock was cloned into the above plasmids using the NEBuilder HiFi Assembly Master Mix (NEB# E2621S) for seamless cloning.

Fc-YTE-TM-hRLX2-4-15AA and Fc-YTE-TM-hRLX2-15-15AA

The YTE-TM mutations (M252Y/S254T/T256E, L234F/L235E/P331S) occur within a 300 bp KasI fragment located in the human IgG1 Fc. The KasI fragment with appropriate mutations was synthesized by IDT (Coralville, Iowa) as a GeneBlock. The pOE-Fc-hRLX2-4-15AA plasmid and pOE-Fc-hRLX2-15-15AA plasmid were independently digested with KasI and the KasI GeneBlock was cloned into the empty vectors using the NEBuilder HiFi Assembly Master Mix (NEB# E2621S) for seamless cloning. The 3' KasI site is destroyed in these plasmids.

Fc-YTE-FQQ-hRLX2-4-15AA and Fc-YTE-FQQ-hRLX2-15-15AA

The YTE-FQQ mutations (M252Y/S254T/T256E, L234F/L235Q/K322Q) occur within a 300 bp KasI fragment located in the human IgG1 Fc. The KasI fragment with appropriate mutations was synthesized by IDT® (Coralville, Iowa) as a GeneBlock. The pOE-Fc-hRLX2-4-15AA plasmid and pOE-Fc-hRLX2-15-15AA plasmid were independently digested with KasI and the KasI GeneBlock was cloned into the empty vectors using the NEBuilder HiFi Assembly Master Mix (NEB# E2621S) for seamless cloning.

Some other DNA constructs were created to express Relaxin 2 as a Fc fusion polypeptide with connectors longer than 15 amino acids in length, as well as Relaxin 2 fusion proteins comprising a Fc part situated at either the N- or C-terminus of the fusion protein, and with two possible orientations for the relaxin chains (A-L-B or B-L-A).

In these other constructs, the connector was either 21 amino acids (GGGGSGGGGSGGGGSGGGGGS) or 24 amino acids (AAAGGGGSGGGGSGGGGSGGGGSA) and the linker was 15 amino acids (GGGGSGGGGSGGGGS) in length.

The Fc moiety was a mutated form of human IgG1 Fc moiety, abbreviated "hFc-G1-TM-ΔTHT-ΔK", comprising the following mutations:
(i) L234F, L235E, P331S (abbreviated "TM"),
(ii) D221G, K222G, T223G, H224S, T225A (abbreviated "ΔTHT"),
(iii) Deletion of K447 (abbreviated "ΔK").

In these other constructs, the A chain was the native wild-type A chain of human Relaxin 2 (SEQ ID NO. 42) and the B chain was a B chain variant (SEQ ID NO: 46) corresponding to the native wild-type B chain of human Relaxin 2 (SEQ ID NO: 44) lacking the first amino acid (D).

The DNA inserts for constructs Fc-TMΔTHTΔK_hRLX2_21-15AA (construct 15 in FIG. 1) and hRLX2-Fc-TMΔTHTΔK_15-24AA (construct 17 in FIG. 1) were generated by PCR amplification of the DNA molecule of construct 8 in FIG. 1 (Fc_hRLX2_15-15AA). The DNA inserts for constructs (Fc-TMΔTHTΔK_hRLX2 (BA)_21-15AA (construct 16 in FIG. 1) and hRLX2(BA)-Fc-TMΔTHTΔK_15-24AA (construct 18 in FIG. 1) were synthesized by GenScript® (Piscataway, USA) and then amplified by PCR before digestion with restriction enzymes. The PCR amplicons for constructs 15 and 16 were digested by the restriction enzymes BamHI and EcoRI. The PCR amplicons for constructs 17 and 18 were digested by the restriction enzymes NgoMIV and NotI. The digested inserts were ligated into the plasmid pepFc (derived from pOE). The plasmids were digested with BamHI and EcoRI for fusion at the C-terminus of the Fc; or with NgoMIV and NotI for fusion at the N-terminus. The Quick ligation kit (NEB) was used to ligate the DNA inserts into the plasmids.

The Relaxin Fc fusions were expressed in CHO cells by standard methods as described in Daramola, et al., 2014. The fusion proteins were purified from the supernatant using an AKTAxpress system by affinity chromatography with Mab-SelectSuRe columns. Columns were equilibrated in 1xDPBS (Gibco, Invitrogen. Cat No: 14190-094). After loading of the supernatant, the column was washed with 1xDPBS to remove molecules which do not bind specifically to the column. Elution of the Fc fusions was achieved using a solution of 0.1M glycine at pH2.7. The purified proteins were buffer exchanged to 1xDPBS. The protein concentrations were determined using absorption at 280 nm. The purified proteins were then analysed by SDS-PAGE and SEC-HPLC (TSKgel G3000SWXL column) to assess purity and monomeric content.

FIG. 1 provides a schematic representation and abbreviated names of some of the Fc human Relaxin 2 fusion polypeptides of the invention.

Example 2: In Vitro Activity of Fc-Relaxin-2 Fusion Polypeptides (In Vitro cAMP Assay)

An in vitro cell-based assay was used to measure the activity of Relaxin 2 fusion polypeptides generated in Example 1. The assay measured the ability of the fusion polypeptides (Fc-hRLX2-4-15AA and Fc-hRLX2-15-15AA) to stimulate cAMP production.

The HitHunter® cAMP assay from DiscoverX (catalogue number 90-0075, Fremont, Calif.) was used to measure the cAMP produced after ligand stimulation with the Relaxin 2 fusion polypeptides. The assay was performed based on the manufacturer's protocol. Briefly, cells from an RXFP1 expression cell line, CHO-K1 RXFP1 Gs, (DiscoverX catalogue number 95-0127C2, Fremont, Calif.), were seeded at 20,000 cells/well in 100 μL/well of F12K media (Gibco, Cat#21127022), supplemented with 1% antibiotics, 0.8 mg/ml Geneticin, and 10% fetal bovine serum using a MultiDrop Combi dispenser (Thermo Scientific, Waltham, Mass.) and allowed to attach overnight at 37° C. in 5% $CO_2$ incubator. Following incubation, plates were washed with 100 μL/well of F12K serum-free media. Wash media was removed and plates were ready to assay after addition of 20 μL/well of F12K serum-free media. For testing sample preparation, in a separate 96-U bottom plate three-fold dilutions of Relaxin 2 fusion polypeptides, and recombinant human Relaxin-2 (R&D Systems, catalogue number 6586-RN-025) as positive control, were made in replicates. From the diluted and titrated sample plate, 10 μL from each well was transferred into the assay plate, incubated at 37° C. for 30 minutes. Post incubation, 10 μL/well of antibody reagent (from the HitHunter® kit) was added, immediately followed by 40 μL/well of cAMP working detection solution (made as directed in the HitHunter® kit) and incubated at room temperature in the dark for 1 hour. Next, 40 μL of cAMP solution A (from the HitHunter® kit) was added. The assay plate was incubated for 3 additional hours at room temperature in the dark. The assay plate was read on a standard luminescence plate reader (EnVision, PerkinElmer) at 0.1 to 1 second/well. Data analysis was performed using statistical analysis software (GraphPad Prism, V6).

Results and Conclusion

The biological activity of the tested constructs is provided in Table 2 and in FIGS. 16 (single experiments) and 17 (repeated experiments).

The average EC50s for both the recombinant human Relaxin-2 and fusion polypeptides from several assays has been summarized in Table 2.

TABLE 2

Biological activity of some Relaxin 2 fusion constructs

| Construct | EC50 (M) |
|---|---|
| rhRLX2 (R&D Systems, catalogue number 6586-RN-025) | 1.06E−10* |
| Fc_hRLX2_4-15AA | 9.32E−10* |
| Fc_hRLX2_15-15AA | 9.84E−10* |
| Fc-YTE-TM_hRLX2_15-15A | 5.39E−09# |
| Fc-YTE-FQQ_hRLX2_15-15A | 4.56E−09# |

*Values are mean values from 5 independent repeats
Values are mean values from 3 independent repeats These results show that the Relaxin 2 fusion polypeptides of the invention are biologically active, as seen using an in vitro cell-based assay.

Due to the variability of the in vitro cell based cAMP stimulation assay, recombinant human relaxin-2 is always used in each assay as a positive control. As a further comment, the activity ratio calculation is only meaningful for each assay where both the fusion peptide and recombinant human relaxin-2 were included. The activity of the fusion polypeptide (EC50) is compared to the activity of the recombinant human relaxin-2 (EC50) to derive the ratio, which is about 10 or about 50, when the average EC50 values obtained in several independent repeats are used to determine said ratio. In contrast, calculated on the basis of EC50 values obtained within the same assay (one repeat), the ratio is lower, typically comprised between about 10 and 20, or about 15 (see, for instance, FIG. 20).

Example 3: Specificity of Fc-Relaxin-2 Fusion Polypeptides for Relaxin-2 Receptor The relaxin family peptides produce their physiological effects by activating a group of four G protein-coupled receptors (GPCRs); which can be stimulated (Gs) or inhibited (Gi) by their ligands. Relaxin 2 binds specifically to the receptor RXFP1.

To check the binding and activation specificity of Relaxin 2 fusion polypeptides for the RXFP1 receptor, the following cell lines were purchased from DiscoverX (Fermont, Calif.):
  cAMP Hunter™ CHO-K1 RXFP2 Gs cell line (Catalogue number 95-0140C2, DiscoverX), ligand is INSL3 (Catalogue number 4544-NS, R&D System)
  cAMP Hunter™ CHO-K1 RXFP3 Gi cell line (Catalogue number 95-0102C2, DiscoverX), ligand is Relaxin-3 (Catalogue number TP723377, Origene)
  cAMP Hunter™ CHO-K1 RXFP4 Gi cell line (Catalogue number 95-0134C2, DiscoverX), ligand is INSL5 (Catalogue number TP723251, Origene)
  cAMP Hunter™ CHO-K1 ADCYAP1R1 Gs/Gq cell line (Catalogue number 95-0064C2, DiscoverX), ligand is PACAP1-27 (Catalogue number 1183, R&D Systems).

RXFP2 cell lines naturally overexpress Gs wild-type GPCRs RXFP2 and are designed to detect the increase in intracellular cAMP levels in response to agonist stimulation. RXFP3 and RXFP4 cell lines naturally overexpress Gi wild-type GPCRs RXFP3 and RXFP4, respectively, and are designed to detect the decrease in intracellular cAMP levels in response to antagonist stimulation. CHO-K1 ADCYAP1R1 is an unrelated GPCR overexpression cell line and is used as assay control.

These cell lines were used to measure the activity of IgG1-Fc human relaxin fusion polypeptides with the HitHunter® cAMP XS+ chemiluminescent detection kit from DiscoverX (Catalogue number 90-0075, Fremont, Calif.). cAMP assays were carried out as described in Example 2, except for cell lines RXFP3 and RXFP4, in which 25 µM or 20 µM Forskolin (Catalogue number 1099, R&D Systems) respectively, was added to the dilution plate and serum-free medium to increase intracellular levels of cAMP as the ligands used in the assay will inhibit cAMP production. Experiments were performed at least twice.

Results and Conclusion

The results are shown in FIG. 22. The Relaxin 2 fusion polypeptides tested have a minimal activity in the RXFP2 expression cell line, and are not active in the other related RXFP expression cell lines (RXFP3 and RXFP4). As expected, no activity was observed in the ADCYAP1R1 Gs/Gq cell line.

Example 4. Fc-Relaxin-2 Fusion Polypeptides Induce VEGF Expression in THP-1 Cells The ability of the Relaxin 2 fusion polypeptides to induce the expression of VEGF, a known downstream target of Relaxin 2 (Xiao et al., 2013), was assayed. The expression of VEGF RNA in THP-1 cells (Catalogue number TIB-202, ATCC) was analyzed by quantitative real-time PCR. A total of $10^6$ cells/ml was seeded in a 24-well flat bottom plate (Catalogue number 353226, Corning) in 400 µl test media (RPM1-1640 without phenol red, 0.5% FBS, 1% Pen/Strep and 0.05 mM of 2-mercaptoethanol). After 24h incubation at 37° C., 5% $CO_2$, human relaxin-2 (Catalogue number 3956-RN, R&D Systems) or Fc-hRelaxin-2 fusion polypeptides, were added to the cells in the plate for 2.5 h at 37° C. RNA isolation and purification from THP-1 cells was performed using Qiagen's QiaShredder (Catalogue number 79656, Qiagen) and RNA Plus Mini Kit (Catalogue number 74134, Qiagen), following the manufacturer's protocol. The mRNA concentrations were measured by NanoDrop (Thermofisher) and samples were normalized to the same starting concentration (range between RT-PCR set up; 50-20 ng/µl). RT-PCR samples were prepared using Express One-Step Superscript qRT-PCR kit (Catalogue number 11791-200, Invitrogen) and primer/probe sets were as follows: VEGFA human (Hs00900055_m1, catalogue number 4331182, ThermoFisher Scientific) and GAPDH human (Hs02758991_g1, catalogue number 4331182, ThermoFisher Scientific). RT-PCR reactions were performed using 7900HT Fast Real-Time PCR machine with cycle set up of: 1 cycle of 50° C. for 15 min for cDNA synthesis, 1 cycle at 95° C. for 20 sec in Taq activation and 40 cycles at two temperatures of 95° C. for 1 sec and 60° C. for 20 sec for qPCR. The relative fold change in VEGF mRNA level was calculated by the comparative Ct method using GAPDH expression for normalization. Results were calculated as fold changes over no treatment control. Experiments were performed in triplicates with an n>2. Data was analyzed by paired two tailed t-test utilizing Prism GraphPad, V6.

Results and Conclusion

As shown in FIG. 23 (top), the Relaxin 2 fusion polypeptides tested significantly stimulate the VEGF transcripts in THP-1 cells as compared to a mock "no treatment" control at concentrations of 5 ng/ml, 50 ng and 80 ng/ml. Similarly, commercially available recombinant human relaxin 2 (R&D Systems) also significantly increased the VEGF transcripts in THP-1 cells as compared to "no treatment" control cells, at a concentration of 0.01, 0.06, and 10 ng/ml. In order to make a comparison with human relaxin 2, the Fc Relaxin 2 fusion polypeptide concentration was adjusted based on molecular weight difference (6×) and reduction of activity seen in the cAMP assay (10-15 fold).

FIG. 23 (bottom) shows that the Relaxin 2 fusion polypeptides tested significantly stimulate the VEGF transcripts in THP-1 cells as compared to a mock "no treatment" control.

Example 5: PK Profile of Some Fc-Relaxin 2 Fusion Polypeptides

The pharmacokinetic (PK) profiles of some Relaxin 2 fusion polypeptides of the invention were determined using a Relaxin ELISA assay. The rat in vivo PK profiles were determined for the following fusion polypeptides: Fc_hRLX2_4-15AA and Fc_hRLX2_15-15AA.

SureBlue™ TMB Substrate (KPL, 52-00-01. Ready-to-use SureBlue™ TMB Microwell Peroxidase Substrate) and TMB Stop Solution (KPL, 50-85-05) were used to develop the assays. Fc_hRLX2_4-15AA and Fc_hRLX2_15-15AA fusion polypeptides were administered to 8-week-old Wistar rats (Charles River) by the intravenous (IV) or subcutaneous (SC) route at 4 mg/kg. Blood samples were collected at 5 minutes, 30 minutes, 3 hours, 8 hours, 1 day, 2 days, 3 days, 4 days, 7 days, 9 days, 14 days and 21 days post drug administration for the IV route, and at 8 hours, 1 day, 2 days, 3 days, 4 days, 7 days, 9 days, 14 days and 21 days post drug administration for the SC route. Samples were collected into a tube containing EDTA and placed on ice immediately. Samples were centrifuged for 15 minutes at 1000×g within 30 minutes of collection. Aliquoted samples were stored at ≤−20° C. and later tested by ELISA. The half-life was assessed using an Fc capture and Relaxin detection ELISA assay (using the polyclonal antibody from R&D Systems Relaxin detection ELISA kit, Catalogue number DRL200).

Results and Conclusion

FIG. 24 shows the in vivo PK profile of Fc_hRLX2_4-15AA following either subcutaneous (SC) or intravenous (IV) administration in rats. Following SC administration, the peak plasma concentration was achieved within 8 to 24 hours. The mean terminal half-life estimated from non-compartmental analysis was 2.46 days for the IV dose group and 3.21 days for the SC dose group.

FIG. 25 shows the in vivo PK profile of Fc_hRLX2_15-15AA following either SC or IV administration in rats. Following SC administration, the peak plasma concentration was achieved within 8 to 24 hr. The mean terminal half-life estimated from non-compartmental analysis was 3.59 days for the IV dose group and 3.75 days for the SC dose group.

In comparison, the half-life of human Relaxin 2 following IV administration is about 0.09+/−0.04 hours, i.e. 5.4+/−2.4 minutes in humans (Chen et al. 1993).

Example 6: PK Study in FcRn Transgenic Mouse

The extended half-life offered by the YTE mutations (M252Y/S254T/T256E) present in the Fc-fusion polypeptides is confirmed by a PK profile study carried out for the Fc-YTE-hRLX2-15-15AA, Fc-YTE-FQQ-hRLX2-15-15AA and Fc-YTE-TM-hRLX2-15-15AA fusion polypeptides administered either intravenously or subcutaneously, at a dose of 6 mg/kg, in an FcRn transgenic mouse generated in-house. The extended half-life was assessed using an Fc capture and Relaxin detection ELISA assay (using the polyclonal antibody from R&D Systems Relaxin detection ELISA kit, Catalogue number DRL200).

FIG. 26 shows the mouse in vivo PK profile of Fc_hRLX2_15-15AA following either SC or IV administration. The mean terminal half-life was approximately 26.5% greater in the SC dose group compared to the IV dose group.

FIG. 27 shows the mouse in vivo PK profile of Fc_hRLX2_15-15AA following SC administration at a dose of 1 mg/kg, 6 mg/kg or 30 mg/kg. Peak serum concentration was reached between 24-72 hours following SC administration. The mean terminal half-life ranged from 4.59 to 7.06 days. The dose-normalized Cmax decreased with an increase in dose.

Example 7: In Vitro Activity of Some Fc-Relaxin-2 Fusion Polypeptides in Human and Mouse Cell Lines and RXFP2 Selectivity (in Cell-Based cAMP Activity Assay)

Some of the Fc-Relaxin-2 fusion polypeptides of the invention (Fc_hRLX2_15-15AA, Fc-TMΔTHTΔK_hRLX2_21-15AA, Fc-TMΔTHTΔK_hRLX2(BA)_21-15AA, hRLX2-Fc-TMΔTHTΔK_15-24AA, hRLX2(BA)-Fc-TMΔTHTΔK_15-24AA) produced as described in Example 1 were tested for biological activity, e.g., stimulation of one or more cellular receptor responses, by the following methods.

Stable CHO cell lines expressing human or mouse RXFP1 receptor, or human RXFP2 were purchased from DiscoverX and used to test receptor specificity. The cell lines used were as follows: cAMP Hunter™ CHO-K1 RXFP1 Gs cell line (Catalogue number 95-0127C2, DiscoverX), cAMP Hunter™ CHO-K1 RXFP2 Gs cell line (Catalogue number 95-0140C2, DiscoverX), cAMP Hunter™ CHO-K1 mRXFP1 Gs cell line (Catalogue number 95-0180C2, DiscoverX). Activation of these receptors results in downstream production of cAMP second messenger that can be measured in a functional activity assay.

Routine cAMP assays were performed using bovine serum albumin (BSA)-based assay buffer: Hanks Balanced Salt Solution (Sigma # H8264) supplemented with 0.1% BSA (Sigma # A9418) and 0.5 mM IBMX (Sigma #17018), adjusted to pH 7.4 with 1 M NaOH. A frozen cryo-vial of cells expressing the receptor of interest was thawed rapidly in a water-bath, transferred to pre-warmed cell media and spun at 240×g for 5 minutes. Cells were re-suspended in cell media at an optimized concentration (e.g., hRXFP1 at 3.33× $10^4$ cells/ml).

30 µL cell suspension was added to Poly-D-Lysine-coated 384-well plates (Greiner #781946) and allowed to adhere overnight. The next day the media was flicked out of the plates and replaced with 5 µL assay buffer. Eleven-point serial dilutions of test recombinant peptide/Fc fusion samples were added to the cells using a non-contact liquid dispenser (ECHO™, Labcyte). All sample dilutions were made in duplicate. An additional 5 µL assay buffer was added to each well and the plates incubated at room temperature for 30 minutes.

cAMP levels were measured using a commercially available cAMP dynamic 2 HTRF kit (Cisbio, Cat #62AM4PEJ), following the two-step protocol as per manufacturer's recommendations. In brief; anti-cAMP cryptate (donor fluorophore) and cAMP-d2 (acceptor fluorophore) were made up separately by diluting each ½₀ in conjugate & lysis buffer provided in the kit. 5 µL anti-cAMP cryptate was added to all wells of the assay plate, and 5 µL cAMP-d2 added to all wells except non-specific binding (NSB) wells, to which conjugate and lysis buffer was added. Plates were incubated at room temperature for one hour and then read on an Envision (Perkin Elmer) using excitation wavelength of 320 nm and emission wavelengths of 620 nm & 665 nm. Data was transformed to % Delta F as described in manufacturer's guidelines and then transformed to percent activation of maximal native agonist response and analysed by 4-parameter logistic fit to determine $EC_{50}$ values.

The results are compared to corresponding results for recombinant human Relaxin-2 (Catalogue number 6586-RN, R&D Systems) in the case of hRXFP1 cells, mRelaxin-1 (Catalogue number 6637-RN, R&D Systems) in mRXFP1 cells or INSL-3 (Catalogue number 4544-NS, R&D Systems) in hRXFP2 cells. We used unconstrained 4 parameter logistic fit of data, curve mid-point to determine EC50.

Results and Conclusion

The biological activity of the tested fusion polypeptides is provided in Table 3 and the results of one representative assay for each polypeptide are presented in FIG. 28.

Due to the variability of the in vitro cell based cAMP stimulation assay, recombinant human Relaxin-2 is always used in each assay as a positive control.

The average EC50s for both the recombinant human Relaxin-2 and fusion polypeptides from several assays has been summarized in Table 3.

TABLE 3

Biological activity of some Relaxin-2 fusion constructs

| Construct | hRXFP1 EC50 (M) | hRXFP2 EC50 (M) | mRXFP1 EC50 (M) |
|---|---|---|---|
| rhRLX2 | 1.38E−10*** | 1.46E−07* | 6.68E−11*** |
| Fc_hRLX2_15-15AA | 1.84E−09** | >9.32E−06* | 1.51E−09** |
| Fc-TMΔTHTΔK_hRLX2_21-15AA | 2.60E−09* | >6.78E−06* | 2.52E−09* |
| Fc-TMΔTHTΔK_hRLX2(BA)_21-15AA | 1.56E−08** | >8.22E−06** | 8.82E−09** |
| hRLX2-Fc-TMΔTHTΔK_15-24AA | 4.97E−09* | >3.09E−07* | 2.23E−09* |
| hRLX2(BA)-Fc-TMΔTHTΔK_15-24AA | 1.13E−09* | >4.33E−06* | 8.78E−10* |

*Values are mean values from 1 independent repeat
**Values are mean values from 2 independent repeats
***Values are mean values from 3 independent repeats These results show that:
The Relaxin-2 fusion polypeptides tested, comprising either the Fc moiety attached at the N-terminus of the Relaxin fusion polypeptide or at the C-terminus of the Relaxin fusion polypeptide, are biologically active.
The Relaxin-2 fusion polypeptides tested, comprising either chains orientations (B-A or A-B), are biologically active.
Selectivity between RXFP1 and RXFP2 is retained for all Fc-Relaxin-2 fusion polypeptides tested.
The results also show that the Relaxin-2 fusion polypeptides tested have similar species cross-reactivity between human and mouse than human Relaxin-2. In particular, they show that fusion to a Fc domain does not affect species cross-reactivity of human Relaxin-2.

Example 8: Fc_hRLX2_15-15AA Prevents Isoproterenol-Induced Cardiac Hypertrophy in Mice A total of 6 study groups with n=8 mice (C57BL/6J male mice) per group were performed. The groups were: vehicle, Fc_hRLX2_15-15AA, isoproterenol, isoproterenol+enalapril, isoproterenol+recombinant human relaxin 2, and isoproterenol+Fc_hRLX2_15-15AA. Drugs and vehicle were delivered by Alzet minipumps (model 1002; rate: 0.25 μl/hr (±0.05), 6 μl one day @37° C.) or subcutaneous injection for Fc_hRLX2_15-15AA.

Isoproterenol was made as follows: A 500 mM solution (123.9 mg/ml) freshly in 0.0002% Na-Asc saline, 0.22 μM filtered). The final [Iso] concentration in minipump: 15 mg/kg/day=15 mg/247.72/6 μl/1000 g=10.1 mM per gram of body weight (BW). Vehicle was 0.0002% Na-ascorbate, Sigma catalog# A7631.

Enalapril was made as follows: Enalapril is used as maleate salt, MW of 492.52, Sigma catalog# E6888. A 200 mM stock solution (98.5 mg/ml) freshly in methanol, 0.22 μM filtered. The final concentration in minipump: 2.5 mg/kg/day=2.5 mg/492.52/6 μl/1000 g=0.846 mM per gram of body weight (BW), i.e., one minipump for 30 gram of mouse will need 19.0 μl of 200 mM Ena (150 μl×0.846/200 mM×30 g BW).

Isoproterenol+Enalapril: Isoproterenol and enalapril made as described above were included in the pump.

The six groups and dosing are given in Table 4.

TABLE 4

| Group | Test Substance | Dose |
|---|---|---|
| 1 | Vehicle | — |
| 2 | Fc_hRLX2_15-15AA | 30 mg/kg (SC, day 0 and day 7) + minipump for vehicle |

TABLE 4-continued

| Group | Test Substance | Dose |
|---|---|---|
| 3 | Isoproterenol (ISO) | 15 mg/kg/day |
| 4 | ISO + Enalapril | 15 mg/kg/day + 2.5 mg/kg/day |
| 5 | ISO + rhRLX2 | 15 mg/kg/day + 500 ug/kg/day |
| 6 | ISO + Fc_hRLX2_15-15AA | 15 mg/kg/day + 30 mg/kg (SC, day 0 and day 7) |

At the end of the study, body weight, heart weight, lung weight, and tibia length were measured. Additionally, histology and collagen assays were performed using the heart samples.

Fibrosis was measured based on the detection of hydroxyproline (Total collagen assay, QuickZyme Biosciences). Histology (H & E and Masson Trichrome) was also carried out on formalin treated heart tissue following 2 weeks of treatments.

Results and Conclusion

FIG. 29A shows the heart weight (HW) to tibia length (TL) ratio and FIG. 29B shows collagen content.

Treatment with isoproterenol resulted in a significant increase in cardiac hypertrophy and fibrosis compared to vehicle or Fc_hRLX2_15-15AA alone, as indicated by the increase in HW/TL and collagen content (FIG. 29 A, B).

The increase in cardiac hypertrophy and fibrosis observed with isoproterenol was significantly attenuated when isoproterenol was administered concomitantly with enalapril, rhRLX2 or Fc_hRLX2_15-15AA (FIG. 29 A, B).

The data from the histology study were consistent with the collagen and hypertrophy measurements (data not shown).

REFERENCES

Bathgate, R. A., M. L. Halls, E. T. van der Westhuizen, G. E. Callander, M. Kocan, and R. J. Summers. 2013. Relaxin family peptides and their receptors. Physiol Rev 93:405-80.

Bonner, J. S., Lantier, L., Hocking, K. M., Kang. L., Owolabi, M., James, F. D., Bracy, D. P., Brophy, C. M. and Wasserman, D. H. 2013. Relaxin Treatment Reverses Insulin Resistance in Mice Fed a High-Fat Diet. Diabetes. 62(9): 3251-3260.

Chen, S. A., Perlman, A. J., Spanski, N., Peterson, C. M., Sanders, S. W., Jaffe, R., Martin, M., Yalcinkaya, T., Cefalo, R. C., Chescheir, N. C. et al. 1993. The pharmacokinetics of recombinant human relaxin in nonpregnant women after intravenous, intravaginal, and intracervical administration. Pharm Res. 10(6):834-8.

Chen X., Zaro J. L., Shen W. C. 2013. Fusion protein linkers: property, design and functionality. Adv Drug Deliv Rev. 65(10):1357-69.

Claasz, A. A., Bond, C. P., Bathgate, R. A., Otvos, L., Dawson, N. F., Summers, R. J., Tregear, G. W, Wade, J. D. 2002. Relaxin-like bioactivity of ovine Insulin 3 (INSL3) analogues. Eur J Biochem. 269(24): 6287-93.

Daramola O, Stevenson J, Dean G, Hatton D, Pettman G, Holmes W, Field R. 2014. A high-yielding CHO transient system: coexpression of genes encoding EBNA-1 and GS enhances transient protein expression. Biotechnol Prog. 30(1): 132-41

Felker, G. M., J. R. Teerlink, J. Butler, A. F. Hernandez, A. B. Miller, G. Cotter, B. A. Davison, G. Filippatos, B. H. Greenberg, P. Ponikowski, A. A. Voors, T. A. Hua, T. M. Severin, E. Unemori, and M. Metra. 2014. Effect of serelaxin on mode of death in acute heart failure: results from the RELAX-AHF study. J Am Coll Cardiol 64:1591-8.

Mentz, R. J., G. M. Felker, T. Ahmad, W. F. Peacock, B. Pitt, M. Fiuzat, A. P. Maggioni, M. Gheorghiade, Y. Ando, S. J. Pocock, F. Zannad, and C. M. O'Connor. 2013. Learning from recent trials and shaping the future of acute heart failure trials. Am Heart J 166:629-35.

Metra, M., Cotter, G., Davison, B. A., Felker, G. M., Filippatos, G., Greenberg, B. H., Teerlink, J. R. (2013). Effect of serelaxin on cardiac, renal, and hepatic biomarkers in the relaxin in acute heart failure (RELAX-AHF) development program: Correlation with outcomes. Journal of the American College of Cardiology, 61(2), 196-206.

Sherwood, O. D. 2004. Relaxin's Physiological Roles and Other Diverse Actions. Endocrine Reviews 25(2):205-234.

Teerlink, J. R, Cotter G., Davison B. A., Felker G. M., Filippatos G., Greenberg B. H., Ponikowski P., Unemori E., Voors A. A., Adams K. F. Jr, Dorobantu M. I., Grinfeld L. R. Jondeau G., Marmor A., Masip J., Pang P. S., Werdan K., Teichman S. L., Trapani A., Bush C. A., Saini R., Schumacher C., Severin T. M., Metra M. 2013. Serelaxin, recombinant human relaxin-2, for treatment of acute heart failure (RELAX-AHF): a randomised, placebo-controlled trial. Lancet 381(9860):29-39.

Tietjens, J., and J. R. Teerlink. 2016. Serelaxin and acute heart failure. Heart 102:95-9.

Tracey N Wilkinson, Terence P Speed, Geoffrey W Tregear, and Ross A D Bathgate. 2005. Evolution of the relaxin-like peptide family. BMC Evol Biol. 5: 14.

Wilson, S. S., S. I. Ayaz, and P. D. Levy. 2015. Relaxin: a novel agent for the treatment of acute heart failure. Pharmacotherapy 35:315-27.

Xiao, J., Z. Huang, C. Z. Chen, I. U. Agoulnik, N. Southall, X. Hu, R. E. Jones, M. Ferrer, W. Zheng, A. I. Agoulnik and J. J. Marugan. 2013. Identification and optimization of small-molecule agonists of the human relaxin hormone receptor RXFP1. Nat. Commun. 4:1953

The invention claimed is:

1. A fusion polypeptide comprising A-L-B or B-L-A, wherein:
   A is a Relaxin A chain polypeptide or a variant thereof;
   B is a Relaxin B chain polypeptide or a variant thereof; and
   L is a linker polypeptide comprising at least 15 amino acids,
   wherein the fusion polypeptide has Relaxin activity and further comprises a half-life extending moiety.

2. The fusion polypeptide of claim 1, wherein the Relaxin A chain is a Relaxin 2 A chain and the Relaxin B chain is a Relaxin 2 B chain.

3. The fusion polypeptide of claim 1, wherein the linker polypeptide L is 15 to 20 amino acids in length.

4. The fusion polypeptide of claim 1, wherein the linker polypeptide L comprises three or more repeats of the sequence GGGGS (SEQ ID NO. 58).

5. The fusion polypeptide of claim 1, wherein the linker polypeptide L comprises the sequence GGGGSGGGGSGGGGS (SEQ ID NO. 57).

6. The fusion polypeptide of claim 1, wherein the linker polypeptide L consists of the sequence GGGGSGGGGSGGGGS (SEQ ID NO. 57).

7. The fusion polypeptide of claim 1, wherein the half-life extending moiety is an immunoglobulin Fc region.

8. The fusion polypeptide of claim 7, wherein the Fc region is derived from a human IgG1 immunoglobulin.

9. The fusion polypeptide of claim 7, wherein the Fc region has an amino acid sequence comprising at least one of the following combinations of amino acid modifications:
   (i) Fc-YTE (M252Y, S254T, T256E);
   (ii) Fc-FQQ (L234F, L235Q, K322Q);
   (iii) Fc-TM (L234F, L235E, P331S);
   (iv) Fc-YTE-FQQ (M252Y, S254T, T256E, L234F, L235Q, K322Q);

(v) Fc-YTE-TM (M252Y, S254T, T256E, L234F, L235E, P331S),
(vi) Fc-TM-ΔTHT (L234F, L235E, P331S, D221G, K222G, T223G, H224S, T225A),
(vii) Fc-TM-ΔTHTΔK (L234F, L235E, P331S, D221G, K222G, T223G, H224S, T225A, ΔK447),
wherein the amino acid numbering is according to the EU index as in Kabat.

10. The fusion polypeptide of claim 1, wherein the half-life extending moiety is attached to the N-terminus of the fusion polypeptide.

11. The fusion polypeptide of claim 1, wherein the half-life extending moiety is attached to the fusion polypeptide via a connector polypeptide.

12. The fusion polypeptide of claim 11, wherein the connector polypeptide comprises the amino acid sequence GGSP (SEQ ID NO. 56) or GGGGSGGGGSGGGGS (SEQ ID NO. 57).

13. The fusion polypeptide of claim 11, wherein the connector polypeptide comprises the amino acid sequence GGGGSGGGGSGGGGSGGGGS (SEQ ID NO. 69) or AAAGGGGSGGGGSGGGGSGGGGSA (SEQ ID NO. 70).

14. A pharmaceutical composition comprising the fusion polypeptide of claim 1 and a pharmaceutically acceptable excipient.

15. A fusion polypeptide having Relaxin activity, wherein the fusion polypeptide has the sequence as set forth in any one of SEQ ID NOs: 2, 4, 6, 8, 10, 12, 14, 16, 18, 20, 22, 24, 26, and 28.

* * * * *